US011220691B2

(12) United States Patent
Turano et al.

(10) Patent No.: US 11,220,691 B2
(45) Date of Patent: Jan. 11, 2022

(54) METHODS FOR HIGH TAURINE PRODUCTION IN UNICELLULAR ORGANISMS

(71) Applicant: PLANT SENSORY SYSTEMS, LLC, Baltimore, MD (US)

(72) Inventors: Frank J. Turano, Baltimore, MD (US); Michelle B. Price, Baltimore, MD (US)

(73) Assignee: PLANT SENSORY SYSTEMS, LLC, Baltimore, MD (US)

( * ) Notice: Subject to any disclaimer, the term of this patent is extended or adjusted under 35 U.S.C. 154(b) by 0 days.

(21) Appl. No.: 16/919,623

(22) Filed: Jul. 2, 2020

(65) Prior Publication Data
US 2020/0332301 A1  Oct. 22, 2020

Related U.S. Application Data

(62) Division of application No. 16/092,363, filed as application No. PCT/US2016/028958 on Apr. 22, 2016, now abandoned.

(51) Int. Cl.
| | |
|---|---|
| C12N 15/52 | (2006.01) |
| C12N 9/10 | (2006.01) |
| C12N 9/02 | (2006.01) |
| C12N 9/88 | (2006.01) |
| A23K 50/80 | (2016.01) |
| C12P 21/00 | (2006.01) |
| A23K 10/12 | (2016.01) |
| C12P 13/00 | (2006.01) |
| A23L 33/175 | (2016.01) |

(52) U.S. Cl.
CPC .............. *C12N 15/52* (2013.01); *A23K 10/12* (2016.05); *A23K 50/80* (2016.05); *C12N 9/0069* (2013.01); *C12N 9/1085* (2013.01); *C12N 9/88* (2013.01); *C12P 13/001* (2013.01); *C12P 21/00* (2013.01); *C12Y 113/1102* (2013.01); *C12Y 205/01047* (2013.01); *A23L 33/175* (2016.08); *C12Y 401/01* (2013.01)

(58) Field of Classification Search
CPC ...... C12Y 205/01047; C12Y 113/1102; C12Y 401/01; A23L 33/175; C12P 21/00; C12P 13/001; C12N 9/0069; C12N 9/1085; C12N 9/88; C12N 15/52; A23K 10/12; A23K 50/80
See application file for complete search history.

(56) References Cited

U.S. PATENT DOCUMENTS

2012/0222148 A1  8/2012 Turano et al.

FOREIGN PATENT DOCUMENTS

| WO | 2016/057106 A1 | 4/2016 | |
|---|---|---|---|
| WO | WO 2017/176277 A1 * | 10/2017 | ............... C12N 9/02 |

OTHER PUBLICATIONS

Eichhorn EE., Sulfonate-sulfur assimilation in *Escherichia coli*. Doctoral Thesis, Swiss Federal Institute of Technology Zurich, Switzerland, 2000, pp. 1-167. (Year: 2000).*
Van der Ploeg et al., Involvement of CysB and Cbl regulatory proteins in expression of tauABCD operon and other sulfate starvation-inducible genes in *Escherichia coli*. J. Bacteriol., 1997, vol. 179(24): 7671-7678. (Year: 1997).*
International Search Report and Written Opinion issued in Application No. PCT/US2016/028958 dated Aug. 10, 2016, 13 pages.
Eichhorn et al., "Deletion analysis of the *Escherichia coli* taurine and alkanesulfonate transport systems", J. Bacteriology, May 31, 2000, vol. 182(10), pp. 2687-2695.
Dominy et al., "Identification and Characterization of Bacterial Cysteine Dioxygenases: a New Route of Cysteine Degradation for Eubacteria" J. Bacteriology, Aug. 31, 2006, vol. 188(5), pp. 5561-5569.
Huang et al., "The Active Site of O-Acetylserine Sulfhydrylase Is the Anchor Point for Bienzyme Complex Formation with Serine Acetyltransferase", J. Bacteriol., May 31, 2005, vol. 187(9), pp. 3201-3205.
Agnello et al., Discovery of substrate selectivity motif in amino acid decarboxylases unveils a taurine biosynthetic pathway in prokaryotes. ACS Chem. Biol., 2013, vol. 8: 2264-2271 (Year: 2013).
Broun et al., Catalytic plasticity of fatty acid modification enzymes underlying chemical diversity of plant lipids. Science, 1998, vol. 282: 1315-1317. (Year: 1998).
Devos et al., Practical limits of function prediction. Proteins: Structure, Function, and Genetics. 2000, vol. 41: 98-107. (Year: 2000).
Seffernick et al., Melamine deaminase and Atrazine chlorohydrolase: 98 percent identical but functionally different. J. Bacteriol., 2001, vol. 183 (8): 2405-2410. (Year: 2001).
Whisstock et al., Prediction of protein function from protein sequence. Q. Rev. Biophysics., 2003, vol. 36 (3): 307-340. (Year: 2003).
Witkowski et al., Conversion of b-ketoacyl synthase to a Malonyl Decarboxylase by replacement of the active cysteine with glutamine. Biochemistry, 1999, vol. 38: 11643-11650. (Year: 1999).

* cited by examiner

Primary Examiner — Ganapathirama Raghu
(74) Attorney, Agent, or Firm — Rothwell, Figg, Ernst & Manbeck, P.C.

(57) ABSTRACT

The present invention describes an approach to produce or increase hypotaurine or taurine production in unicellular organisms. More particularly, the invention relates to genetic modification of unicellular organisms that include bacteria, algal, microalgal, diatoms, yeast, or fungi. The invention relates to methods to increase taurine levels in the cells by binding taurine or decreasing taurine degradation. The invention can be used in organisms that contain native or heterologous (transgenic) taurine biosynthetic pathways or cells that have taurine by enrichment. The invention also relates to methods to increase taurine levels in the cells and to use the said cells or extracts or purifications from the cells that contain the invention to produce plant growth enhancers, food, animal feed, aquafeed, food or drink supplements, animal-feed supplements, dietary supplements, health supplements or taurine.

5 Claims, 1 Drawing Sheet

Specification includes a Sequence Listing.

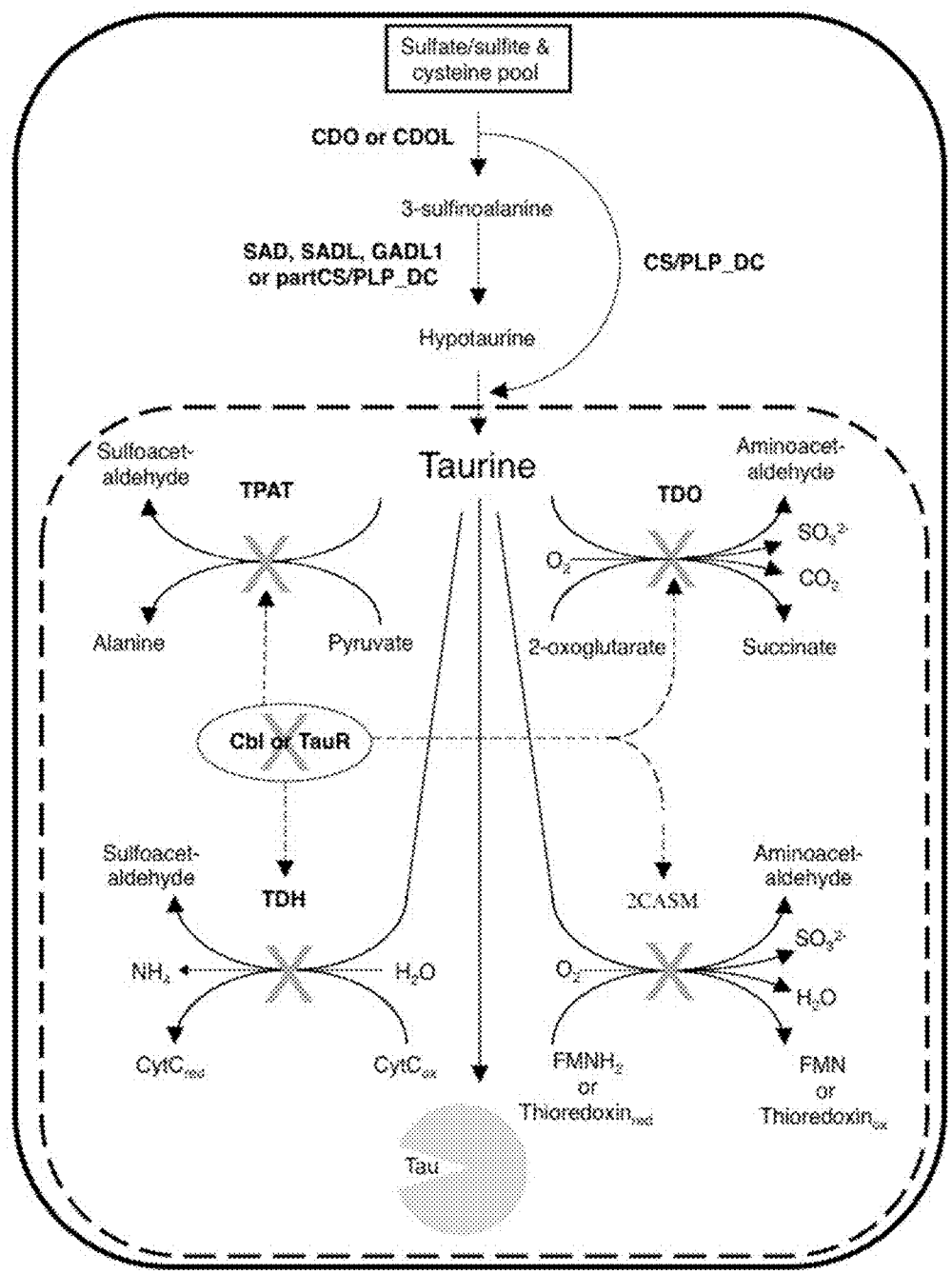

METHODS FOR HIGH TAURINE PRODUCTION IN UNICELLULAR ORGANISMS

CROSS-REFERENCE TO RELATED APPLICATIONS

This application is a division of U.S. patent application Ser. No. 16/092,363, filed on 9 Oct. 2018, now abandoned, which was filed as a 35 U.S.C. § 371 National Stage of International Patent Application No. PCT/US2016/028958, filed 22 Apr. 2016, designating the United States. Each application is incorporated herein by reference in its entirety.

SEQUENCE SUBMISSION

The present application is being filed along with a Sequence Listing in electronic format. The Sequence Listing is entitled 3834118US2SequenceListing.txt, created on 30 Jun. 2020 and is 106 kb in size. The information in the electronic format of the Sequence Listing is incorporated herein by reference in their entirety.

FIELD OF THE INVENTION

The present invention is in the field of recombinant production of taurine. The present invention includes the production of taurine in unicellular organisms. Unicellular organisms include prokaryotic and single-cell eukaryotic organisms, bacteria, microbes, archaea, protozoa, yeast, unicellular algae and unicellular fungi. The invention also relates to methods to increase taurine levels in the cells by binding taurine or decreasing taurine degradation. The invention includes use in organisms that contain native or heterologous taurine biosynthetic pathways or cells that have taurine by enrichment. The invention also relates to methods to increase taurine levels in the cells and to use the said cells or extracts or purifications from the cells that contain the invention to produce plant growth enhancers, food, animal feed, aquafeed, food or drink supplements, animal-feed supplements, dietary supplements, or health supplements.

The publications and other materials used herein to illuminate the background of the invention or provide additional details respecting the practice, are incorporated by reference, and for convenience are respectively grouped in the Bibliography.

BACKGROUND OF THE INVENTION

Taurine is an Essential Compound for Animals

Taurine is essential for human neonatal development (1) and plays an important role in brain development (2, 3). Taurine is involved in the modulation of intracellular calcium homeostasis (4, 5) and may balance glutamate activity, protecting neurons against glutamate excitotoxicity (6, 7). Taurine is also an osmoregulator (8). Taurine is essential for heart function (9), protects the integrity of hepatic tissue (10), and plays a role in photoprotection (11).

Taurine as a Dietary Supplement

Taurine is biosynthesized in most animals and can be found in meat and seafood. Those who do not produce sufficient levels of taurine must acquire it through dietary supplement. Dietary taurine is required for the normal development and growth of cats, (12, 13) human infants, (14) and carnivorous fish.(15-23) Taurine also improves the health and/or growth of other fish species(24-27) and shrimp. (28) Taurine is a feed attractant for fish. (20, 29).

Taurine as a Pharmaceutical or Therapeutic

Taurine is used as a pharmaceutical and therapeutic. Taurine has been used in the treatment of cardiovascular diseases, (30, 31) elevated blood pressure, (32) seizure disorders, (33) hepatic disorders, (34) and alcoholism (35) and may be useful in the treatment of diabetes, (36) Alzheimer's disease, (37) and ocular disorders. (38) Taurine has been shown to prevent obesity (39) and control cholesterol. (40, 41) Taurine acts as an antioxidant and protects against toxicity of various substances. (42-44) Taurine has been shown to prevent oxidative stress induced by exercise (45) and is used in energy drinks to improve performance. (46) Taurine can also be used in topical applications to treat dermatological conditions. (47)

Taurine as a Plant Growth Stimulator

Exogenous application of taurine has been reported to increase crop harvest, yield, and biomass. (48) Applications of taurine by foliar spray, soil and roots application, and seed immersion increase crop production and seedling growth. (48) Exogenous applications of taurine have also been shown to increase photosynthetic capacity of isolated plant cells (protoplasts and chloroplasts). (48)

Metabolic Pathways that Synthesize Taurine

Several metabolic pathways that synthesize taurine and hypotaurine have been identified in animals. The genes and their corresponding gene products and methods for the use of genes and the corresponding peptides to make taurine in cells have been described in the literature. (49-51) Briefly, cysteine and oxygen are converted into 3-sulfinoalanine by cysteine dioxygenase (CDO). 3-sulfinoalanine is converted into hypotaurine by sulfinoalanine decarboxylase (SAD) or glutamate decarboxylase-like 1 (GADL1). (52, 53) Hypotaurine is converted into taurine either by the activity of hypotaurine dehydrogenase (HTDeHase) or by a spontaneous conversion. Cysteamine (2-aminoethanethiol) and oxygen are converted into hypotaurine by cysteamine dioxygenase (ADO), and hypotaurine is converted into taurine. Alternatively cysteine and sulfite are converted into cysteate and hydrogen sulfide by cysteine lyase (cysteine sulfite lyase or cysteine hydrogen-sulfide-lyase). Cysteate is converted into taurine by SAD. (54)

A recent study has shown that several algal and microalgal species can synthesize taurine. (55) In addition, a recent invention identifies algal, microalgal, fungal, yeast, and diatoms genes and their corresponding peptides and describes their use to synthetize taurine in cells. (56) The genes and corresponding peptides include cysteine dioxygenase-like (CDOL), sulfinoalanine decarboxylase-like (SADL), cysteine synthetase/PLP decarboxylase (CS/PLP-DC) or a portion of the cysteine synthetase/PLP decarboxylase (partCS/PLP-DC). The present invention could be used with these organisms and prior art to increase taurine levels in the cell.

Taurine Enrichment

Other studies have shown that multicellular organisms such as rotifers that contain no or low levels of taurine can be enriched with taurine by diffusion (dissolved method), (57-59) or with liposomes. (60) Taurine enrichment methods could also be used with unicellular organisms and in combination with the present invention to increase taurine levels in the cell.

Periplasmic-Binding or Taurine-Binding Proteins

In bacteria, periplasmic binding proteins or substrate-binding proteins, bind specific molecules as part of a multicomponent (peptide) system that is involved in the binding and transportation of specific molecules from the periplasmic space, outside, of the bacterium to the inside of the cell. (61-63) In the ABC transporter system, the substrate-binding protein delivers the bound molecule to transporter proteins on the bacterial membrane where the bound molecule is released into the cell in an energy-dependent manner. In the absence of membrane-bound proteins or energy-dependent releasing peptides (ATP-binding proteins) the substrate molecules remain bound to the substrate-binding protein. In the tripartite ATP-independent periplasmic (TRAP) transporter systems, the substrate-binding protein delivers the bound molecule to membrane bound protein complex (with two peptides) and releases the bound molecule into the cell in an ATP-independent process. In the absence of membrane-bound proteins the substrate molecule remains bound to the substrate-binding protein. Methods to increase pools of sulfonic acids, such as taurine, by expressing only the substrate-binding protein from an ABC transporter or TRAP system, TauA or TauK, respectively, in the cells has been described for use in plant tissues. (51, 64) The present invention describes methods to express substrate-specific binding proteins in the cell of a unicellular organism to increase taurine in the cell.

Sulfonic Acid or Taurine Degradation

In the absence of sulfur, bacteria utilize the sulfonic acid uptake and degradation pathway or the taurine uptake and degradation pathway to mobilize carbon, nitrogen or sulfur. (65-68). Genes and their corresponding peptides involved in the uptake and degradation of taurine are usually on the same operon and are induced in the absence of nitrogen (69, 70) or sulfur (65) or in the presence of taurine. (68, 71). The genes for the degradation enzymes and their corresponding gene products are the TauX and TauY genes (70) that encode taurine dehydrogenase (TDH), the TauD gene (65) that encodes taurine dioxygenase (TDO), the Tpa gene (72) that encodes taurine-pyruvate aminotransferase (TPAT) or the SssuDE (SsuD or SsuE) genes (66) that encode the two-component alkanesulfonate monooxygenase (2CASM).

Transcriptional Regulators

Translational regulators, Cbl or TauR, control the expression and induction of the taurine degradation pathways in bacteria.(65, 72) Cbl is a LysR-type transcriptional regulator of the sulfonic acid uptake and degradation pathway or the taurine uptake and degradation pathway in several bacteria. (73, 74) The Cbl gene is found in Proteobacteria including members of the Alphaproteobacteria, Betaproteobacteria, and Gammaproteobacteria. In bacteria that lack Cbl or Cbl-like transcriptional regulators there is a MocR subfamily of activators, which include TauR, that control the taurine uptake and degradation system. The TauR is found in Rhizobiales and Rhodobacterales of the Alphaproteobacteria, in Burkholderiaceae and Comamonadaceae of the Betaproteobacteria, in Enterobacteriales, Oceanospirillales and Psychromonadales from the Gammaproteobacteria, and in Rhizobiales and *Rhodobacter* of the Alphaproteobacteria. This invention describes how to decrease the expression of these genes or decrease the activities of their corresponding proteins in the cell of a unicellular organism to increase taurine in the cell.

SUMMARY OF THE INVENTION

The invention provides methods and compositions for taurine production in unicellular organisms. More particularly, the invention encompasses the use of polynucleotides for substrate-binding proteins, such as the TauA or TauK genes, to increase taurine in cells or the use of polynucleotides for peptides that degrade taurine. This invention describes methods to use cells with increased taurine pools of the sulfonic acids, such as taurine, by binding taurine in the cell with specific bacterial substrate-binding proteins or by blocking or inhibiting taurine degradation. This invention also describes approaches to block taurine degradation by methods of silencing, mutating or knocking out genes for enzymes in taurine degradation pathway(s) including the TauX or TauY genes that encode TDH, the TauD gene that encodes TDO, the SsuD or SsuE genes that encode 2CASM, or the Tpa gene that encodes TPAT, or by methods of silencing, mutating or knocking out the Cbl gene that encodes LysR-type transcriptional regulator or the TauR gene that encodes a MocR transcriptional regulator. This invention describes the use of polynucleotides for taurine-binding proteins or taurine degradation proteins and their corresponding peptides in unicellular organisms that are capable of producing taurine due to the presence of endogenous (native) or heterologous (gene transfer) taurine biosynthetic pathways or in cells enriched with taurine.

The invention also describes methods for the use of polynucleotides for substrate-binding proteins, such as the TauA or TauK genes, to produce peptides that bind taurine to increase taurine in cells in a unicellular organism that contains taurine by insertion of heterologous polynucleotides or genes (via insertion or transformation) from animal, algal, microalgal, fungal, yeast, diatom and unicellular organisms and their corresponding peptides for taurine synthesis in cells. The genes include CDO, CDOL, SAD, SADL, GADL1, CS/PLP-DC or partCS/PLP-DC.

This invention also describes approaches to block taurine degradation by methods of silencing, mutating or knocking out genes for enzymes in taurine degradation pathway(s) including the TauX or TauY genes that encode TDH, the TauD gene that encodes TDO, the SsuD or SsuE genes that encode 2CASM, or the Tpa gene that encodes TPAT, or by methods of silencing, mutating or knocking out genes for the Cbl gene that encodes LysR-type transcriptional regulator or the TauR gene that encodes a MocR transcriptional regulator. This invention also describes the use of polynucleotides for proteins that degrade taurine in a unicellular organism that contains taurine by insertion of heterologous polynucleotides or genes (via insertion or transformation) from animal, algal, microalgal, fungal, yeast, diatom, and unicellular organisms genes and their corresponding peptides for taurine synthesis in cells. The genes include CDO, CDOL, SAD, SADL, GADL1, CS/PLP-DC or partCS/PLP-DC.

This invention also describes the use of polynucleotides for substrate-binding proteins to increase taurine in cells and the use of methods and polynucleotides to silence, mutate or knock out genes for enzymes in taurine degradation pathway(s) in the same unicellular organism and contains taurine by insertion of heterologous polynucleotides or genes (via insertion or transformation) from animal, algal, microalgal, fungal, yeast, diatom and unicellular organisms genes and their corresponding peptides for taurine synthesis in cells. The genes include CDO, CDOL, SAD, SADL, GADL1, CS/PLP-DC or partCS/PLP-DC.

The invention provides methods for transforming unicellular organisms and constructing vector constructs and other nucleic acid molecules for use therein. The invention also provides methods for transforming unicellular organisms such as bacteria, yeast, fungi, and unicellular algae and constructing vector constructs and other nucleic acid molecules for use therein. The invention also provides methods for mutating the unicellular organisms such as bacteria, yeast, fungi, and unicellular algae and constructing vector constructs and other nucleic acid molecules for use therein. The transgenic or mutant bacteria, yeast, fungi, or unicellular algae will have increased levels of taurine for use as animal feed, food, or as a supplement in animal feed or food or to enhance plant growth or yield.

In addition this invention describes methods to bind taurine in cells to increase taurine in unicellular organisms that produce taurine. (55) This invention describes methods to block taurine degradation by silencing, mutating or knocking out genes for enzymes in the taurine degradation pathway(s). The invention can be used to increase taurine in cells of unicellular organisms that produce taurine through a native or endogenous taurine (55) or heterologous pathway (50, 56) or in cells enriched with taurine. (57-60)

The invention provides isolated cells comprising DNA which does not express a functional taurine degradation enzyme, some isolated cells of the invention comprise (i) exogenous DNA which disrupts the expression of the gene or renders the corresponding peptide for the degradation enzyme non-functional (ii) a basepair mutation that disrupts the expression of the gene or renders the corresponding peptide for the degradation enzyme non-functional, or (iii) a deletion of the entire polynucleotide or a portion of the polynucleotide which disrupts the expression of the gene or renders the corresponding peptide for the degradation enzyme non-functional. The non-functional DNA could be due to changes in the promoter, a portion of the coding region, coding region, or terminator to a polynucleotide which encodes taurine degradation enzyme, that includes TauX, TauY, TauD, Tpa, SsuD, or SsuE or translational activators of those genes including Cbl or TauR genes in a manner where the genes products are not functional. The invention also provides isolated cells comprising non-functional genes or gene products of taurine degradation enzymes from the suppression or decreased accumulation of the corresponding RNA due to antisense RNA or RNA interference.

The invention provides isolated cells comprising exogenous DNA which expresses enzymes of taurine biosynthetic pathways and DNA which does not express a functional taurine degradation enzyme. In one embodiment, an isolated cell comprises three separate expression cassettes. A first expression cassette comprises a first promoter operably linked to a first polynucleotide, a second expression cassette comprises a second promoter operably linked to a second polynucleotide and a third cassette contains DNA which does not express a functional taurine degradation enzyme. In some embodiments, the first polynucleotide encodes CDO or CDOL and the second polynucleotide encodes SAD, SADL or GADL1. In other embodiments the first polynucleotide encodes CDO or CDOL and the second polynucleotide encodes CS/PLP-DC or partCS/PLP-DC. The third polynucleotide comprises the promoter, a portion of the coding region, coding region, or terminator to genes for a taurine degradation enzyme that does not express a functional TauX, TauY, TauD, Tpa, SsuD, or SsuE or translational activators including Cbl or TauR genes in a manner where the genes are not expressed or the gene products are not functional.

The invention provides isolated cells comprising exogenous DNA which expresses enzymes of taurine biosynthetic pathways and taurine binding protein. In one embodiment, an isolated cell comprises three separate expression cassettes. A first expression cassette comprises a first promoter operably linked to a first polynucleotide, a second expression cassette comprises a second promoter operably linked to a second polynucleotide and a third expression cassette comprises a third promoter operably linked to a third polynucleotide. In some embodiments, the first polynucleotide encodes CDO or CDOL and the second polynucleotide encodes SAD, SADL or GADL1. In other embodiments the first polynucleotide encodes CDO or CDOL and the second polynucleotide encodes CS/PLP-DC or partCS/PLP-DC. The third polynucleotide encodes a taurine binding protein (TauA or TauK).

Some isolated cells of the invention comprise exogenous DNA which comprises a single expression cassette and DNA which does not express a functional taurine degradation enzyme. In one embodiment, an isolated cell comprises one single expression cassette. The expression cassette comprises a promoter operably linked to a polynucleotide which encodes (i) CS/PLP-DC; (ii) SADL; (iii) partCS/PLP-DC; (iv) CDOL operably linked to SADL; (v) CDOL operably linked to CS/PLP-DC; (vi) CDOL operably linked to partCS/PLP-DC, (vii) CDO operably linked to SADL; (viii) CDO operably linked to CS/PLP-DC; (ix) CDO operably linked to partCS/PLP-DC; or (x) CDOL operably linked to SAD in a cell that comprises the promoter, coding region, or terminator to taurine degradation enzyme that does not express a functional TauX, TauY, TauD, Tpa, SsuD, or SsuE or translational activators including Cbl or TauR genes in a manner where the genes are not expressed or the gene products are not functional.

The invention provides isolated cells comprising exogenous DNA which expresses enzymes of taurine biosynthetic pathways and a taurine binding protein. In one embodiment, an isolated cell comprises two separate expression cassettes. A first expression cassette comprises a first promoter operably linked to a first polynucleotide and a second expression cassette comprises a second promoter operably linked to a second polynucleotide. In some embodiments, the first polynucleotide encodes DNA which comprises a single expression cassette. The single expression cassette comprises a promoter operably linked to a polynucleotide which encodes (i) CS/PLP-DC; (ii) SADL; (iii) partCS/PLP-DC; (iv) CDOL operably linked to SADL or GADL1; (v) CDOL operably linked to CS/PLP-DC; (vi) CDOL operably linked to partCS/PLP-DC, (vii) CDO operably linked to SADL or GADL1; (viii) CDO operably linked to CS/PLP-DC; (ix) CDO operably linked to partCS/PLP-DC; or (x) CDOL operably linked to SAD. The second polynucleotide comprises a promoter operably linked to a polynucleotide which encodes a taurine binding protein (TauA or TauK).

Some isolated cells of the invention comprise exogenous DNA which comprises a double expression which expresses enzymes of taurine biosynthetic pathways and taurine binding protein in a cell and DNA which does not express a functional taurine degradation enzyme. In one embodiment, an isolated cell comprises two separate expression cassettes. A first expression cassette comprises a first promoter operably linked to a first polynucleotide and a second expression cassette comprises a second promoter operably linked to a second polynucleotide. In some embodiments, the first polynucleotide encodes DNA which comprises a single expression cassette. The single expression cassette comprises a promoter operably linked to a polynucleotide which encodes (i) CS/PLP-DC; (ii) SADL; (iii) partCS/PLP-DC; (iv) CDOL operably linked to SADL or GADL1; (v) CDOL operably linked to CS/PLP-DC; (vi) CDOL operably linked to partCS/PLP-DC, (vii) CDO operably linked to SADL or GADL1; (viii) CDO operably linked to CS/PLP-DC; (ix) CDO operably linked to partCS/PLP-DC; or (x) CDOL operably linked to SAD. The second polynucleotide comprises a promoter operably linked to a polynucleotide which encodes a taurine binding protein (TauA or TauK) in a cell that comprises polynucleotide to the promoter, coding region, or terminator to taurine degradation enzyme that does not express a functional TauX, TauY, TauD, Tpa, SsuD, or SsuE or translational activators including Cbl or TauR genes in a manner where the genes are not expressed or the gene products are not functional.

The invention also describes how to use the cells, fractions of the cells, or extracts from the cells for the present invention for a variety of purposes, including as an additive, feed ingredient, extract or meal. This invention describes the use of polynucleotides and their corresponding polypeptides that either bind or degrade taurine.

The invention provides methods of increasing taurine in the cell of the invention by growing or treating the cell with an agent that increases sulfur or nitrogen concentration in the cell of the invention.

The invention also provides nutritional supplements, feed supplements, and pharmaceutical compositions comprising an extract or meal from the cell of the invention,

BRIEF DESCRIPTION OF THE FIGURE

FIG. 1 shows a unicellular organism (outer black rectangle) with genes and their corresponding taurine biosynthetic proteins (CDO, CDOL, SAD, SADL, GADL1, partCS/PLP-DC, or CS/PLP-DC) in relation to the known animal, yeast, fungal, or algal taurine biosynthetic pathways. Othrologs or paralogs of these genes may occur in some unicellular organisms such as algae. (55) In animals, cysteine and oxygen are converted into 3-sulfinoalanine by CDO. 3-sulfinoalanine is converted into hypotaurine by SAD or GADL1. The indicated genes could be heterologous gene(s) from animals, yeast, fungi, algae or microalgae transferred into the unicellular organism. Alternatively the indicated genes could be their orthologs or homologs that are native or endogenous to the unicellular organism. If there is no native taurine synthetic gene than the animals, yeast, fungi, algae or microalgae can be transferred into the unicellular organism. The technology to increase taurine in the unicellular organism is described in the dashed rectangle, these include (i) genes and the corresponding taurine-substrate binding protein (gray circle bound to Tau), (ii) silenced, mutated, or knocked-out genes (large gray X) for TauD (TDO), TauX or TauY (TDH), Tpa (TPAT), or SsuE or SsuF (2CASM) and their corresponding taurine degradation proteins, or ii) silenced, mutated or knocked-out (large gray X in open oval) genes for cbl or TauR, translational activators. In the absence of functional cbl or TauR gene products, translational activators for the expression of genes and their corresponding products for the taurine degradation pathway(s) (dashed lines) will not be induced or expressed.

DETAILED DESCRIPTION OF THE INVENTION

The present invention provides methods and materials for the production of taurine (2-aminoethanesulfonic acid) in cells and living organisms. In preferred embodiments, the invention provides methods for the genetic transformation of organisms, preferably unicellular organisms, with genes that encode proteins that bind taurine or with silenced or knocked out genes for taurine degradation. The invention also provides methods of using algae, microalgae, bacteria, fungi, yeast, or unicellular cellular organisms with increased levels of endogenous taurine or taurine derivatives such as hypotaurine as a food- or feed-supplement, dietary supplement, as a component of a health supplement or therapy or for plant growth or yield.

The present invention describes the methods for the synthesis of DNA constructs from polynucleotides and vectors and the methods for making transformed organisms including unicellular organisms, microbes, fungi, yeast, algae and microalgae that produce taurine due to the presence of peptides that bind taurine. The present invention is unique in that it describes a method to produce taurine that have advantages of enhanced taurine production and that result in cells with increased nutritional, pharmaceutical, or therapeutic value. The invention can be used in cells enriched with taurine, that contain a native taurine biosynthetic pathway(s), or that contain taurine from the insertion of a heterologous pathway by transformation or gene transfer.

The present invention describes the methods for the synthesis of DNA constructs to inhibit taurine degradation from polynucleotides and vectors and the methods for making transformed organisms including unicellular organisms, microbes, fungi yeast, algae and microalgae. The present invention is unique in that it describes a method to produce taurine that has advantages of enhanced taurine production or hypotaurine and that result in cells with increased nutritional, pharmaceutical, or therapeutic value The present invention describes the methods for the synthesis of DNA constructs for taurine production from polynucleotides and vectors and the methods for making transformed organisms including unicellular organisms, microbes, fungi yeast, algae and microalgae that produce taurine due to the presence of peptides that bind and do not degrade taurine. The present invention is unique in that it describes a method to produce taurine that has advantages of enhanced taurine production or hypotaurine and that result in cells with increased nutritional, pharmaceutical, or therapeutic value.

The present invention describes the insertion of the polynucleotides that encode functional taurine binding proteins (TauA or TauK) or polynucleotides silenced or knocked-out genes for proteins involved in taurine degradation (TauD, SsuD, SsuE, TauX, TauY, or Tpa) or transcriptional regulators (cbl or TauR) for taurine degradation in unicellular organisms, or their use in taurine biosynthetic pathway in unicellular organisms where the pathway does not exist or has not clearly been identified. The invention describes methods for the use of polynucleotides that encode functional CDO, CDOL, SAD, SADL, GADL1, partCS/PLP-DC, or CS/PLP-DC in unicellular organisms. The preferred embodiment of the invention is in bacteria but other organisms may be used.

Enzymes of Taurine Biosynthetic Pathways

Examples of amino acid sequences of enzymes of taurine biosynthetic pathways are provided in the sequence listing: SEQ ID NO:2 (CDO), SEQ ID NO:4 (CDOL), SEQ ID NO:6 (SAD), SEQ ID NO:8 (SADL), SEQ ID NO:10 (GADL1), and SEQ ID NO:12 (CS/PLP-DC). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for CDO, SAD, or GADL from *Danio rerio*, CDOL from *Chlamydomonas reinhardtii*, SADL from Guillardia theta, or CS/PLP-DC from *Micromonas pusilla* may differ to a certain degree from the amino acid sequences of CDO, CDOL, SAD, SADL, GADL1, or CS/PLP-DC in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Substrate Binding Proteins

Examples of amino acid sequences of substrate binding proteins or periplasmic binding proteins that bind taurine are provided in the sequence listing: SEQ ID NO:17 (TauA) and SEQ ID NO:19 (TauK). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for TauA from *Escherichia coli* or TauK from *Roseobacter denitrificans* may differ to a certain degree from the amino acid sequences of TauA or TauK in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Enzymes of Taurine Degradation Pathways

Examples of amino acid sequences of substrate binding proteins or periplasmic binding proteins that bind taurine are provided in the sequence listing: SEQ ID NO:21 (TDO), SEQ ID NO:23 or SEQ ID NO:27 (SsuD), SEQ ID NO:25 or SEQ ID NO:29 (SsuE), SEQ ID NO:31 (TauX), SEQ ID NO:33 (TauY) and SEQ ID NO:35 (Tpa). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for TDO, SsuD or SsuE from *Escherichia coli*, SsuD or SsuE from *Corynebacterium glutamicum*, TauX, TauY, or Tpa from *Roseobacter denitrificans* may differ to a certain degree from the amino acid sequences of TDO, SsuD, SsuE, TauX, TauY, or Tpa in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Translational Regulators

Examples of amino acid sequences of translational regulators are provided in the sequence listing: SEQ ID NO:37 or SEQ ID NO:39 (cbl), or SEQ ID NO:41 or SEQ ID NO:43 (TauR). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for cbl from *Escherichia coli*, or cbl from *Corynebacterium glutamicum* or TauR from *Corynebacterium glutamicum* or Rhodobacteraceae species may differ to a certain degree from the amino acid sequences of cbl or TauR in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, CDO, CDOL, SAD, SADL, GADL1, CS/PLP-DC, TauD (TDO), TauX or TauY (TDH), Tpa (TPAT), SsuD or SsuE (2CASM), cbl, or TauR activity is generally at least 40%, 50%, 60%, 70%, 80% or 90%, preferably 60-90% of the native protein for the native substrate.

The following three groups each contain amino acids that are conserved substitutions for one another: (1) Alanine (A), Serine (S), Threonine (T); (2) Aspartic acid (D), Glutamic acid (E); and (3) Asparagine (N), Glutamine (Q).

Suitable polynucleotides for CDO, CDOL, SAD, SADL, GADL1, CS/PLP-DC, TauA, TauK, SsuD, SsuE, TauX, TauY, Tpa, cbl and TauR As examples, suitable polynucleotides encoding enzymes of taurine biosynthetic and degradation pathways, taurine specific substrate binding proteins, and translational regulators of taurine degradation pathways are described below. The invention is not limited to use of these sequences, however. In fact, any nucleotide sequence which encodes an enzyme of a taurine biosynthetic pathway can be used in an expression vector to produce recombinant protein with CDO, CDOL, SAD. SADL, GADL1, or CS/PLP-DC activity in a unicellular organism with a taurine-binding protein or lacks degradation taurine pathway(s) or lacks regulators of the degradation taurine pathway.

A suitable polynucleotide for CDO is provided in SEQ ID NO:1. Other suitable polynucleotides for use in accordance with the invention may be obtained by the identification of polynucleotides that selectively hybridize to the polynucleotides of SEQ ID NO:1 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1 when it used as a reference for sequence comparison or polynucleotides that encode polypeptides that have substantial identity to amino acid sequence of SEQ ID NO:2 when it used as a reference for sequence comparison.

A suitable polynucleotide for CDOL is provided in SEQ ID NO:3. Other suitable polynucleotides for use in accordance with the invention may be obtained by the identification of polynucleotides that selectively hybridize to the polynucleotides of SEQ ID NO:3 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:3 when it used as a reference for sequence comparison or polynucleotides that encode polypeptides that have substantial identity to amino acid sequence of SEQ ID NO:4 when it used as a reference for sequence comparison.

A suitable polynucleotide for SAD is provided in SEQ ID NO:5. Other suitable polynucleotides for use in accordance with the invention may be obtained by the identification of polynucleotides that selectively hybridize to the polynucleotides of SEQ ID NO:5 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:5 when it used as a reference for sequence comparison or polynucleotides that encode polypeptides that have substantial identity to amino acid sequence of SEQ ID NO:6 when it is used as a reference for sequence comparison.

A suitable polynucleotide for SADL is provided in SEQ ID NO:7. Other suitable polynucleotides for use in accordance with the invention may be obtained by the identification of polynucleotides that selectively hybridize to the polynucleotides of SEQ ID NO:7 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:7 when it used as a reference for sequence comparison or polynucleotides that encode polypeptides that have substantial identity to amino acid sequence of SEQ ID NO:8 when it is used as a reference for sequence comparison.

A suitable polynucleotide for GADL1 is provided in SEQ ID NO:9. Other suitable polynucleotides for use in accordance with the invention may be obtained by the identification of polynucleotides that selectively hybridize to the polynucleotides of SEQ ID NO:9 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:9 when it used as a reference for sequence comparison or polynucleotides that encode polypeptides that have substantial identity to amino acid sequence of SEQ ID NO:10 when it used as a reference for sequence comparison.

A suitable polynucleotide for CS/PLP-DC is provided in SEQ ID NO:11. Other suitable polynucleotides for use in accordance with the invention may be obtained by the identification of polynucleotides that selectively hybridize to the polynucleotides of SEQ ID NO:11 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:11 when it used as a reference for sequence comparison or polynucleotides that encode polypeptides that have substantial identity to amino acid sequence of SEQ ID NO:12 when it used as a reference for sequence comparison.

Suitable polynucleotides for a taurine-binding protein are provided in SEQ ID NO:16 and SEQ ID NO:18. Other suitable polynucleotides for use in accordance with the invention may be obtained by the identification of polynucleotides that selectively hybridize to the polynucleotides of SEQ ID NO:16 or SEQ ID NO:18 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:16 or SEQ ID NO:18 when it used as a reference for sequence comparison or polynucleotides that encode polypeptides that have substantial identity to amino acid sequence of SEQ ID NO:17 or SEQ ID NO:19 when it used as a reference for sequence comparison.

A suitable polynucleotide for TDO is provided in SEQ ID NO:20. Other suitable polynucleotides for use in accordance with the invention may be obtained by the identification of polynucleotides that selectively hybridize to the polynucleotides of SEQ ID NO:20 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:20 when it used as a reference for sequence comparison or polynucleotides that encode polypeptides that have substantial identity to amino acid sequence of SEQ ID NO:21 when it used as a reference for sequence comparison.

Suitable polynucleotides for a SsuD are provided in SEQ ID NO:22 and SEQ ID NO:26. Other suitable polynucleotides for use in accordance with the invention may be obtained by the identification of polynucleotides that selectively hybridize to the polynucleotides of SEQ ID NO:22 or SEQ ID NO:26 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:22 or SEQ ID NO:26 when it used as a reference for sequence comparison or polynucleotides that encode polypeptides that have substantial identity to amino acid sequence of SEQ ID NO:23 or SEQ ID NO:27 when it used as a reference for sequence comparison.

Suitable polynucleotides for a SsuE are provided in SEQ ID NO:24 and SEQ ID NO:28. Other suitable polynucleotides for use in accordance with the invention may be obtained by the identification of polynucleotides that selectively hybridize to the polynucleotides of SEQ ID NO:24 or SEQ ID NO:28 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:24 or SEQ ID NO:28 when it used as a reference for sequence comparison or polynucleotides that encode polypeptides that have substantial identity to amino acid sequence of SEQ ID NO:25 or SEQ ID NO:29 when it used as a reference for sequence comparison.

A suitable polynucleotide for TauX is provided in SEQ ID NO:30. Other suitable polynucleotides for use in accordance with the invention may be obtained by the identification of polynucleotides that selectively hybridize to the polynucleotides of SEQ ID NO:30 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:30 when it used as a reference for sequence comparison or polynucleotides that encode polypeptides that have substantial identity to amino acid sequence of SEQ ID NO:31 when it used as a reference for sequence comparison.

A suitable polynucleotide for TauY is provided in SEQ ID NO:32. Other suitable polynucleotides for use in accordance with the invention may be obtained by the identification of polynucleotides that selectively hybridize to the polynucleotides of SEQ ID NO:32 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:32 when it used as a reference for sequence comparison or polynucleotides that encode polypeptides that have substantial identity to amino acid sequence of SEQ ID NO:33 when it used as a reference for sequence comparison.

A suitable polynucleotide for Tpa is provided in SEQ ID NO:34. Other suitable polynucleotides for use in accordance with the invention may be obtained by the identification of polynucleotides that selectively hybridize to the polynucleotides of SEQ ID NO:34 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:34 when it used as a reference for sequence comparison or polynucleotides that encode polypeptides that have substantial identity to amino acid sequence of SEQ ID NO:35 when it used as a reference for sequence comparison.

Suitable polynucleotides for a cbl are provided in SEQ ID NO:36 and SEQ ID NO:38. Other suitable polynucleotides for use in accordance with the invention may be obtained by the identification of polynucleotides that selectively hybridize to the polynucleotides of SEQ ID NO:36 or SEQ ID NO:38 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:36 or SEQ ID NO:38 when it used as a reference for sequence comparison or polynucleotides that encode polypeptides that have substantial identity to amino acid sequence of SEQ ID NO:37 or SEQ ID NO:39 when it used as a reference for sequence comparison.

A suitable polynucleotide for TauR is provided in SEQ ID NO:40 and SEQ ID NO:42. Other suitable polynucleotides for use in accordance with the invention may be obtained by the identification of polynucleotides that selectively hybridize to the polynucleotides of SEQ ID NO:40 or SEQ ID NO:42 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:40 or SEQ ID NO:42 when it used as a reference for sequence comparison or polynucleotides that encode polypeptides that have substantial identity to amino acid sequence of SEQ ID NO:41 or SEQ ID NO:43 when it used as a reference for sequence comparison.

Another embodiment of the invention is a polynucleotide (e.g., a DNA construct) that encodes a protein that functions as a CDO, CDOL, SAD, SADL, GADL1, CS/PLP-DC, TauA, TauK, TauD, SsuD, SsuE, TauX, TauY, Tpa, cbl and TauR selectively hybridizes to either SEQ ID NO:1, SEQ ID NO:3, SEQ ID NO:5, SEQ ID NO:7, SEQ ID NO:9, SEQ ID NO:11, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40 or SEQ ID NO:42, respectively. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:2, SEQ ID NO:4, SEQ ID NO:6, SEQ ID NO:8, SEQ ID NO:10, SEQ ID NO:12, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41 or SEQ ID NO:43. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

It is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in different species, sequences can be modified to account for the specific codon preferences and GC-content preferences of the organism, as these preferences have been shown to differ.(75-80)

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, mycology, phycology, tissue culture, molecular biology, chemistry, biochemistry, biotechnology, and recombinant DNA technology, which are within the skill of the art.(81-88)

A suitable polynucleotide for use in accordance with the invention may be obtained by cloning techniques using cDNA or genomic libraries, DNA, or cDNA from bacteria, algae, microalgae, diatoms, yeast or fungi which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using fusion-PCR, (89) overlap-PCR (90) or chemical (de novo) synthesis (91-95) using a vendor (e.g. DNA2.0, GE life technologies, GENEART, Gen9, GenScript) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are fused together by recombination.

The recombinant expression cassette or DNA construct includes a promoter that directs transcription in an unicellular organism, operably linked to the polynucleotide encoding a CDO, CDOL, SAD, SADL, GADL1, CS/PLP-DC, partCS/PLP-DC, TauA, or TauK. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Peptide Linkers

Peptide linkers are known to those skilled in the art to connect protein domains or peptides. In general, linkers that contain the amino acids glycine and serine are useful linkers. (96, 97) Other suitable linkers that can be used in the invention include, but are not limited to, those described by Kuusinen et. al. (98) Robinson and Sauer, (99) Armstrong & Gouaux, (100) Arai et. al., (101) Wriggers et. al., (102) and Reddy et. al. (103)

Suitable Promoters

A wide variety of promoters are known to those of ordinary skill in the art, as are other regulatory elements that can be used alone or in combination with promoters. A wide variety of promoters that direct transcription in unicellular organisms can be used in connection with the present invention. (104-106) The features (binding sites and regulatory elements) necessary for the identification and use of functional bacterial promoters are known to those of ordinary skill in the art (107-109) For purposes of describing the present invention, promoters are divided into two types, namely, constitutive promoters and non-constitutive promoters. (105, 110) Constitutive promoters are classified as providing for a range of constitutive expression. Some are weak constitutive promoters, and others are strong constitutive promoters.(111) Other promoters are considered non-constitutive promoters.(112-116) A selected promoter can be an endogenous promoter, i.e. a promoter native to the species and or cell type being transformed. Alternatively, the promoter can be a foreign promoter, which promotes transcription of a length of DNA. The promoter may be of viral origin, including a cauliflower mosaic virus promoter (CaMV 35S), (111) and SV40 promoters from viruses have been used to express target genes. (117) The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed unicellular organism that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a unicellular organism in accordance with the invention, a DNA construct is provided that includes a non-constitutive promoter operably linked to a polynucleotide encoding the desired polypeptide of the invention. The construct is incorporated into a unicellular organism to provide a transformed organism that expresses the polynucleotide in response to a signal. It is understood that the non-constitutive promoter does not continuously produce the transcript or RNA of the invention. But in this embodiment the selected promoter for inclusion of the invention advantageously induces or increases transcription of the gene for the desired polypeptide of the invention in response to a signal, such as a chemical or environmental cue or other stress signal including biotic and/or abiotic stresses or other conditions.

Plastid Transit Peptides

A wide variety of plastid transit peptides are known to those of ordinary skill in the art that can be used in connection with the present invention. Suitable transit peptides which can be used to target any CDO, CDOL, SAD, SADL, GADL1, CS/PLP-DC, partCS/PLP-DC, TauA, or TauK polypeptide to a plastid include, but are not limited, to those described herein and in U.S. Pat. No. 8,779,237, (118) U.S. Pat. No. 8,674,180 (119), U.S. Pat. No. 8,420,888 (120), and U.S. Pat. No. 8,138,393 (121) and in Lee et al. (122) and von Heijne et al. (123) Identification and use of chloroplast plastid targeting sequences for algae are known to those of ordinary skill in the art. (124-127) Cloning a nucleic acid sequence that encodes a transit peptide upstream and in-frame of a nucleic acid sequence that encodes a polypeptide involves standard molecular techniques that are known to those of ordinary skill in the art.

Plastid Transit Peptides

The invention can be targeted for transformation into the chloroplast. Chloroplast targeted transformation systems for algae are known by those of ordinary skill in the art. (113, 115, 128-130)

Suitable Vectors

A wide variety of vectors may be employed to transform a unicellular organism with a construct made or selected in accordance with the invention, including high- or low-copy number plasmids, phage vectors and cosmids. Vector systems, expression cassettes, culture methods, and transformation methods are known by those of ordinary skill in the art. The vectors can be chosen such that operably linked promoter and polynucleotides that encode the desired polypeptide of the invention are incorporated into the genome of the unicellular organism. Other vectors that can operably link promoter and polynucleotides that encode the polypeptide of the invention are incorporated are not incorporated into the host genome but the vector DNA with the clone polynucleotides are autonomously or semi autonomously replicated in the cell. Although the preferred embodiment of the invention is expressed in bacteria, other embodiments may include expression in prokaryotic or unicellular eukaryotic organisms including, but not limited to, yeast, fungi, algae, microalgae, or microbes.

It is known by those of ordinary skill in the art that there exist numerous expression systems available for expression of a nucleic acid encoding a protein of the present invention. There are many commercially available recombinant vectors to transform a unicellular organism. Standard molecular and cloning techniques (85, 88, 131) are available to make a recombinant expression cassette that expresses the polynucleotide that encodes the desired polypeptide of the invention. No attempt will be made to describe in detail the various methods known for the expression of proteins in prokaryotes or eukaryotes. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, to direct transcription, a ribosome-binding site for translational initiation, and a transcription/translation terminator.

Expression in Prokaryotes

Protocols for transformation as well as commonly used vectors with control sequences including promoters for transcription initiation (some with an operator), together with ribosome binding site sequences for use in prokaryotes are known to those of ordinary skill in the art. Commonly used prokaryotic control sequences include promoters for transcription initiation, optionally with an operator, along with ribosome binding site sequences. Commonly used prokaryotic promoters include the beta lactamase, (132) lactose, (132) and tryptophan (133) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art. Those of ordinary skill in the art know the molecular techniques and DNA vectors that are used in bacterial systems.(134-138) In bacteria one messenger RNA can encode for one peptide (referred to as monocistronic) or several independent peptides (referred to as polycistronic). It is known to those of ordinary skill in the art that a portion of a polycistronic messenger RNA can be knocked-out (139) or that heterologous or exogenous genes can be expressed on a monocistronic or polycistronic messenger RNA. (137, 138) Genes can be expressed by modification of bacterial DNA (genomic) through the use of knock-in, gene insertion, or by allelic exchange.(140-145) Specific gene targeting has been used in bacteria using PCR-based methods,(146) and CRISPR/Cas (147-149)

Expression in Algae and Microalgae

Protocols for transformation as well as commonly used vectors with control sequences include promoters for transcription initiation, optionally with an operator, together with ribosome binding site sequences for use in algae and microalgae are known to those of ordinary skill in the art. (105, 128, 150-160). Specific gene targeting systems have been used in algae including ZFNs (161) and transcription activator-like effector nucleases (TALENs). (162)

Expression in Non Plant Eukaryotes

Protocols for transformation, as well as commonly used vectors, are known to those of ordinary skill in the art. Also known to those of ordinary skill in the art are control sequences that include promoters for transcription initiation and ribosome binding site sequences for use in unicellular eukaryotes. The present invention can be expressed in a variety of eukaryotic expression systems such as yeast and protozoa. The vectors usually have expression control sequences, such as promoters, an origin of replication, enhancer sequences, termination sequences, ribosome binding sites, RNA splice sites, polyadenylation sites, transcriptional terminator sequences, and selectable markers.(163, 164) There are numerous vectors that can be used with the invention that are known to those of ordinary skill in the art and include, but are not limited to, pREP, pRIP, pD912, pD1201, pD1211, pD1221, pD1231, pYES2/NT, pYSG-IBA, or pESC-TRP. Synthesis of heterologous proteins and fermentation of products in yeast is known to those of ordinary skill in the art. (165, 166) Protozoa that can be used include, but are not limited to, ciliates, amoebae and *flagellates*. Yeast and fungi that can be used with the invention and the molecular protocols for transformation, and the vectors required for expression of genes in these systems, are known to those of ordinary skill in the art. (167-172) A range of vectors is available. Also available are plasmid vectors, which may be integrative, autonomously replicating high copy-number vectors, or autonomously replicating low copy number vectors. (173, 174) The most common vectors that complement a chromosomal mutation in the host include functional genes such as URA3, HIS3, LEU2, TRP1 and LYS2. Specific gene editing or targeting has been used in unicellular fungi using PCR-based methods,(175-177) Zinc-finger nucleases (ZFNs),(178) transcription activator like effector nucleases (TALENs),(179) and clustered regularly interspaced short palindromic repeats/Cas (CRISPR/Cas).(180, 181)

One of ordinary skill in the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are known to those of ordinary skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs require an appropriate transcriptional terminator to be attached downstream of the desired gene of the invention for proper expression in unicellular organisms. Several such terminators are available and known to persons of ordinary skill in the art. These include, but are not limited to, the tml from CaMV and E9 from rbcS. A variety of available terminators known to function in unicellular organisms can be used in the present invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Selectable markers usually confer resistance to an antibiotic, herbicide or chemical or provide color change, which aid the identification of transformed organisms. The vectors may also include a RNA stability signal, which are 3'-regulatory sequence elements that increase the stability of the transcribed RNA. (182, 183)

Terminators

Terminators are typically located downstream (3') of the gene, after the stop codon (TGA, TAG or TAA). Terminators play an important role in the processing and stability of RNA as well as in translation and may also control gene expression. (184-193) The identification and use of terminators that are required to express genes in unicellular organisms are known to those of ordinary skill in the art.

In addition, polynucleotides that encode a CDO, CDOL, SAD, SADL, partCS/PLP-DC or CS/PLP-DC can be placed in the appropriate vector used to transform unicellular organisms. The polypeptide can be expressed and then isolated from transformed cells, or metabolites can be synthetized and isolated from the transformed cells. Such transgenic organisms can be harvested, and subjected to large-scale protein or metabolite (taurine) extraction and purification techniques.

The vectors may include another polynucleotide insert that encodes a peptide or polypeptide and used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional CDO, CDOL, SAD, SADL, GADL1, CS/PLP-DC, partCS/PLP-DC, TauA, or TauK to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the vacuole, chloroplast (not in fungi), mitochondrion, peroxisomes, secretory pathway, lysosome, endoplasmic reticulum, nucleus or Golgi apparatus in fungi or algae. There are specific signal polypeptides or signal sequences to direct peptide transport to the periplasmic space in bacteria.(194-196) A signal polypeptide or signal sequence is usually at the amino terminus and normally absent from the mature protein due to protease that removes the signal peptide when the polypeptide reaches its final destination. Signal sequences can be a primary sequence located at the N-terminus (123, 197-199), C-terminus (200, 201) or internal (202-204) or tertiary structure.(204) If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (205, 206), iPSORT (207), SignalP (208), PrediSi (209), ELSpred (210) HSLpred (211) and PSLpred (212), MultiLoc (213), SherLoc (214), ChloroP (215), MITOPROT (216), Predotar (217) 3D-PSSM (218) and PredAlgo. (127) Additional methods and protocols are discussed in the literature. (213)

Transformation of Host Cells

Transformation of an unicellular organism can be accomplished in a wide variety of ways within the scope of a person of ordinary skill in the art.(104, 106, 158, 219) Those of ordinary skill in the art can use different algal, diatom, fungal, yeast and bacteria gene transfer techniques that include, but not limited to, *Agrobacterium*-mediated (220) glass beads and polyethylene glycol (PEG),(221, 222) electroporation,(223-226) microprojectile bombardment or ballistic particle acceleration,(227-231) silicon carbide whisker methods,(232, 233), viral infection,(234, 235) or transposon/transposase complexes.(236) Transformation can be targeted to organellular genomes. (130) Other methods to edit, incorporate or move genes into bacteria, fungal algal genomes include, but are not limited to, Zinc-finger nucleases (ZFNs), transcription activator like effector nucleases (TALENs), or clustered regularly interspaced short palindromic repeats/ Cas (CRISPR/Cas).

Gene Silencing by Mutagenesis or Using Recombinant Technologies

Genetic modification to silence or inactivate genes or their corresponding gene products of unicellular organisms can be conducted by radiation-, chemical- or UV-based mutagenesis followed by specific screening for biochemical traits or pathways.(219, 237-241) Radiation-based mutations can silence or inactive a gene or the corresponding gene product by DNA breakage and repair. Chemical- or UV-based mutations usually result in single DNA basepair changes. Mutations can silence or inactive a gene or the corresponding gene product by one of the following (1) result in the introduction of a frame-shift mutation; (2) result in the introduction of premature stop codon; (3) interfere with the ability of the promoter region sequence to direct the transcription of the desired nucleotide sequence, (4) interfere with the ability of the desired nucleotide sequence to be transcribed by the promoter sequence region or (5) introduce amino acid substitution in the gene product to reduce or inhibit activity (enzymatic activity or binding) or interfere with the function of the gene product.

Targeted gene silencing or knockouts can be made in unicellular organisms using phage or viruses, (110, 242-246)

transposons,(236, 247-250) PCR-assisted targeting, (175-177, 251) recombinases or by allelic exchange.(140-145) targeted and random bacterial gene disruptions using a group II intron (Targetron),(252, 253) ZNFs,(178) TALENs, (179) CRISPER-Cas9 or clustered regularly interspaced short palindromic repeats interference (CRISPi). (147-149, 180, 181, 254, 255) In addition, RNA-mediated methods, (256-261) or regulatory RNAs (262-264) have been used to silence or suppress gene expression in unicellular organisms and these techniques and protocols are well known to one with ordinary skill in the art.

Suitable Unicellular Organisms

A wide variety of unicellular host cells may be used in the invention, including prokaryotic and unicellular eukaryotic host cells. These cells or organisms may include yeast, fungi, algae, microalgae, microbes, or unicellular photosynthetic organisms. Preferred host cells for this invention are bacteria including, archaebacteria and eubacteria. Proteobacteria such as members of Alphaproteobacteria, Betaproteobacteria, Gammaproteobacteria, Deltaproteobacteria, and Epsilonproteobacteria can host the invention. Other bacteria including methanotrophs(265) can be used with the invention. Other bacterial genera that can host the invention include, but are not limited to *Bacillus, Salmonella, Lactococcus, Streptococcus, Brevibacterium* and coryneform bacteria. Some specific bacterial species that can be used for the invention include, but are not limited to, *Bacillus subtilis, Brevibacterium ammoniagene, Corynebacterium* crenatum, Corynebacterim pekinese, *Corynebacterium* glutamicumas, *Erwinia citreus, Erwinia herbicola, Escherichia coli, Fusarium venenatum, Gluconobacter oxydans, Propionibacterium freudenreicheii,* and *Propionibacterium denitrificans.* (266).

Unicellular algae, unicellular photosynthetic organisms, and microscopic algae (microphytes or microalgae) cells may be used in the invention. These include, but are not limited to diatoms, green algae (Chlorophyta), and members of the Euglenophyta, Dinoflagellata, Chrysophyta, Phaeophyta, red algae (Rhodophyta), Heterokontophyta, and Cyanobacteria. The invention can also be used to increase the taurine by binding taurine with a taurine binding protein or knocking out genes for taurine degradation in algae that have been shown to synthesize taurine (55) or may have the capability to synthesize taurine. (55) These include but are not limited to Coccomyxa species, *Chlorella* species, Trebouxia *impressa, Tetraselmis species, Chlamydomonas reinhardtii, Micromonas pusilla,* Ostreococcus tauri, Navicula radiosa, *Phaeodactylum tricornutum,* Pseudo-*nitzschia* multiseries, Fragilariopsis cylindrus, *Thalassiosira* weissjlogii, *Nannochloropsis* oceanica, Aureococcus anophagefferens, *Saccharina japonica,* Sargassum species and Bigelowiella *natans.*

Protozoa that may be used in the invention include, but are not limited, to ciliates, amoebae and *flagellates.* Yeast and unicellular fungi that can be used include, but are not limited to *Ashbya gossypii, Blakeslea trispora, Candida flareri, Eremothecium ashbyii, Mortierella isabellina, Pichia pastoris, Saccharomyces cerevisiae,* and *Saccharomyces pombe.*

One embodiment of the invention (Embodiment number 1) is a method for the increased production of taurine in an unicellular organism by the following steps:

1. operably link a promoter to the 5' end of a polynucleotide for a functional SAD (using SAD, SAD1, GADL, partCS/PLP-DC, or CS/PLP-DC) operably linked to a terminator;

2. insert the functional SAD construct (from step 1, Embodiment number 1) into a vector;

3. operably link a promoter to the 5' end of the polynucleotide for a truncated functional Tau-binding protein (using TauA or TauK) operably linked to a terminator;

4. insert the taurine-binding protein polynucleotide construct (from step 3, Embodiment number 1) into a vector containing the functional SAD construct (from step 2, Embodiment number 1); and 5. transform the vector containing the SAD and taurine-binding protein (from step 4, Embodiment number 1) constructs into a unicellular organism.

Another embodiment of the invention (Embodiment number 2) is a method for the increased production of taurine in a unicellular organism by the following steps:

1. operably link a promoter to the 5' end of the polynucleotide for a functional CDO (using CDO or CDOL) operably linked to a terminator;

2. insert the functional CDO polynucleotide construct (from step 1, Embodiment number 2) into a vector;

3. insert the functional SAD construct (from step 1, Embodiment number 1) into a vector containing the functional CDO construct (from step 2, Embodiment number 2);

4. insert the taurine-binding protein polynucleotide construct (from step 3, Embodiment number 1) into a vector containing the functional CDO and SAD constructs (from step 3, Embodiment number 2); and 5. transform the vector containing the functional CDO, SAD, and Tau-binding protein constructs (from step 4, Embodiment number 2) constructs into a unicellular organism.

Another embodiment of the invention (Embodiment number 3) is a method for the increased production of taurine in a unicellular organism by the following steps:

1. insert the taurine-binding protein polynucleotide construct (from step 3, Embodiment number 1) into a vector; and 2. transform the vector containing the taurine-binding protein construct (from step 1, Embodiment number 3) into a unicellular organism.

Another embodiment of the invention (Embodiment number 4) is a method for the increased production of taurine in a unicellular organism by the following steps:

1. operably link a promoter to the 5' end of the polynucleotide for a functional CDO (using either CDO or CDOL) that is linked in-frame, with no linker, with a polynucleotide for a functional SAD (using SAD, SAD1, GADL, partCS/PLP-DC, or partCS/PLP-DC) operably linked to a terminator;

2. insert the CDO/SAD construct (from step 1, Embodiment number 4) into a vector that contains the functional taurine-binding protein (from step 2, Embodiment number 3); and 3. transform the vector containing the functional CDO/SAD and taurine-binding protein constructs (from step 2, Embodiment number 4) into a unicellular organism.

Another embodiment of the invention (Embodiment number 5) is a method for the increased production of taurine in a unicellular organism by the following steps:

1. operably link a promoter to the 5' end of the polynucleotide for functional CDO (using CDO or CDOL) that is linked in-frame with a short, 3 to 66, polynucleotide (linker) to the 5' end of the polynucleotide for a functional SAD (using SAD, SADL, GADL1, partCS/PLP-DC, or CS/PLP-DC) operably linked to a terminator;

2. insert the taurine-binding protein construct (from step 3 above, Embodiment number 1) into a vector containing the CDO/Linker/SAD construct (from step 1, Embodiment number 5); and 3. transform the vector containing the functional CDO/Linker/SAD and Tau-binding protein constructs (from step 2, Embodiment number 5) into a unicellular organism.

Another embodiment of the invention (Embodiment number 6) is a method for the increased production of taurine in a unicellular organism by the following step:

1. knockout the gene for a taurine degradation enzyme using chemical or genetic means by replacement or deletion of a promoter, a portion of the coding region, or terminator to one of the following genes, TauX, TauY, TauD, Tpa, SsuD, or SsuE genes using a pSC101$_{ts}$-sacB, allelic exchange or λ-red recombinase method in a unicellular organism; and 2. transform the vector containing the SAD (from step 2, Embodiment number 1) constructs into the unicellular organism with the mutation or knocked-out TauX, TauY, TauD, Tpa, SsuD, or SsuE gene (from step 2, Embodiment number 6).

Another embodiment of the invention (Embodiment number 7) is a method for the increased production of taurine in a unicellular organism by the following step:

1. transform the vector containing the SAD and taurine-binding protein construct (from step 4, Embodiment number 1) into the unicellular organism with the mutated or knocked-out TauX, TauY, TauD, Tpa, SsuD, or SsuE gene (from step 2, Embodiment number 6).

Another embodiment of the invention (Embodiment number 8) is a method for the increased production of taurine in a unicellular organism by the following step:

1. transform the vector containing the functional CDO, SAD, and taurine-binding protein constructs (from step 5, Embodiment number 2) constructs into the unicellular organism with the mutated or knocked-out TauX, TauY, TauD, Tpa, SsuD, or SsuE gene (from step 2, Embodiment number 6).

Another embodiment of the invention (Embodiment number 9) is a method for the increased production of taurine in a unicellular organism by the following step:

1. transform the vector containing the taurine-binding protein construct (from step 1, Embodiment number 3) into the unicellular organism with the mutated or knocked-out TauX, TauY, TauD, Tpa, SsuD, or SsuE gene (from step 2, Embodiment number 6).

Another embodiment of the invention (Embodiment number 10) is a method for the increased production of taurine in a unicellular organism by the following step:

1. transform the vector containing the functional CDO/SAD construct (from step 2, Embodiment number 4) into the unicellular organism with the mutated or knocked-out TauX, TauY, TauD, Tpa, SsuD, or SsuE gene (from step 2, Embodiment number 6).

Another embodiment of the invention (Embodiment number 11) is a method for the increased production of taurine in a unicellular organism by the following step:

1. transform the vector containing the CDO/SAD construct and taurine-binding protein (from step 3, Embodiment number 4) into the unicellular organism with the mutated or knocked-out TauX, TauY, TauD, Tpa, SsuD, or SsuE gene (from step 2, Embodiment number 6).

Another embodiment of the invention (Embodiment number 12) is a method for the increased production of taurine in a unicellular organism by the following step:

1. transform the vector containing the CDO/Linker/SAD construct (from step 1, Embodiment number 5) into the unicellular organism with the mutated or knocked-out TauX, TauY, TauD, Tpa, SsuD, or SsuE gene (from step 2, Embodiment number 6).

Another embodiment of the invention (Embodiment number 13) is a method for the increased production of taurine in a unicellular organism by the following step:

1. transform the vector containing the CDO/Linker/SAD and taurine-binding protein constructs (from step 2, Embodiment number 5) into the unicellular organism with the mutated or knocked-out TauX, TauY, TauD, Tpa, SsuD, or SsuE gene (from step 2, Embodiment number 6).

Another embodiment of the invention (Embodiment number 14) is a method for the increased production of taurine in a unicellular organism by the following steps:

1. introduce a mutation or knock out the gene for the transcription regulator of the taurine degradation pathways using chemical or genetic means by replacement or deletion of a promoter, a portion of the coding region, or terminator to one of the following genes, cbl, or TauR genes using a pSC101$_{ts\text{-}sacB}$, allelic exchange or λ-red recombinase method and select the mutant or knocked-out unicellular organism; and 2. transform the vector containing the SAD (from step 2, Embodiment number 1) construct into the unicellular organism with the mutated or knocked-out cbl or TauR gene (from step 2, Embodiment number 14).

Another embodiment of the invention (Embodiment number 15) is a method for the increased production of taurine in a unicellular organism by the following step:

1. transform the vector containing the SAD and taurine-binding protein construct (from step 4, Embodiment number 1) into the unicellular organism with the mutated or knocked-out cbl or TauR gene (from step 2, Embodiment number 14).

Another embodiment of the invention (Embodiment number 16) is a method for the increased production of taurine in a unicellular organism by the following step:

1. transform the vector containing the functional CDO and SAD constructs (from step 3, Embodiment number 2) constructs into the unicellular organism with mutated or knocked-out cbl or TauR gene (from step 2, Embodiment number 14).

Another embodiment of the invention (Embodiment number 17) is a method for the increased production of taurine in a unicellular organism by the following step:

1. transform the vector containing the functional CDO, SAD, and taurine-binding protein constructs (from step 5, Embodiment number 2) constructs into the unicellular organism with mutated or knocked-out cbl or TauR gene (from step 2, Embodiment number 14).

Another embodiment of the invention (Embodiment number 18) is a method for the increased production of taurine in a unicellular organism by the following step:

1. transform the vector containing the taurine-binding protein construct (from step 1, Embodiment number 3) into an unicellular organism into the unicellular organism with the mutated or knocked-out cbl or TauR gene (from step 2, Embodiment number 14)

Another embodiment of the invention (Embodiment number 19) is a method for the increased production of taurine in a unicellular organism by the following step:

1. transform the vector containing the functional CDO/SAD construct (from step 2, Embodiment number 4) into the unicellular organism with mutated or knocked-out cbl or TauR gene (from step 2, Embodiment number 14).

Another embodiment of the invention (Embodiment number 20) is a method for the increased production of taurine in a unicellular organism by the following step:

1. transform the vector containing the CDO/SAD construct and taurine-binding protein (from step 3, Embodiment number 4) into the unicellular organism with the mutated or knocked-out cbl or TauR gene (from step 2, Embodiment number 14).

Another embodiment of the invention (Embodiment number 21) is a method for the increased production of taurine in a unicellular organism by the following step:

1. transform the vector containing the CDO/Linker/SAD construct (from step 1, Embodiment number 5) into the unicellular organism with the mutated or knocked-out cbl or TauR gene (from step 2, Embodiment number 14).

Another embodiment of the invention (Embodiment number 22) is a method for the increased production of taurine in a unicellular organism by the following step:

1. transform the vector containing the CDO/Linker/SAD and Tau-binding protein constructs (from step 2, Embodiment number 5) into the unicellular organism with the mutated or knocked-out cbl or TauR gene (from step 2, Embodiment number 14).

Once transformed, the unicellular organism may be treated with other "active agents" either prior to or during the growth to further increase production of taurine. "Active agent," as used herein, refers to an agent that has a beneficial effect on the taurine or amino acid production by the unicellular organism. Some of these agents may be precursors of end products for the reaction catalyzed by CDO, CDOL, SAD, SADL, GADL1, CS/PLP-DC, or partCS/PLP-DC. These compounds could promote growth, development, biomass and yield, and change in metabolism. In addition to the twenty amino acids that are involved in protein synthesis specifically sulfur containing amino acids methionine, and cysteine, other amino acids such as glutamate, glutamine, serine, alanine and glycine, sulfur containing compounds such as sulfite, sulfide, hydrogen sulfide, sulfate, taurine, hypotaurine, cysteate, 2-sulfacetaldehyde, homotaurine, homocysteine, cystathionine, N-acetyl thiazolidine 4 carboxylic acid (ATCA), glutathione, or bile, or other nonprotein amino acids, such as GABA, citrulline and ornithine, or other nitrogen containing compounds such as polyamines may also be used to activate CDO, CDOL, SAD, SADL, GADL1, CS/PLP-DC, or partCS/PLP-DC. Depending on the type of gene construct or recombinant expression cassette, other metabolites and nutrients may be used to activate CDO, CDOL, SAD, SADL, GADL1, CS/PLP-DC, or partCS/PLP-DC. These include, but are not limited to, sugars, carbohydrates, lipids, oligopeptides, mono- (glucose, arabinose, fructose, xylose, and ribose) di-(sucrose and trehalose) and polysaccharides, carboxylic acids (succinate, malate and fumarate) and nutrients such as phosphate, molybdate, or iron.

In some embodiments properties of a transgenic unicellular organism are altered using an agent which increases sulfur concentration in the cell, such as sulfur, sulfite, sulfide, hydrogen sulfide, sulfate, taurine, hypotaurine, homotaurine, cysteate, 2-sulfacetaldehyde, N-acetyl thiazolidine 4 carboxylic acid (ATCA), glutathione, and bile. In other embodiments, the agent increases nitrogen concentration. Amino acids either naturally occurring in proteins (e.g., cysteine, methionine, glutamate, glutamine, serine, alanine, or glycine) or which do not naturally occur in proteins (e.g., GABA, citrulline, or ornithine) and/or polyamines can be used for this purpose.

Pharmaceutical Compositions

The invention provides pharmaceutical compositions that comprise extracts of one or more transgenic organisms described above. Extracts containing hypotaurine or taurine can be used to synthesize or manufacture taurine derivatives, (267, 268) taurine-conjugates(269) or taurine-polymers (270) that may have a wide range of commercial and medicinal applications. (271) Some taurine derivatives can function as organogelators (272) or dyes (273) and can be used in nanosensor synthesis.(274) Some taurine derivatives have anticonvulsant (267) or anti-cancer (275) properties. Other taurine derivatives are used in the treatment of alcoholism. (276, 277) Taurine-conjugated carboxyethylester-polyrotaxanes increase anticoagulant activity. (278) Taurine-containing polymers may increase wound healing. (279, 280) Taurine linked polymers such as poly gamma-glutamic acid-sulfonates are biodegradable and may have applications in the development of drug delivery systems, environmental materials, tissue engineering, and medical materials. (281) Extracts from taurine-containing cells may be used in pharmaceutical or medicinal compositions to deliver taurine, hypotaurine, taurine-conjugates, or taurine-polymers for use in the treatment of congestive heart failure, high blood pressure, hepatitis, high cholesterol, fibrosis, epilepsy, autism, attention deficit-hyperactivity disorder, retinal degeneration, diabetes, and alcoholism. It is also used to improve mental performance and as an antioxidant.

Pharmaceutically acceptable vehicles of taurine, taurine derivatives, taurine-conjugates, or taurine-polymers are tablets, capsules, gel, ointment, film, patch, powder or dissolved in liquid form.

Nutritional Supplements and Feeds

Transgenic cells containing hypotaurine or taurine may be consumed or used to make extracts for nutritional supplements. Transgenic cells that contain hypotaurine or taurine may be used for human consumption. Extracts from transgenic cells containing hypotaurine or taurine may be used as nutritional supplements, as an antioxidant or to improve physical or mental performance. The extracts may be used in the form of a liquid, powder, capsule or tablet.

Transgenic cells containing hypotaurine or taurine may be used as fish or animal feed or used to make extracts for the supplementation of animal feed. Transgenic cells that contain hypotaurine or taurine may be used as animal or fish feed. Extracts from transgenic cells containing taurine may be used as feed supplements in the form of a liquid, powder, capsule or tablet.

Enhancer of Plant Growth or Yield

Transgenic cells that contain hypotaurine or taurine may be used as an enhancer for plant growth or yield. Extracts from transgenic cells containing hypotaurine or taurine may be used as plant enhancers in the form of a liquid, powder, capsule or tablet.

Fermentation and Taurine Purification

Taurine could be purified from the cells or from extracts of the cells or from media from which the cells were grown. The extracted taurine could be used as a food or feed additive, nutrient, pharmaceutical or an enhancer of plant growth or yield. Prokaryotic or eukaryotic cells with the invention can be grown in culture or by fermentation to produce hyptotaurine or taurine. Methods to produce chemical compounds by batch fermentation, fed-batch fermentation, continuous fermentation or in tanks or ponds are well known to one with ordinary skill in the art. (266, 282-292)

Methods such as centrifugation, filtration, crystallization, ion exchange, electrodialysis, solvent extraction, decolorization or evaporation to purify or separate chemical compounds from cells or from liquids or media that grew cells are well known to one with ordinary skill in the art. These methods can be used by one with ordinary skill in the art to purify or separate taurine from cells with the invention, or from liquids or media from which cell suspensions or cell cultures containing the invention were grown. (283, 285, 286, 293-296)

DEFINITIONS

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription. In bacteria the promoter includes a Shine-Dalgarno or ribosomal binding site that can include the sequence AGGAGG (−35 box) and a Pribnow box or RNA polymerase binding site that can include the sequence TATAAT (−10 box).

The term "algal promoter" refers to a promoter capable of initiating transcription in algal cells.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as bacteria, fungi, yeast, bacteria, algae and protozoa, as well as other unicellular organisms.

The term "constitutive" refers to a promoter that is active under most environmental and developmental conditions, such as, for example, but not limited to, the CaMV 35S promoter.

The term "inducible promoter" refers to a promoter that is under chemical (including biomolecules such as sugars, organic acids or amino acids) or environmental control.

The terms "encoding" and "coding"" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The term "degradation" in reference to the "taurine degradation pathway", "taurine degradation enzymes", "taurine degradation system", and "taurine degradation proteins" refers to the process of breakdown, catabolism, or dissimilation of taurine.

The terms "cysteine dioxygenase" and "CDO" refer to the protein (EC:1.13.11.20) that catalyzes the following reaction:

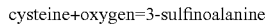

cysteine+oxygen=3-sulfinoalanine

NOTE: 3-sulfinoalanine is another name for cysteine sulfinic acid, cysteine sulfinate, 3-sulphino-L-alanine, 3-sulfino-alanine, 3-sulfino-L-alanine, L-cysteine sulfinic acid, L-cysteine sulfinic acid, cysteine hydrogen sulfite ester or alanine 3-sulfinic acid.

The terms "sulfinoalanine decarboxylase" and "SAD" refer to the protein (4.1.1.29) that catalyzes the following reaction:

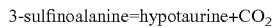

3-sulfinoalanine=hypotaurine+CO$_2$

NOTE: SAD is another name for cysteine-sulfinate decarboxylase, L-cysteine sulfinic acid decarboxylase, cysteine-sulfinate decarboxylase, CADCase/CSADCase, CSAD, cysteic decarboxylase, cysteine sulfinic acid decarboxylase, cysteine sulfinate decarboxylase, sulfoalanine decarboxylase, sulphinoalanine decarboxylase, and 3-sulfino-L-alanine carboxy-lyase.

NOTE: the SAD reaction is also catalyzed by GADL1 (4.1.1.15) (glutamic acid decarboxylase like 1). Although called GADL1 the enzyme has been shown to catalyze the SAD reaction. (52, 53)

Other names for hypotaurine are 2-aminoethane sulfinate, 2-aminoethylsulfinic acid, and 2-aminoethanesulfinic acid.

Other names for taurine are 2-aminoethane sulfonic acid, aminoethanesulfonate, L-taurine, taurine ethyl ester, and taurine ketoisocaproic acid 2-aminoethane sulfinate.

The terms "cysteamine dioxygenase" and "ADO" refer to the protein (EC 1.13.11.19) that catalyzes the following reaction:

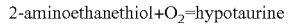

2-aminoethanethiol+O$_2$=hypotaurine

ADO is another name for 2-aminoethanethiol:oxygen oxidoreductase, persulfurase, cysteamine oxygenase, and cysteamine: oxygen oxidoreductase.

Other names for 2-aminoethanethiol are cysteamine or 2-aminoethane-1-thiol, b-mercaptoethylamine, 2-mercaptoethylamine, decarboxycysteine, and thioethanolamine.

The terms "taurine-pyruvate aminotransferase" and "TPAT" refer to the protein (EC 2.6.1.77) that catalyzes the following reaction:

taurine+pyruvate=L-alanine+2-sulfoacetaldehyde

TPAT is another name for taurine transaminase or taurine transaminase aminotransferase The term "Tpa" refers to the gene that encodes TPAT.

The terms "sulfoacetaldehyde acetyltransferase" and "SA" refer to the protein (EC:2.3.3.15) that catalyzes the following reaction:

acetyl phosphate+sulfite=sulfoacetaldehyde+orthophosphate

SA is another name for acetyl-phosphate:sulfite S-acetyltransferase or Xsc.

The terms "taurine dehydrogenase" and "TDH" refer to the protein (EC:1.4.2.-) that catalyzes the following reaction:

taurine+water=ammonia+2-sulfoacetaldehyde

TDH is another name for taurine:oxidoreductase, taurine:ferricytochrome-c oxidoreductase, The term "TauX" or "TauY" refers to the genes that encode for the small and large subunits of TDH, respectively.

The terms "taurine dioxygenase" and "TDO" refer to the protein (EC:1.14.11.17) that catalyzes the following reaction:

taurine+2-oxoglutarate+$O_2$=sulfite+aminoacetaldehyde+succinate+$CO_2$

TDO is another name for 2-aminoethanesulfonate dioxygenase, alpha-ketoglutarate-dependent taurine dioxygenase, taurine, or 2-oxoglutarate: $O_2$ oxidoreductase.

2-oxoglutarate is another name for alpha-ketoglutarate.

The term "TauD" refers to the gene that encodes TDO.

The term "two-component alkanesulfonate monooxygenase" or "2CASM" that catalyzes the following reaction:

taurine+$O_2$+$FMNH_2$=Aminoacetaldehyde+$SO_3^{2-}$+$H_2O$+FMN or taurine+$O_2$+Thioredoxinred=Aminoacetaldehyde+$SO_3^{2-}$+$H_2O$+Thioredoxin$_{ox}$ The term "SssuDE", "SsuD" or "SsuE" refers to the genes that encode the two-component alkanesulfonate monooxygenase (2CASM).

The term "functional" with reference to CDO, CDOL, SAD, SADL, GADL1, partCS/PLP-DC, or CS/PLP-DC refers to peptides, proteins or enzymes that catalyze the CDOL, SADL, ADO, TPAT, or CS/PLP-DC reactions, respectively.

The terms "cysteine synthetase/PLP decarboxylase" and "CS/PLP-DC" refer to the protein that catalyzes the following reactions:

cysteine+oxygen=hypotaurine cysteine+oxygen=taurine

O-acetyl-L-serine+hydrogen sulfide=hypotaurine

O-acetyl-L-serine+hydrogen sulfide=taurine

The terms "portion of the cysteine synthetase/PLP decarboxylase" and "partCS/PLP-DC" refers to the protein that catalyzes a decarboxylase reaction which cleaves carbon-carbon bonds and includes, but is not limited to, the following substrate and end-products:

Aspartate=beta-alanine+$CO_2$

Glutamate=4-aminobutanoate+$CO_2$

Cysteic acid=2-aminoethane sulfonate+$CO_2$

Note: another name for 4-aminobutanoate is gamma-aminobutyric acid (GABA).

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic" includes reference to a unicellular, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell the genotype of which has been altered by the presence of heterologous nucleic acid including those cell altered or created by budding or conjugation propagation from the initial transgenic cell.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt solution. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (297), where the $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature. (131, 298) Unless otherwise stated, in the present application high stringency is defined as hybridization in 4×SSC, 5×Denhardt solution (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT, (299) can perform an optimal alignment of sequences for comparison using a homology alignment algorithm called GAP, (300) search for similarity using Tfasta and Fasta, (301) by computerized implementations of these algorithms widely available on-line or from various vendors (Intelligenetics, Genetics Computer Group). CLUSTAL allows for the alignment of multiple sequences (302-304) and program PileUp can be used for optimal global alignment of multiple sequences. (305) The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (300) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62. (306)

Unless otherwise stated, sequence identity or similarity values refer to the value obtained using the BLAST 2.0 suite of programs using default parameters. (307) As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (308, 309) and XNU. (310)

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch, (311) thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (300). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention

REFERENCES

1. Sturman J A (1988) Taurine in development. *Journal of Nutrition* 118:1169-1176.
2. Sturman J A & Hayes K C (1980) The biology of taurine in nutrition and development. *Advances in Nutritional Research* 3:231-299.
3. Chen X C, Pan Z L, Liu D S, & Han X (1998) Effect of taurine on human fetal neuron cells: Proliferation and differentiation. *Advances in Experimental Medicine and Biology* 442:397-403.
4. El Idrissi A & Trenkner E (1999) Growth factors and taurine protect against excitotoxicity by stabilizing calcium homeostasis and energy metabolism. *Journal of Neuroscience* 19:9459-9468.
5. El Idrissi A & Trenkner E (2003) Taurine regulates mitochondrial calcium homeostasis. *Advances in Experimental Medicine and Biology* 526:527-536.
6. Trenkner E (1990) Possible role of glutamate with taurine in neuron-glia interaction during cerebellar development. *Progress in Clinical and Biological Research* 351:133-140.
7. Wu H, et al. (2005) Mode of action of taurine as a neuroprotector. *Brain Research* 1038:123-131.
8. Schaffer S, Takahashi K, & Azuma J (2000) Role of osmoregulation in the actions of taurine. *Amino Acids* 19:527-546.
9. Chapman R A, Suleiman M S, & Earm Y E (1993) Taurine and the heart. *Cardiovascular Research* 27:358-363.
10. Tabassuma H, Rehmana H, Banerjeeb B D, Raisuddina S, & Parvez S (2006) Attenuation of tamoxifen-induced hepatotoxicity by taurine in mice. *Clinica Chimica Acta* 370:129-136.
11. Rocket N, et al. (2007) The osmolyte taurine protects against ultraviolet B radiation-induced immunosuppression. *Journal of Immunology* 179:3604-3612.
12. Knopf K, Sturman J A, Armstrong M, & Hayes A C (1978) Taurine: An essential nutrient for the cat. *Journal of Nutrition* 108:773-778.
13. Morris J G, Rogers Q R, & Pacioretty L M (1990) Taurine: an essential nutrient for cats. *Journal of Small Animal Practice* 31(10):502-509.
14. Chesney R, et al. (1998) The Role of Taurine in Infant Nutrition. *Taurine* 3, Advances in Experimental Medicine and Biology, eds Schaffer S, Lombardini J, & Huxtable R (Springer U S), Vol 442, pp 463-476.
15. Gibson G T, et al. (2007) Supplementation of taurine and methionine to all-plant protein diets for rainbow trout (Oncorhynchus mykiss). *Aquaculture* 269:514-524.
16. Buentello A, Jirsa D, Barrows F T, & Drawbridge M (2015) Minimizing fishmeal use in juvenile California yellowtail, Seriola lalandi, diets using non-G M soybeans selectively bred for aquafeeds. *Aquaculture* 435(0):403-411.
17. Rossi W, Moxely D, Buentello A, Pohlenz C, & Gatlin D M (2013) Replacement of fishmeal with novel plant feedstuffs in the diet of red drum *Sciaenops ocellatus*: an assessment of nutritional value. *Aquaculture Nutrition* 19:72-81.
18. Watson A M, Buentello A, & Place A R (2014) Partial replacement of fishmeal, poultry by-product meal and soy protein concentrate with two non-genetically modified soybean cultivars in diets for juvenile cobia, *Rachycentron canadum. Aquaculture* 434(0):129-136.
19. Takagia S, et al. (2008) Taurine is an essential nutrient for yellowtail *Seriola quinqueradiata* fed non-fish meal diets based on soy protein concentrate. *Aquaculture* 280:198-205.
20. Lunger A N, McLean E, Gaylord T G, Kuhn D, & Craig S R (2007) Taurine supplementation to alternative dietary proteins used in fish meal replacement enhances growth of juvenile cobia (*Rachycentron canadum*). *Aquaculture* 271:401-410.
21. Watson A M, Barrows F T, & Place A R (2013) Taurine supplementation of plant derived protein and n-3 fatty acids are critical for optimal growth and development of cobia, Rachycentron canadum. *Lipids* 48(9):899-913.
22. Watson A M, Barrows F T, & Place A R (2013) Taurine supplemented plant protein based diets with alternative lipid sources for juvenile gilthead sea bream, *Sparus aurata. Journal of Fisheries and Aquaculture* 4:59-66.
23. Park G S, Takeuchi T, Yokoyama M, & Seikai T (2002) Optimal dietary taurine level for growth of juvenile Japanese flounder *Paralichthys olivaceus. Fisheries Science* 68:824-829.
24. Gaylord T G, Teague A M, & Barrows F T (2006) Taurine supplementation of all-plant protein diets for rainbow trout (*Oncorhynchus mykiss*). *Journal of the World Aquaculture Society* 37:509-517.
25. Salze G P & Davis D A (2015) Taurine: a critical nutrient for future fish feeds. *Aquaculture* 437:215-229.
26. Yang H, Tian L, Huang J, Liang G, & Liu Y (2013) Dietary taurine can improve the hypoxia-tolerance but not the growth performance in juvenile grass carp *Ctenopharyngodon idellus. Fish physiology and biochemistry* 39(5):1071-1078.
27. Kuz'mina V V, Gavrovskaya L K, Rusanova P V, Kulivatskaya E A, & Ryzhova O V (2011) Effect of taurine on the glycemia level and the activity of hydrolases in the intestinal mucosa in carp (*Cyprinus carpio* L.). *Inland Water Biol* 4(2):242-248.
28. Yue Y-R, et al. (2012) The effect of dietary taurine supplementation on growth performance, feed utilization and taurine contents in tissues of juvenile white shrimp (*Litopenaeus vannamei*, Boone, 1931) fed with low-fishmeal diets. *Aquaculture Research* DOI: 10.1111/j 0.1365-2109.2012.03135.x.
29. Brotons Martinez J, Chatzifotis S, Divanach P, & Takeuchi T (2004) Effect of dietary taurine supplementation on growth performance and feed selection of sea bass Dicentrarchus labrax fry fed with demand-feeders. *Fisheries Science* 70(1):74-79.
30. Milei J, et al. (1992) Reduction of reperfusion injury with preoperative rapid intravenous infusion of taurine during myocardial revascularization. *American Heart Journal* 123:339-345.
31. Militante J D & Lombardini J B (2002) Treatment of hypertension with oral taurine. *Endocrinology* 147:3276-3284.
32. Fujita T, Ando K, Noda H, Ito Y, & Sato Y (1987) Effects of increased adrenomedullary activity and taurine in young patients with borderline hypertension. *Circulation* 75:525-532.
33. McCown T J, Givens B S, & Breese G R (1987) Amino acid influences on seizures elicited within the inferior colliculus. *Pharmacology and Experimental Therapeutics* 243:603-608.
34. Matsuyama Y, Morita T, Higuchi M, & Tsujii T (1983) The effect of taurine administration on patients with acute hepatitis. *Progress in Clinical and Biological Research* 125:461-468.
35. Ikeda H (1977) Effects of taurine on alcohol withdrawal. *Lancet* 2:509.
36. Franconi F, Di Leo M A S, Bennardini F, & Ghirlanda G (2004) Is taurine beneficial in reducing risk factors for diabetes mellitus? *Neurochemical Research* 29:143-150.
37. Paula-Lima A C, De Felice F G, Brito-Moreira J, & Ferreira S T (2005) Activation of GABAA receptors by taurine and muscimol blocks the neurotoxicity of [beta]-amyloid in rat hippocampal and cortical neurons. *Neuropharmacology* 49:1140-1148.
38. Nakamori K, et al. (1993) Quantitative evaluation of the effectiveness of taurine in protecting the ocular surface against oxidant. *Chemical & Pharmaceutical Bulletin* 41:335-338.
39. Zhang M, et al. (2004) Beneficial effects of taurine on serum lipids in overweight or obese non-diabetic subjects. *Amino Acids* 26:267-271.
40. Yokogoshi H, et al. (1999) Dietary taurine enhances cholesterol degradation and reduces serum and liver cholesterol concentrations in rats fed a high-cholesterol diet. *Journal of Nutrition* 129:1705-1712.
41. Yamamoto K, et al. (2000) Dietary taurine decreases hepatic secretion of cholesterol ester in rats fed a high-cholesterol diet. *Pharmacology* 60:27-33.
42. Green T R, Fellman R I, Eicher A L, & Pratt K L (1991) Antioxidant role and subcellular location of hypotaurine and taurine in human neutrophils. *Biochimica et Biophysica Acta* 1073:91-97.
43. Gürer H, Ozgünes H, Saygin E, & Ercal N (2001) Antioxidant effect of taurine against lead-induced oxidative stress. *Archives of Environmental Contamination and Toxicology* 41:397-402.
44. Das J, Ghosh J, Manna P, & Sil P C (2008) Taurine provides antioxidant defense against NaF-induced cytotoxicity in murine hepatocytes. *Pathophysiology* 15:181-190.
45. Zhang M, et al. (2004) Role of taurine supplementation to prevent exercise-induced oxidative stress in healthy young men. *Amino Acids* 26:203-207.
46. Williams M (2005) Dietary supplements and sports performance: Amino acids. *Journal of the International Society of Sports Nutrition* 2:63-67.
47. da Silva D L P, et al. (2008) Penetration profile of taurine in the human skin and its distribution in skin layers. *Pharmaceutical Research* 25:1846-1850.
48. Suzuki A, Kajita T, & Furushima M (1989) 4877447.

49. Honjoh K I, et al. (2010) Enhancement of menadione stress tolerance in yeast by accumulation of hypotaurine and taurine: co-expression of cDNA clones, from *Cyprinus carpio*, for cysteine dioxygenase and cysteine sulfinate decarboxylase in *Saccharomyces cerevisiae*. *Amino Acids* 38:1173-1183.
50. Turano F J, Turano K A, Carlson P S, & Kinnersley A M (2012) U.S. Pat. No. 9,267,148.
51. Turano F J, Price M B, & Turano K A (2014).
52. Liu P, et al. (2012) Role of Glutamate Decarboxylase-like Protein 1 (GADL1) in Taurine Biosynthesis. *Journal of Biological Chemistry* 287(49):40898-40906.
53. Winge I, et al. (2015) Mammalian CSAD and GADL1 have distinct biochemical properties and patterns of brain expression. *Neurochemistry International* 90:173-184.
54. Goto T, Matsumoto T, Murakami S, Takagi S, & Hasumi F (2003) Conversion of cysteate into taurine in liver of fish. *Fisheries science* 69(1):216-218.
55. Tevatia R, et al. (2015) The taurine biosynthetic pathway of microalgae. *Algal Research* 9:21-26.
56. Turano F J (2016).
57. Matsunari H, et al. (2005) Effect of Feeding Rotifers Enriched with Taurine on Growth Performance and Body Composition of Pacific Cod Larvae <I>Gadus macrocephalus</I>. *Aquaculture Science* 53(3):297-304.
58. Salze G, McLean E, & Craig S R (2012) Dietary taurine enhances growth and digestive enzyme activities in larval cobia. *Aquaculture* 362-363:44-49.
59. Takahashi T, Amano T, & Takeuchi T (2005) Establishment of Direct Enrichment Method of Taurine to Rotifer. *Aquaculture Science* 53(2):121-126.
60. Hawkyard M, Laurel B, Barr Y, Hamre K, & Langdon C (2015) Evaluation of liposomes for the enrichment of rotifers (*Brachionus* sp.) with taurine and their subsequent effects on the growth and development of northern rock sole (*Lepidopsetta polyxystra*) larvae. *Aquaculture* 441: 118-125.
61. Higgins C F (2001) ABC transporters: physiology, structure and mechanism—an overview. *Research in Microbiology* 152:205-210.
62. Berntsson R P A, Smits S H J, Schmitt L, Slotboom D-J, & Poolman B (2010) A structural classification of substrate-binding proteins. *FEBS Letters* 584(12):2606-2617.
63. Mulligan C, Fischer M, & Thomas G H (2011) Tripartite ATP-independent periplasmic (TRAP) transporters in bacteria and archaea. *FEMS microbiology reviews* 35(1): 68-86.
64. Turano F J & Turano K A (2011) U.S. Pat. No. 8,742, 204.
65. van der Ploeg J R, et al. (1996) Identification of sulfate starvation-regulated genes in *Escherichia coli*: a gene cluster involved in the utilization of taurine as a sulfur source. *Journal of Bacteriology* 178(18):5438-5446.
66. van der Ploeg J R, Cummings N J, Leisinger T, & Connerton I F (1998) *Bacillus subtilis* genes for the utilization of sulfur from aliphatic sulfonates. *Microbiology* 144(9):2555-2561.
67. Brüggemann C, Denger K, Cook A M, & Ruff J (2004) Enzymes and genes of taurine and isethionate dissimilation in *Paracoccus denitrificans*. *Microbiology* 150(4): 805-816.
68. Denger K, Ruff J, Schleheck D, & Cook A M (2004) *Rhodococcus opacus* expresses the xsc gene to utilize taurine as a carbon source or as a nitrogen source but not as a sulfur source. *Microbiology* 150(6):1859-1867.
69. Denger K, Smits T H M, & Cook A M (2006) Genome-enabled analysis of the utilization of taurine as sole source of carbon or of nitrogen by *Rhodobacter sphaeroides* 2.4.1. *Microbiology* 152(11):3197-3206.
70. Krejcik Z, Schleheck D, Hollemeyer K, & Cook A M (2012) A five-gene cluster involved in utilization of taurine-nitrogen and excretion of sulfoacetaldehyde by *Acinetobacter radioresistens* SH164. *Archives of microbiology* 194(10):857-863.
71. Gorzynska A K, Denger K, Cook A M, & Smits T H M (2006) Inducible transcription of genes involved in taurine uptake and dissimilation by *Silicibacter pomeroyi* DSS-3T. *Archives of microbiology* 185(5): 402-406.
72. Novak R T, Gritzer R F, Leadbetter E R, & Godchaux W (2004) Phototrophic utilization of taurine by the purple nonsulfur bacteria *Rhodopseudomonas palustris* and *Rhodobacter sphaeroides*. *Microbiology* 150(6): 1881-1891.
73. van der Ploeg J R, Iwanicka-Nowicka R, Kertesz M A, Leisinger T, & Hryniewicz M M (1997) Involvement of CysB and Cbl regulatory proteins in expression of the tauABCD operon and other sulfate starvation-inducible genes in *Escherichia coli*. *J Bacteriol* 179(24):7671-7678.0
74. van der Ploeg J R, Iwanicka-Nowicka R, Bykowski T, Hryniewicz M M, & Leisinger T (1999) The *Escherichia coli* ssuEADCB Gene Cluster Is Required for the Utilization of Sulfur from Aliphatic Sulfonates and Is Regulated by the Transcriptional Activator Cbl. *Journal of Biological Chemistry* 274(41):29358-29365.
75. Bennetzen J L & Hall B D (1982) Codon selection in yeast. *J Biol Chem* 257(6):3026-3031.
76. Gouy M & Gautier C (1982) Codon usage in bacteria: correlation with gene expressivity. *Nucleic Acids Research* 10(22): 7055-7074.
77. Campbell W H & Gown G (1990) Codon Usage in Higher Plants, Green Algae, and Cyanobacteria. *Plant Physiology* 92(1): 1-11.
78. Douglas E S & Penny L S (The Plastid Genome of the Cryptophyte Alga, Guillardia theta: Complete Sequence and Conserved Synteny Groups Confirm Its Common Ancestry with Red Algae. *Journal of Molecular Evolution* 48(2):236-244.
79. Yoon H S, Müller K M, Sheath R G, Ott F D, & Bhattacharya D (2006) Defining the major lineages of red algae (rhodophyta). *Journal of Phycology* 42(2):482-492.
80. Fletcher S P, Muto M, & Mayfield S P (2007) Optimization of Recombinant Protein Expression in the Chloroplasts of Green Algae. *Transgenic Microalgae as Green Cell Factories*, eds León R, Galván A, & Fernández E (Springer New York, N.Y., N.Y.), pp 90-98.
81. Langenheim J H & Thimann K V (1982) *Botany: Plant Biology and its Relation to Human Affairs* (John Wiley & Sons Inc., New York).
82. Vasil I K (1984) *Cell Culture and Somatic Cell Genetics of Plants: Laboratory Procedures and Their Applications* (Academic Press, Orlando).
83. Stanier R, Ingrahm J, Wheelis M, & Painter P (1986) *The Microbial World* (Prentice-Hall, New Jersey) 5 Ed.
84. Dhringra O D & Sinclair J B (1985) *Basic plant pathology methods* (CRC Press, Boca Raton, Fla.).
85. Maniatis T, Fritsch E F, & Sambrook J (1985) *Molecular Cloning: A Laboratory Manual: DNA Cloning* (Cold Spring Harbor, New York).
86. Gait (1984) *Oligonucleotide Synthesis—A Practical Approach* (IRL Press, Washington, D.C.).
87. Hames D D & Higgins S J (1984) *Nucleic Acid Hybridization: A Practical Approach* (IRL Press, Washington D.C.).

88. Watson J D, Gilman M, Witowski J, & Zoller M (1992) *Recombinant DNA* (Scientific American Books, New York).
89. Szewczyk E, et al. (2006) Fusion PCR and gene targeting in *Aspergillus nidulans*. *Nature Protocols* 1:3111-3121.
90. Ho S N, Hunt H D, Horton R M, Pullen J K, & Pease L R (1989) Site-directed mutagenesis by overlap extension using the polymerase chain reaction. *Gene* 77:51-59.
91. Fuhrmann M, Oertel W, & Hegemann P (1999) A synthetic gene coding for the green fluorescent protein (GFP) is a versatile reporter in *Chlamydomonas reinhardtii*. *Plant Journal* 19:353-361.
92. Mandecki W & Bolling T J (1988) *FokI method of gene synthesis*. *Gene* 68:101-107.
93. Stemmer W P, Crameri, A., Ha, K. D., Brennan, T. M. and Heyneker, H. L. (1995) Single-step assembly of a gene and entire plasmid from large numbers of oligodeoxyribonucleotides. *Gene* 164:49-53.
94. Gao X, Yo P, Keith A, Ragan T J, & Harris T K (2003) Thermodynamically balanced inside-out (TBIO) PCR-based gene synthesis: a novel method of primer design for high-fidelity assembly of longer gene sequences. *Nucleic Acids Research* 31:e143.
95. Young L & Dong Q (2004) Two-step total gene synthesis method. *Nucleic Acids Research* 32:e59.
96. Trinh R, Gurbaxani B, Morrison S L, & Seyfzadeh M (2004) Optimization of codon pair use within the (GGGGS)3 linker sequence results in enhanced protein expression. *Molecular immunology* 40(10):717-722.
97. Chang T W & Yu L (1999) Genetic engineering. (Google Patents).
98. Kuusinen A, Arvola M, & Keinanen K (1995) Molecular dissection of the agonist binding site of an AMPA receptor. *Embo J* 14(24):6327-6332.
99. Robinson C R & Sauer R T (1998) Optimizing the stability of single-chain proteins by linker length and composition mutagenesis. *Proceedings of the National Academy of Sciences of the United States of America* 95(11): 5929-5934.
100. Armstrong N & Gouaux E (2000) Mechanisms for activation and antagonism of an AMPA-sensitive glutamate receptor: crystal structures of the GluR2 ligand binding core. *Neuron* 28(1):165-181.
101. Arai R, Ueda H, Kitayama A, Kamiya N, & Nagamune T (2001) Design of the linkers which effectively separate domains of a bifunctional fusion protein. *Protein engineering* 14(8):529-532.
102. Wriggers W, Chakravarty S, & Jennings P A (2005) Control of protein functional dynamics by peptide linkers. *Biopolymers* 80(6):736-746.
103. Reddy Chichili V P, Kumar V, & Sivaraman J (2013) Linkers in the structural biology of protein-protein interactions. *Protein science: a publication of the Protein Society* 22(2): 153-167.
104. Rosano G L & Ceccarelli E A (2014) Recombinant protein expression in microbial systems. *Frontiers in microbiology* 5:341.
105. Hlavova M, Turoczy Z, & Bisova K (2015) Improving microalgae for biotechnology—From genetics to synthetic biology. *Biotechnology Advances* 33:1194-1203.
106. Çelik E & Çalik P (2012) Production of recombinant proteins by yeast cells. *Biotechnology Advances* 30(5): 1108-1118.
107. de Jong A, Pietersma H, Cordes M, Kuipers O P, & Kok J (2012) PePPER: a webserver for prediction of prokaryote promoter elements and regulons. *BMC Genomics* 13:299.
108. Lee D J, Minchin S D, & Busby S J W (2012) Activating Transcription in Bacteria. *Annual review of microbiology* 66(1): 125-152.
109. Meysman P, et al. (2014) Structural Properties of Prokaryotic Promoter Regions Correlate with Functional Features. *PLoS ONE* 9(2):e88717.
110. Fujiwara T, Ohnuma M, Yoshida M, Kuroiwa T, & Hirano T (2013) Gene Targeting in the Red Alga *Cyanidioschyzon merolae*: Single- and Multi-Copy Insertion Using Authentic and Chimeric Selection Markers. *PLoS ONE* 8(9):e73608.
111. Mikami K, Hirata K, Takahashi M, Uji T, & Saga N (2011) Transient transformation of red algal cells: Breakthrough toward genetic transformation of marine crop porphyra species. Genetic Transformation, ed Alvarez M (InTech).
112. Manuell A L, et al. (2007) Robust expression of a bioactive mammalian protein in *Chlamydomonas* chloroplast. Plant biotechnology journal 5(3):402-412.
113. Cui Y, Qin S, & Jiang P (2014) Chloroplast Transformation of Platymonas (*Tetraselmis*) subcordiformis with the bar Gene as Selectable Marker. *PLoS ONE* 9(6): e98607.
114. Oey M, et al. (2013) RNAi Knock-Down of LHCBM1, 2 and 3 Increases Photosynthetic $H_2$ Production Efficiency of the Green Alga *Chlamydomonas reinhardtii*. *PLoS ONE* 8(4): e61375.
115. Oey M, Ross I L, & Hankamer B (2014) Gateway-Assisted Vector Construction to Facilitate Expression of Foreign Proteins in the Chloroplast of Single Celled Algae. *PLoS ONE* 9(2):e86841.
116. Wang B, Wang J, Zhang W, & Meldrum D R (2012) Application of synthetic biology in cyanobacteria and algae. *Frontiers in microbiology* 3:344.
117. Wang J, Jiang P, Cui Y, Guan X, & Qin S (2010) Gene transfer into conchospores of *Porphyra haitanensis* (Bangiales, Rhodophyta) by glass bead agitation. *Phycologia* 49(4):355-360.
118. Hatzfeld Y (2014) U.S. Pat. No. 8,779,237.
119. Franklin S, Somanchi A, Espina K, Rudenko G, & Chua P (2014) U.S. Pat. No. 8,674,180.
120. Feng P C C, Malven M, & Flasinski S (2013) U.S. Pat. No. 8,420,888.
121. Manjunath S, et al. (2012) U.S. Pat. No. 8,138,393.
122. Lee D W, et al. (2008) *Arabidopsis* Nuclear-Encoded Plastid Transit Peptides Contain Multiple Sequence Subgroups with Distinctive Chloroplast-Targeting Sequence Motifs. The Plant cell 20(6): 1603-1622.
123. von Heijne G, et al. (1991) CHLPEP: a database of chloroplast transit peptides. *Plant Mol Biol Rep* 9:104-126.
124. Waller R F, Reed M B, Cowman A F, & McFadden G I (2000) Protein trafficking to the plastid of *Plasmodium falciparum* is via the secretory pathway. *The EMBO Journal* 19(8): 1794-1802.
125. Minge M A, et al. (2010) A phylogenetic mosaic plastid proteome and unusual plastid-targeting signals in the green-colored dinoflagellate *Lepidodinium chlorophorum*. *BMC Evolutionary Biology* 10(1): 1-11.
126. Li H-m & Teng Y-S (2013) Transit peptide design and plastid import regulation. *Trends in Plant Science* 18(7): 360-366.
127. Tardif M, et al. (2012) PredAlgo: A New Subcellular Localization Prediction Tool Dedicated to Green Algae. *Molecular Biology and Evolution* 29(12):3625-3639.

128. Rasala B A, et al. (2010) Production of therapeutic proteins in algae, analysis of expression of seven human proteins in the chloroplast of *Chlamydomonas reinhardtii*. *Plant biotechnology journal* 8(6):719-733.

129. Doetsch N A, Favreau M R, Kuscuoglu N, Thompson M D, & Hallick R B (2001) Chloroplast transformation in *Euglena gracilis*: splicing of a group III twintron transcribed from a transgenic psbK operon. *Current genetics* 39(1):49-60.

130. Lapidot M, Raveh D, Sivan A, Arad S M, & Shapira M (2002) Stable chloroplast transformation of the unicellular red alga Porphyridium species. *Plant Physiol* 129(1): 7-12.

131. Ausubel F M, et al. (1995) *Current Protocols in Molecular Biology* (Greene Publishing and Wiley-Interscience, New York).

132. Chan H W & Wells R D (1974) Structural uniqueness of lactose operator. *Nature* 252:205-209.

133. Goeddel D V, et al. (1980) Synthesis of human fibroblast interferon by *E. coli Nucleic Acids Research* 8:4057-4074.

134. Marx C J & Lidstrom M E (2001) Development of improved versatile broad-host-range vectors for use in methylotrophs and other Gram-negative bacteria. *Microbiology* 147:2065-2075.

135. Atomi H, Imanaka T, & Fukui T (2012) Overview of the genetic tools in the Archaea. *Frontiers in microbiology* 3:337.

136. Farkas J A, Picking J W, & Santangelo T J (2013) Genetic techniques for the archaea. *Annu Rev Genet* 47:539-561.

137. Tan S (2001) A modular polycistronic expression system for overexpressing protein complexes in *Escherichia coli*. Protein expression and purification 21(1):224-234.

138. Tan S, Kern R C, & Selleck W (2005) The pST44 polycistronic expression system for producing protein complexes in *Escherichia coli*. Protein expression and purification 40(2):385-395.

139. Baba T, et al. (2006) Construction of *Escherichia coli* K-12 in-frame, single-gene knockout mutants: the Keio collection. Molecular Systems Biology 2:2006.0008-2006.0008.

140. Reyrat J M, Pelicic V, Gicquel B, & Rappuoli R (1998) Counterselectable markers: untapped tools for bacterial genetics and pathogenesis. *Infection and immunity* 66(9): 4011-4017.

141. Nakashima N & Miyazaki K (2014) Bacterial cellular engineering by genome editing and gene silencing. *International journal of molecular sciences* 15(2):2773-2793.

142. Ried J L & Collmer A (1987) An nptI-sacB-sacR cartridge for constructing directed, unmarked mutations in gram-negative bacteria by marker exchange-eviction mutagenesis. *Gene* 57(2-3):239-246.

143. Murphy K C, Campellone K G, & Poteete A R (2000) PCR-mediated gene replacement in *Escherichia coli*. *Gene* 246(1-2):321-330.

144. Sun W, Wang S, & Curtiss R (2008) Highly efficient method for introducing successive multiple scarless gene deletions and markerless gene insertions into the *Yersinia pestis* chromosome. *Appl Environ Microbiol* 74:4241-4245.

145. Costantino N & Court D L (2003) Enhanced levels of λ Red-mediated recombinants in mismatch repair mutants. *Proceedings of the National Academy of Sciences* 100(26):15748-15753.

146. Datsenko K A & Wanner B L (2000) One-step inactivation of chromosomal genes in *Escherichia coli* K-12 using PCR products. *Proceedings of the National Academy of Sciences* 97(12): 6640-6645.

147. Lv L, Ren Y-L, Chen J-C, Wu Q, & Chen G-Q (2015) Application of CRISPRi for prokaryotic metabolic engineering involving multiple genes, a case study: Controllable P (3H B-co-4H B) biosynthesis. *Metabolic Engineering* 29:160-168.

148. Peters J M, et al. (2015) Bacterial CRISPR: accomplishments and prospects. *Current opinion in microbiology* 27:121-126.

149. Selle K & Barrangou R (2015) Harnessing CRISPR-Cas systems for bacterial genome editing. *Trends in Microbiology* 23(4):225-232.

150. Rehnstam-Holm A-S & Godhe A (2003) Genetic engineering of algal species. Biotechnology, ed Doelle H W (UNESCO, Eolss Publishers, Oxford, UK).

151. Rosa L, Galván-Cejudo A, & Fernández E eds (2007) *Transgenic Microalgae as Green Cell Factories* (Springer Science+Business Media, LLC, New York, N.Y.), Vol 616.

152. Leon R & Fernandez E (2007) Nuclear transformation of eukaryotic microalgae: historical overview, achievements and problems. *Adv Exp Med Biol* 616:1-11.

153. Mikami K, Hirata R, Takahashi M, Uji T, & Saga N (2011) Transient Transformation of Red Algal Cells: Breakthrough Toward Genetic Transformation of Marine Crop Porphyra Species. *Genetic Transformation*, ed Alvarez M (InTech).

154. Umen J G & Olson B J (2012) Genomics of Volvocine Algae. *Advances in botanical research* 64:185-243.

155. Liu L, et al. (2013) Development of a new method for genetic transformation of the green alga *Chlorella ellipsoidea*. *Molecular biotechnology* 54(2):211-219.

156. Gimpel J A, Specht E A, Georgianna D R, & Mayfield S P (2013) Advances in microalgae engineering and synthetic biology applications for biofuel production. *Current opinion in chemical biology* 17(3):489-495.

157. Rasala B A, Chao S-S, Pier M, Barrera D J, & Mayfield S P (2014) Enhanced genetic tools for engineering multigene traits into green algae. *PLoS ONE*.

158. Potvin G & Zhang Z (2010) Strategies for high-level recombinant protein expression in transgenic microalgae: a review. *Biotechnol Adv* 28(6):910-918.

159. León-Bañares R, Gonzàlez-Ballester D, Galván A, & Fernández E (2004) Transgenic microalgae as green cell-factories. *Trends in Biotechnology* 22(1):45-52.

160. Heitzer M & Zschoernig B (2007) Construction of modular tandem expression vectors for the green alga *Chlamydomonas reinhardtii* using the Cre/lox-system. *Biotechniques* 43(3):324, 326, 328 passim.

161. Sizova I, Greiner A, Awasthi M, Kateriya S, & Hegemann P (2013) Nuclear gene targeting in *Chlamydomonas* using engineered zinc-finger nucleases. *The Plant Journal* 73(5): 873-882.

162. Daboussi F, et al. (2014) Genome engineering empowers the diatom *Phaeodactylum tricornutum* for biotechnology. *Nat Commun* 5.

163. Romanos M A, Scorer C A, & Clare J J (1992) Foreign gene expression in yeast: a review. *Yeast* (Chichester, England) 8(6):423-488.

164. Agmon N, et al. (2015) Yeast Golden Gate (yGG) for the Efficient Assembly of *S. cerevisiae* Transcription Units. *ACS Synthetic Biology* 4(7):853-859.

165. Sherman F (1991) Getting started with yeast. *Methods in Enzymology, Guide to Yeast Genetics and Molecular Biology*, eds Guthrie C & Fink G R (Acad. Press, New York), Vol 194, pp 3-21.
166. Sherman F, Fink G R, & Hick J B (1982) *Methods in Yeast Genetics* (Cold Spring Harbor Laboratory, New York).
167. Olmedo-Monfil V, CortÈs-Penagos C, & Herrera-Estrella A (2004) Three Decades of Fungal Transformation.), Vol 267, pp 297-313.
168. Weld R J, Plummer K M, Carpenter M A, & Ridgway H J (2006) Approaches to functional genomics in filamentous fungi. *Cell Res* 16(1):31-44.
169. Kawai S, Hashimoto W, & Murata K (2010) Transformation of *Saccharomyces cerevisiae* and other fungi: Methods and possible underlying mechanism. *Bioengineered Bugs* 1(6):395-403.
170. van den Berg M A & Maruthachalam K eds (2015) *Genetic Transformation Systems in Fungi*, Volume 1 (Springer, New York, N.Y.).
171. Rivera A L, Magana-Ortiz D, Gomez-Lim M, Fernandez F, & Loske A M (2014) Physical methods for genetic transformation of fungi and yeast. *Physics of life reviews* 11(2): 184-203.
172. Vickers C E, Bydder S F, Zhou Y, & Nielsen L K (2013) Dual gene expression cassette vectors with antibiotic selection markers for engineering in *Saccharomyces cerevisiae*. *Microbial Cell Factories* 12(1): 1-11.
173. Sherman F (1997) Yeast genetics. *The Encyclopedia of Molecular Biology and Molecular Medicine*, ed Meyers R A (VCH Publisher, Weinheim, Germany), Vol 6, pp 302-325.
174. Romanos M A, Scorer C A, & Clare J J (1992) Foreign gene expression in yeast: a review. *Yeast* (Chichester, England) 8.
175. Baudin A, Ozier-Kalogeropoulos O, Denouel A, Lacroute F, & Cullin C (1993) A simple and efficient method for direct gene deletion in *Saccharomyces cerevisiae*. *Nucleic Acids Research* 21 (14): 3329-3330.
176. Longtine M S, et al. (1998) Additional modules for versatile and economical PCR-based gene deletion and modification in *Saccharomyces cerevisiae*. Yeast (Chichester, England) 14(10):953-961.
177. Krawchuk M D & Wahls W P (1999) High-efficiency gene targeting in *Schizosaccharomyces pombe* using a modular, PCR-based approach with long tracts of flanking homology. Yeast (Chichester, England) 15(13): 1419-1427.
178. Epinat J-C, et al. (2003) A novel engineered meganuclease induces homologous recombination in yeast and mammalian cells. *Nucleic Acids Research* 31(11):2952-2962.
179. Li T, et al. (2011) Modularly assembled designer TAL effector nucleases for targeted gene knockout and gene replacement in eukaryotes. *Nucleic Acids Research*.
180. DiCarlo J E, et al. (2013) Genome engineering in *Saccharomyces cerevisiae* using CRISPR-Cas systems. *Nucleic Acids Research*.
181. Jacobs J Z, Ciccaglione K M, Tournier V, & Zaratiegui M (2014) Implementation of the CRISPR-Cas9 system in fission yeast. *Nat Commun* 5.
182. Newman T C, Ohme-Takagi M, Taylor C B, & Green P J (1993) DST sequences, highly conserved among plant SAUR genes, target reporter transcripts for rapid decay in tobacco. *The Plant cell* 5(6):701-714.
183. Ohme-Takagi M, Taylor C B, Newman T C, & Green P J (1993) The effect of sequences with high AU content on mRNA stability in tobacco. *Proceedings of the National Academy of Sciences of the United States of America* 90(24): 11811-11815.
184. Ingelbrecht I L, Herman L M, Dekeyser R A, Van Montagu M C, & Depicker A G (1989) Different 3' end regions strongly influence the level of gene expression in plant cells. *The Plant cell* 1:671-680.
185. Zaret K S & Sherman F (1982) DNA sequence required for efficient transcrition termination in yeast. *Cell* 28:563-573.
186. Heiden Jv, Rios A F, & Collado-Vides J (2000) Discovering regulatory elements in non-coding sequences by analysis of spaced dyads. *Nucleic Acids Research* 28(8): 1808-1818.
187. Graber J H (Variations in yeast 3′—processing <em>cis</em>-elements correlate with transcript stability. *Trends in Genetics* 19(9):473-476.
188. Wodniok S, Simon A, Glockner G, & Becker B (2007) Gain and loss of polyadenylation signals during evolution of green algae. *BMC Evolutionary Biology* 7(1):1-12.
189. Shen Y, Liu Y, Liu L, Liang C, & Li Q Q (2008) Unique Features of Nuclear mRNA Poly(A) Signals and Alternative Polyadenylation in *Chlamydomonas reinhardtii*. *Genetics* 179(1):167-176.
190. Schlackow M, et al. (2013) Genome-wide analysis of poly(A) site selection in *Schizosaccharomyces pombe*. *RNA* (New York, N.Y.) 19(12):1617-1631.
191. Yamanishi M, et al. (2013) A Genome-Wide Activity Assessment of Terminator Regions in *Saccharomyces cerevisiae* Provides a "Terminatome" Toolbox. *ACS Synthetic Biology* 2(6):337-347.
192. Chen Y-J, et al. (2013) Characterization of 582 natural and synthetic terminators and quantification of their design constraints. *Nat Meth* 10(7):659-664.
193. Leavitt J M & Alper H S (2015) Advances and current limitations in transcript-level control of gene expression. *Curr Opin Biotechnol* 34:98-104.
194. Nakai K & Kanehisa M (1991) Expert system for predicting protein localization sites in gram-negative bacteria. *Proteins: Structure, Function, and Bioinformatics* 11(2):95-110.
195. Bendtsen J D, Nielsen H, von Heijne G, & Brunak S (2004) Improved prediction of signal peptides: SignalP 3.0. *J Mol Biol* 340(4):783-795.
196. Bendtsen J D, Kiemer L, Fausboll A, & Brunak S (2005) Non-classical protein secretion in bacteria. *BMC Microbiology* 5(1):1-13.
197. Swinkels B W, Gould S J, Bodnar A G, Rachubinski R A, & Subramani S (1991) A novel, cleavable peroxisomal targeting signal at the amino-terminus of the rat 3-ketoacyl-CoA thiolase. *EMBO (European Molecular Biology Organization) Journal* 10(11):3255-3262.
198. Rusch S L & Kendall D A (1995) Protein transport via amino-terminal targeting sequences: Common themes in diverse systems. *Molecular Membrane Biology* 12(4): 295-307.
199. Soli J & Tien R (1998) Protein translocation into and across the chloroplastic envelope membranes. *Plant Molecular Biology* 38:191-207.
200. Gould S J, Keller G A, & Subramani S (1988) Identification of peroxisomal targeting signals located at the carboxy terminus of four peroxisomal proteins. *Journal of Cell Biology* 107(3):897-905.
201. Gould S J, Keller G A, Hosken N, Wilkinson J, & Subramani S (1989) A conserved tripeptide sorts proteins to peroxisomes. *Journal of Cell Biology* 108(5):1657-1664.

202. McCammon M T, McNew J A, Willy P J, & Goodman J M (1994) An internal region of the peroxisomal membrane protein PMP47 is essential for sorting to peroxisomes. *Journal of Cell Biology* 124(6):915-925.

203. Cokol M, Nair R, & Rost B (2000) Finding nuclear localization signals. *EMBO Reports* 1(5):411-415.

204. Helenius A & Aebi M (2001) Intracellular functions of N-linked glycans. *Science* 291(5512):2364-2369.

205. Emanuelsson O, Brunak S, von Heijne G, & Nielsen H (2007) Locating proteins in the cell using TargetP, SignalP and related tools. *Nature Protocols* 2(4):953-971.

206. Emanuelsson O, Nielsen H, Brunak S, & von Heijne G (2000) Predicting subcellular localization of proteins based on their N-terminal amino acid sequence. *Journal of Molecular Biology* 300(4): 1005-1016.

207. Bannai H, Tamada Y, Maruyama O, Nakai K, & Miyano S (2002) Extensive feature detection of N-terminal protein sorting signals. *Bioinformatics* 18(2):298-305.

208. Bendtsen J D, Nielsen H, von Heijne G, & Brunak S (2004) Improved prediction of signal peptides: SignalP 3.0. *Journal of Molecular Biology* 340(4):783-795.

209. Hiller K, Grote A, Scheer M, Munch R, & Jahn D (2004) PrediSi: prediction of signal peptides and their cleavage positions. *Nucleic Acids Research* 32 (Web Server issue): W375-379.

210. Bhasin M & Raghava G P (2004) ESLpred: SVM-based method for subcellular localization of eukaryotic proteins using dipeptide composition and PSI-BLAST. *Nucleic Acids Research* 32 (Web Server issue):W414-419.

211. Garg A, Bhasin M, & Raghava G P (2005) Support vector machine-based method for subcellular localization of human proteins using amino acid compositions, their order, and similarity search. *Journal of Biological Chemistry* 280(15):14427-14432.

212. Bhasin M, Garg A, & Raghava G P (2005) PSLpred: prediction of subcellular localization of bacterial proteins. *Bioinformatics* 21(10):2522-2524.

213. Hoglund A, Donnes P, Blum T, Adolph H W, & Kohlbacher 0 (2006) MultiLoc: prediction of protein subcellular localization using N-terminal targeting sequences, sequence motifs and amino acid composition. *Bioinformatics* 22(10):1158-1165.

214. Shatkay H, et al. (2007) SherLoc: high-accuracy prediction of protein subcellular localization by integrating text and protein sequence data. *Bioinformatics* 23(11): 1410-1417.

215. Emanuelsson O, Nielsen H, & von Heijne G (1999) ChloroP, a neural network-based method for predicting chloroplast transit peptides and their cleavage sites. *Protein Science* 8(5):978-984.

216. Claros M G & Vincens P (1996) Computational method to predict mitochondrially imported proteins and their targeting sequences. *European Journal of Biochemistry* 241(3):779-786.

217. Small I, Peeters N, Legeai F, & Lurin C (2004) Predotar: A tool for rapidly screening proteomes for N-terminal targeting sequences. *Proteomics* 4(6):1581-1590.

218. Kelley L A, MacCallum R M, & Sternberg M J (2000) Enhanced genome annotation using structural profiles in the program 3D-PSSM. *Journal of Molecular Biology* 299(2):499-520.

219. Hlavova M, Turoczy Z, & Bisova K (2015) Improving microalgae for biotechnology—From genetics to synthetic biology. *Biotechnology advances* 33(6 Pt 2):1194-1203.

220. Pratheesh P T, Vineetha M, & Kurup G M (2013) An Efficient Protocol for the *Agrobacterium*-mediated Genetic Transformation of Microalga *Chlamydomonas reinhardtii*. *Molecular biotechnology* 56(6):507-515.

221. Kindle K L (1998) Nuclear Transformation: Technology and Applications. *The Molecular Biology of Chloroplasts and Mitochondria in Chlamydomonas*, eds Rochaix J D, Goldschmidt-Clermont M, & Merchant S (Springer Netherlands, Dordrecht), pp 41-61.

222. Ohnuma M, Yokoyama T, Inouye T, Sekine Y, & Tanaka K (2008) Polyethylene Glycol (PEG)-Mediated Transient Gene Expression in a Red Alga, Cyanidioschyzon merolae 10D. *Plant and Cell Physiology* 49(1):117-120.

223. Shimogawara K, Fujiwara S, Grossman A, & Usuda H (1998) High-efficiency transformation of *Chlamydomonas reinhardtii* by electroporation. *Genetics* 148(4):1821-1828.

224. Hayashi M, Hirono M, & Kamiya R (2001) Recovery of flagellar dynein function in a *Chlamydomonas* actin/dynein-deficient mutant upon introduction of muscle actin by electroporation. *Cell Motility and the Cytoskeleton* 49(3):146-153.

225. van Ooijen G, Knox K, Kis K, Bouget F-Y, & Millar A J (2012) Genomic Transformation of the Picoeukaryote *Ostreococcus tauri*. *Journal of Visualized Experiments: JoVE* (65):4074.

226. Vieler A, et al. (2012) Genome, Functional Gene Annotation, and Nuclear Transformation of the Heterokont Oleaginous Alga *Nannochloropsis* oceanica CCMP1779. *PLoS Genetics* 8(11):e1003064.

227. Boynton J E, et al. (1988) Chloroplast transformation in *Chlamydomonas* with high velocity microprojectiles. *Science* 240(4858):1534-1538.

228. Apt K E, Kroth-Pancic P G, & Grossman A R (1996) Stable nuclear transformation of the diatom *Phaeodactylum tricornutum*. *Mol Gen Genet* 252(5):572-579.

229. Dunahay T G, Jarvis E E, & Roessler P G (1995) GENETIC TRANSFORMATION OF THE DIATOMS CYCLOTELLA CRYPTICA AND NAVICULA SAPROPHILA. *Journal of Phycology* 31 (6): 1004-1012.

230. Falciatore A, Casotti R, Leblanc C, Abrescia C, & Bowler C (1999) Transformation of Nonselectable Reporter Genes in Marine Diatoms. *Marine biotechnology* (New York, N.Y.) 1(3):239-251.

231. Zaslayskaia L A, Lippmeier J C, Kroth P G, Grossman A R, & Apt K E (2000) Transformation of the diatom *Phaeodactylum tricornutum* (Bacillariophyceae) with a variety of selectable marker and reporter genes. *Journal of Phycology* 36(2):379-386.

232. Dunahay T G (1993) Transformation of *Chlamydomonas reinhardtii* with silicon carbide whiskers. *Biotechniques* 15(3):452-455, 457-458, 460.

233. Te M R, Lohuis, & Miller D J (1998) Genetic transformation of dinoflagellates (Amphidinium and Symbiodinium): expression of GUS in microalgae using heterologous promoter constructs. *The Plant Journal* 13(3): 427-435.

234. Henry E C & Meints R H (Recombinant viruses as transformation vectors of marine macroalgae. *Journal of Applied Phycology* 6(2):247-253.

235. Van Etten J L & Meints R H (1999) Giant viruses infecting algae. *Annual review of microbiology* 53:447-494.

236. Kojima H & Kawata Y (2001) A mini-transposon/transposase complex as a new tool for the genetic transformation of microalgae. *Photosynthetic Microorganisms*

237. Miller J H (1992) *A short course in bacterial genetics: a laboratory manual and handbook for Escherichia coli and related bacteria* (Cold Spring Harbor Laboratory Press, Plainview, N.Y.).
238. Parekh S, Vinci V A, & Strobel R J (2000) Improvement of microbial strains and fermentation processes. *Appl Microbiol Biotechnol* 54(3):287-301.
239. Forsburg S L (2001) The art and design of genetic screens: yeast. *Nature reviews. Genetics* 2(9):659-668.
240. Flynn T, Ghirardi M L, & Seibert M (2002) Accumulation of $O_2$-tolerant phenotypes in H2-producing strains of *Chlamydomonas reinhardtii* by sequential applications of chemical mutagenesis and selection. *International Journal of Hydrogen Energy* 27(11-12):1421-1430.
241. Doan T T Y & Obbard J P (2012) Enhanced intracellular lipid in *Nannochloropsis* sp. via random mutagenesis and flow cytometric cell sorting. *Algal Research* 1(1):17-21.
242. Bernheim A G, Libis V K, Lindner A B, & Wintermute E H (2016) Phage-mediated Delivery of Targeted sRNA Constructs to Knock Down Gene Expression in *E. coli*. (109):e53618.
243. Zhang R, et al. (2014) High-Throughput Genotyping of Green Algal Mutants Reveals Random Distribution of Mutagenic Insertion Sites and Endonucleolytic Cleavage of Transforming DNA. *The Plant cell* 26(4):1398-1409.
244. Dent R M, Haglund C M, Chin B L, Kobayashi M C, & Niyogi K K (2005) Functional Genomics of Eukaryotic Photosynthesis Using Insertional Mutagenesis of *Chlamydomonas reinhardtii*. *Plant Physiology* 137(2): 545-556.
245. Colombo S L, et al. (2002) Use of the bleomycin resistance gene to generate tagged insertional mutants of *Chlamydomonas reinhardtii* that require elevated $CO_2$ for optimal growth. *Functional Plant Biology* 29(3):231-241.
246. Gonzalez-Ballester D, et al. (2011) Reverse genetics in *Chlamydomonas*: a platform for isolating insertional mutants. *Plant Methods* 7(1):1-13.
247. Kleckner N, Bender J, & Gottesman S (1991) Uses of transposons with emphasis on Tn10. *Methods Enzymol* 204:139-180.
248. Wu-Scharf D, Jeong B-r, Zhang C, & Cerutti H (2000) Transgene and Transposon Silencing in *Chlamydomonas reinhardtii* by a DEAH-Box RNA Helicase. *Science* 290 (5494): 1159-1162.
249. Casas-Mollano J A, et al. (2008) Diversification of the core RNA interference machinery in *Chlamydomonas reinhardtii* and the role of DCL1 in transposon silencing. *Genetics* 179(1):69-81.
250. Goryshin I Y, Jendrisak J, Hoffman L M, Meis R, & Reznikoff W S (2000) Insertional transposon mutagenesis by electroporation of released Tn5 transposition complexes. *Nat Biotech* 18(1):97-100.
251. Datsenko K A & Wanner B L (2000) One-step inactivation of chromosomal genes in *Escherichia coli* K-12 using PCR products. *Proceedings of the National Academy of Sciences of the United States of America* 97.
252. Zhong J, Karberg M, & Lambowitz A M (2003) Targeted and random bacterial gene disruption using a group II intron (targetron) vector containing a retrotransposition-activated selectable marker. *Nucleic Acids Research* 31(6): 1656-1664.
253. Minoda A, Sakagami R, Yagisawa F, Kuroiwa T, & Tanaka K (2004) Improvement of culture conditions and evidence for nuclear transformation by homologous recombination in a red alga, Cyanidioschyzon merolae 10D. *Plant & cell physiology* 45(6):667-671.
254. Qi Lei S, et al. (2013) Repurposing CRISPR as an RNA-Guided Platform for Sequence-Specific Control of Gene Expression. *Cell* 152(5):1173-1183.
255. Jiang W, Bikard D, Cox D, Zhang F, & Marraffini L A (2013) RNA-guided editing of bacterial genomes using CRISPR-Cas systems. *Nature biotechnology* 31(3):233-239.
256. Zhao T, Wang W, Bai X, & Qi Y (2009) Gene silencing by artificial microRNAs in *Chlamydomonas*. *The Plant Journal* 58(1):157-164.
257. Si T, HamediRad M, & Zhao H (2015) Regulatory RNA-assisted genome engineering in microorganisms. *Current opinion in biotechnology* 36:85-90.
258. Meng J, et al. (2012) A genome-wide inducible phenotypic screen identifies antisense RNA constructs silencing *Escherichia coli* essential genes. *FEMS microbiology letters* 329(1):45-53.
259. Xiao H & Zhao H (2014) Genome-wide RNAi screen reveals the E3 SUMO-protein ligase gene SIZ1 as a novel determinant of furfural tolerance in *Saccharomyces cerevisiae*. *Biotechnology for Biofuels* 7(1): 1-11.
260. Bao Z, et al. (2015) Homology-Integrated CRISPR-Cas (HI-CRISPR) System for One-Step Multigene Disruption in *Saccharomyces cerevisiae*. *ACS Synthetic Biology* 4(5): 585-594.
261. De Backer M D, et al. (2001) An antisense-based functional genomics approach for identification of genes critical for growth of *Candida albicans*. *Nat Biotech* 19(3):235-241.
262. Na D, et al. (2013) Metabolic engineering of *Escherichia coli* using synthetic small regulatory RNAs. *Nat Biotech* 31(2):170-174.
263. Ohnuma M, et al. (2009) Transient gene suppression in a red alga, Cyanidioschyzon merolae 10D. *Protoplasma* 236(1-4):107-112.
264. Molnar A, et al. (2009) Highly specific gene silencing by artificial microRNAs in the unicellular alga *Chlamydomonas reinhardtii*. *Plant J* 58:165-174.
265. Jiang H, et al. (2010) Methanotrophs: Multifunctional bacteria with promising applications in environmental bioengineering. *Biochemical Engineering Journal* 49(3): 277-288.
266. Demain A L (2007) The business of biotechnology. *Industrial Biotechnology* 3:269-283.
267. Andersen L, Sundman L-O, Inge-Britt Linden I-B, Kontro P, & Simo S O (1984) Synthesis and anticonvulsant properties of some 2-Aminoethanesulfonic acid (Taurine) derivatives. *Journal of Pharmaceutical Sciences* 73:106-108.
268. Herdeis C & Weis C E (1999) 5889183.
269. Tserng K-Y, Hachey D L, & Klein P D (1977) An improved procedure for the synthesis of glycine and taurine conjugates of bile acids. *Journal of Lipid Research* 18:404-407.
270. Fong D W & Hoots J E (1992) 5128419.
271. Seeberger S, Griffin R J, Hardcastle I R, & Golding B T (2007) A new strategy for the synthesis of taurine derivatives using the 'safety-catch' principle for the protection of sulfonic acids. *Organic and Biomolecular Chemistry* 5:132-138.
272. Suzuki M, Nakajima Y, Sato T, Shirai H, & Hanabusa K (2006) Fabrication of TiO2 using L-lysine-based organogelators as organic templates: control of the nanostructures. *Chemical Communications* (4):377-379.

273. Mikhalenko S A, Soloveva L I, & Lukyanets E A (2004) Phthalocyanines and related compounds: XXXVIII. Synthesis of symmetric taurine- and choline-substituted phthalocyanines. *Russian Journal of General Chemistry* 74:1775-1800.
274. Capone R, Blake S, Restrepo M R, Yang J, & Mayer M (2007) Designing Nanosensors Based on Charged Derivatives of Gramicidin A. *Journal of the American Chemical Society* 129:9737-9745.
275. Gupta R C, Win T, & Bittner S (2005) Taurine analogues; A new class of therapeutics: Retrospect and prospects *Current Medicinal Chemistry* 12:2021-2039.
276. Johnson B A (2008) Update on neuropharmacological treatments for alcoholism: Scientific basis and clinical findings. *Biochemical Pharmacology* 75:34-56.
277. Tambour S & Quertemont E (2007) Preclinical and clinical pharmacology of alcohol dependence. *Fundamental and Clinical Pharmacology* 21:9-28.
278. Joung Y K, Sengoku Y, Ooya T, Park K D, & Yui N (2005) Anticoagulant supramolecular-structured polymers: Synthesis and anticoagulant activity of taurine-conjugated carboxyethylester-polyrotaxanes. *Science and Technology of Advanced Materials* 6:484-490.
279. Özmeriç N, et al. (2000) Chitosan film enriched with an antioxidant agent, taurine, in fenestration defects. *Journal of Biomedical Materials Research Part A* 51:500-503.
280. Degim Z, et al. (2002) An investigation on skin wound healing in mice with a taurinechitosan gel formulation. *Amino Acids* 22:187-198.
281. Matsusaki M, Serizawa T, Kishida A, Endo T, & Akashi M (2002) Novel functional biodegradable polymer: Synthesis and anticoagulant activity of poly(γ-Glutamic Acid) sulfonate (γ-PGA-sulfonate). *Bioconjugate Chemistry* 13:23-28.
282. Roubos J A, van Straten G, & van Boxtel A J B (1999) An evolutionary strategy for fed-batch bioreactor optimization; concepts and performance. *Journal of Biotechnology* 67(2-3):173-187.
283. Oka T (1999) *Amino acids, production processes. Encyclopedia of Bioprocess Technology: Fermentation, Biocatalysis, and Bioseparation*, eds Flickinger M C & Drew S W (Wiley, London).
284. Borowitzka M A (1999) Commercial production of microalgae: ponds, tanks, tubes and fermenters. *Journal of Biotechnology* 70(1-3):313-321.
285. Hermann T (2003) Industrial production of amino acids by coryneform bacteria. *J Biotechnol* 104(1-3): 155-172.
286. Ikeda M (2003) *Amino acid production processes. Advances in biochemical engineering/biotechnology* 79:1-35.
287. Ikeda M (2005) Towards bacterial strains overproducing 1-tryptophan and other aromatics by metabolic engineering. *Applied Microbiology and Biotechnology* 69(6): 615-626.
288. Richmond A & Hu Q eds (2013) *Handbook of Microalgal Culture: Biotechnology and Applied Phycology* (Wiley-Blackwell, Hoboken, N.J.), 2nd Ed.
289. Cardozo K H, et al. (2007) Metabolites from algae with economical impact. *Comparative biochemistry and physiology. Toxicology & pharmacology: CBP* 146(1-2):60-78.
290. Milledge J J (2011) Commercial application of microalgae other than as biofuels: a brief review. *Reviews in Environmental Science and Biotechnology* 10:31-41.
291. Xu Q, Li S, Huang H, & Wen J (2012) Key technologies for the industrial production of fumaric acid by fermentation. *Biotechnology advances* 30(6):1685-1696.
292. Dufossé L, Fouillaud M, Caro Y, Mapari S A S, & Sutthiwong N (2014) Filamentous fungi are large-scale producers of pigments and colorants for the food industry. *Current Opinion in Biotechnology* 26:56-61.
293. Höfler A, et al. (1998) U.S. Pat. No. 5,840,358
294. Lee I, Lee K, Namgoong K, & Lee Y-S (2002) The use of ion exclusion chromatography as approved to the normal ion exchange chromatography to achieve a more efficient lysine recovery from fermentation broth. *Enzyme and Microbial Technology* 30(6):798-803.
295. Binder M & Uffmann K-E (2002) U.S. Pat. No. 6,465,025.
296. Leuchtenberger W, Huthmacher K, & Drauz K (2005) Biotechnological production of amino acids and derivatives: current status and prospects. *Appl Microbiol Biotechnol* 69(1): 1-8.
297. Meinkoth J & G. W (1984) Hybridization of nucleic acids immobilized on solid supports. *Analytical Biochemistry* 138:267-284.
298. Tijssen P (1993) Overview of principles of hybridization and the strategy of nucleic acid probe assays. *Laboratory Techniques in Biochemistry and Molecular Biology—Hybridization with Nucleic Acid Probes: Part I*, (Elsevier, New York).
299. Smith T F & Waterman M S (1981) Comparison of biosequences. *Advances in Applied Mathematics* 2:482-489.
300. Needleman S B & Wunsch C D (1970) A general method applicable to the search for similarities in the amino acid sequence of two proteins. *Journal of Molecular Biology* 48:443-453.
301. Pearson W R & Lipman D J (1988) *Improved tools for biological sequence comparison. Proceedings of the National Academy of Sciences of the United States of America* 85:2444-2448.
302. Higgins D G, Bleasby A J, & Fuchs R (1992) CLUSTAL V: improved software for multiple sequence alignment. *Computer Applications in the Biosciences* 8(2):189-191.
303. Higgins D G & Sharp P M (1988) CLUSTAL: a package for performing multiple sequence alignment on a microcomputer. *Gene* 73(1):237-244.
304. Higgins D G & Sharp P M (1989) Fast and sensitive multiple sequence alignments on a microcomputer. *Computer Applications in the Biosciences* 5(2):151-153.
305. Feng D F & Doolittle R F (1987) Progressive sequence alignment as a prerequisite to correct phylogenetic trees. *Journal of Molecular Evolution* 25(4):351-360.
306. Henikoff S & Henikoff J (1989) Amino acid substitution matrices from protein blocks *Proceedings of the National Academy of Sciences of the United States of America* 89:10915-10919.
307. Altschul S F, et al. (1997) Gapped BLAST and PSI-BLAST: a new generation of protein database search programs. *Nucleic Acids Research* 25:3389-3402.
308. Wootton J C & Federhen S (1993) Statistics of local complexity in amino acid sequences and sequence databases. *Computational Chemistry* 17:149-163.
309. Wootton J C & Federhen S (1996) Analysis of compositionally biased regions in sequence databases. *Methods Enzymol* 266:554-571.
310. Claverie J-M & States D J (1993) Information enhancement methods for large scale sequence analysis. *Computational Chemistry* 17:191-201.
311. Myers E W & Miller W (1988) Optimal alignments in linear-space. *Computer Applications in the Biological Sciences* 4:11-17.

312. Buchholz J, et al. (2013) Platform engineering of *Corynebacterium glutamicum* with reduced pyruvate dehydrogenase complex activity for improved production of L-lysine, L-valine, and 2-ketoisovalerate. *Appl Environ Microbiol* 79(18):5566-5575.

313. Stefan A, Schwarz F, Bressanin D, & Hochkoeppler A (2010) Shine-Dalgarno sequence enhances the efficiency of lacZ repression by artificial anti-lac antisense RNAs in *Escherichia coli*. *Journal of bioscience and bioengineering* 110(5):523-528.

314. Studier F W (2014) Stable Expression Clones and Auto-Induction for Protein Production in *E. coli*. *Structural Genomics: Methods and Protocols*, Methods in Molecular Biology, ed Chen Y W (Springer, New York).

Example 1

Development of a Transgenic Bacterium with a TauD Knockout that Expresses CDOL without Transit Peptide Fused with a Linker to partCS/PLP-DC Using Chemical Synthesis Step 1: Use PCR to amplify the TauD (SEQ ID NO:20) using 500 ng of DNA from *E. coli* strain K12 and the primers for SEQ ID NO:44 and SEQ ID NO:45. Use the PCR-amplified fragment to knockout TauD with λ Red-mediated recombination as described by Datsenko and Wanner(251) and Baba et al. (139)

Step 2: Use chemical synthesis to make a DNA construct that contains a CDOL gene (SEQ ID NO:3) without the transit peptide, linker (SEQ ID NO:15), partCS/PLP-DC gene (SEQ ID NO:11) all in frame. Clone the CDOL/linker/partCS/PLP-DC fragment into a bacterial expression vector, such as pET11, pKK223-3, or pSF-Tac, so it is functional.

The CDOL gene is as follows:
a. Derived from SEQ ID NO:3 by removing nucleotides 4 through 159 (corresponding to the native transit peptide) and without the stop codon, optimized for expression in *E. coli* and encoding a CDOL peptide from *Chlamydomonas reinhardtii* (SEQ ID NO:4 minus amino acids 2 through 53); and The partCS/PLP-DC gene is as follows:
a. Derived from SEQ ID NO:11 by removing nucleotides 1 through 1413 (corresponding to the native transit and cysteine synthetase peptides), optimized for expression in *E. coli* and encoding a partCS/PLP-DC peptide from *Micromonas pusilla* (SEQ ID NO:12 minus amino acids 1 through 471); and Step 3: Transform the vector with the functional CDOL/linker/partCS/PLP-DC construct (from Step 2, EXAMPLE 1) into the TauD knockout *E. coli* strain (from Step 1, EXAMPLE 1) and confirm the presence of the DNA construct.

Example 2

Development of a Transgenic Bacterium with a TauD Knockout that Expresses CDOL without Transit Peptide Fused with a Linker to partCS/PLP-DC and a Taurine Binding Peptide Using Chemical Synthesis Step 1: Use chemical synthesis to make a DNA construct that contains a taurine binding protein (SEQ ID NO:16 or SEQ ID NO:18) without the transit peptide. Clone the taurine binding protein into a bacterial expression vector, such as pET11, pKK223-3, or pSF-Tac, so it is functional.

The taurine-binding protein gene is as follows:
a. Derived from SEQ ID NO:16 by removing nucleotides 4 through 66 (corresponding to the periplasmic transit peptide) and encoding a truncated taurine-binding peptide from *E. coli* (SEQ ID NO:17 minus amino acids 2 through 22); or
b. Derived from SEQ ID NO:18, by removing nucleotides 4 through 93, (corresponding to the periplasmic transit peptide), optimized for expression in *E. coli* and encoding a truncated taurine-binding peptide from *Roseobacter denitrificans* (SEQ ID NO:19 minus amino acids 2 through 31);

Step 2: Transform the DNA vector with the taurine-binding protein (from Step 1, EXAMPLE 2) into the TauD knockout *E. coli* strain that contains the vector with the CDOL/linker/partCS/PLP-DC (from Step 3, EXAMPLE 1). Select for antibiotic resistance, and confirm the presence of the DNA constructs.

Example 3

Development of a Transgenic Bacterium with a Cbl Knockout that Expresses CDOL without Transit Peptide Fused with a Linker to partCS/PLP-DC Using Chemical Synthesis Step 1: Use PCR to amplify the cbl (SEQ ID NO:36) using 500 ng of DNA from *E. coli* strain K12 and the primers for SEQ ID NO:46 and SEQ ID NO:47. Use the PCR-amplified fragment to knockout cbl with λ Red-mediated recombination as described by Datsenko and Wanner(251) and Baba et al. (139)

Step 2: Transform the vector with the functional CDOL/linker/partCS/PLP-DC construct (from Step 2, EXAMPLE 1) into the cbl knockout *E. coli* strain (from Step 1, EXAMPLE 3) and confirm the presence of the DNA construct.

Example 4

Development of a Transgenic Bacterium with a Cbl Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 2) into the cbl knockout *E. coli* strain that contains the vector with the CDOL/linker/partCS/PLP-DC (from Step 2, EXAMPLE 3) and confirm the presence of the DNA constructs.

Example 5

Development of a Transgenic Bacterium with a SsuD Knockout that Expresses CDOL without Transit Peptide Fused with a Linker to partCS/PLP-DC Using Chemical Synthesis Step 1: Use PCR to amplify the SsuD (SEQ ID NO:22) using 500 ng of DNA from *E. coli* strain K12 and the primers for SEQ ID NO:48 and SEQ ID NO:49. Use the PCR-amplified fragment to knockout SsuD with λ Red-mediated recombination as described by Datsenko and Wanner(251) and Baba et al. (139)

Step 2: Transform the vector with the functional CDOL/linker/partCS/PLP-DC construct (from Step 2, EXAMPLE 1) into the SsuD knockout *E. coli* strain (from Step 1, EXAMPLE 5) and confirm the presence of the DNA construct.

Example 6

Development of a Transgenic Bacterium with a SsuD Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 2) into the SsuD knockout *E. coli* strain that contains the vector with the CDOL/linker/partCS/PLP-DC (from Step 2, EXAMPLE 5) and confirm the presence of the DNA constructs.

Example 7

Development of a Transgenic Bacterium with a SsuE Knockout that Expresses CDOL without Transit Peptide Fused with a Linker to partCS/PLP-DC Using Chemical Synthesis Step 1: Use PCR to amplify the SsuE (SEQ ID NO:24) using 500 ng of DNA from *E. coli* strain K12 and the primers for SEQ ID NO:50 and SEQ ID NO:51. Use the PCR-amplified fragment to knockout SsuE with λ Red-mediated recombination as described by Datsenko and Wanner (251) and Baba et al. (139)

Step 2: Transform the vector with the functional CDOL/Linker/partCS/PLP-DC construct (from Step 2, EXAMPLE 1) into the SsuE knockout *E. coli* strain (from Step 1, EXAMPLE 7) and confirm the presence of the DNA construct.

Example 8

Development of a Transgenic Bacterium with a SsuE Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 2) into the SsuE knockout *E. coli* strain that contains the vector with the CDOL/linker/partCS/PLP-DC (from Step 2, EXAMPLE 7) and confirm the presence of the DNA constructs.

Example 9

Development of Another Type of Transgenic Bacterium with a SsuD Knockout that Expresses CDOL without Transit Peptide Fused with a Linker to partCS/PLP-DC Using Chemical Synthesis Step 1: Use overlap PCR to amplify a knockout fragment for SsuD (SEQ ID NO:26) using genome DNA from *Corynebacterium glutamicum* and the pK19mobsacB vector as described by Buchholz et al.(312) Generate independent DNA fragments using the primer pairs SEQ ID NO:52 and SEQ ID NO:53 and genome DNA from *C. glutamicum* and SEQ ID NO:54 and SEQ ID NO:55 and genome DNA from *C. glutamicum*. Purify each DNA fragment and mix in equal amounts in an overlap PCR using primers SEQ ID NO:52 and SEQ ID NO:55. Clone the resulting fusion product containing the SsuD gene with an internal deletion of 875 bp (SsuD knockout fragment) into pK19mobsacB. Replace the SsuD1 gene with the SsuD knockout fragment by homologous recombination.(312)

Step 2: Use chemical synthesis to make a DNA construct that contains a CDOL gene (SEQ ID NO:3) without the transit peptide, linker (SEQ ID NO:15), partCS/PLP-DC gene (SEQ ID NO:11) all in frame. Clone the CDOL/linker/partCS/PLP-DC fragment into a bacterial expression vector, such as pET11, pKK223-3, or pSF-Tac, so it is functional.

The CDOL gene is as follows:
a. Derived from SEQ ID NO:3 by removing nucleotides 4 through 159 (corresponding to the native transit peptide) and without the stop codon, optimized for expression in *C. glutamicum* and encoding a CDOL peptide from *Chlamydomonas reinhardtii* (SEQ ID NO:4 minus amino acids 2 through 53); and The partCS/PLP-DC gene is as follows:
a. Derived from SEQ ID NO:11 by removing nucleotides 1 through 1413 (corresponding to the native transit and cysteine synthetase peptides), optimized for expression in *C. glutamicum* and encoding a partCS/PLP-DC peptide from *Micromonas pusilla* (SEQ ID NO:12 minus amino acids 1 through 471); and Step 3: Transform the vector with the functional CDOL/linker/partCS/PLP-DC construct (from Step 2, EXAMPLE 9) into the SsuD knockout *C. glutamicum* strain (from Step 1, EXAMPLE 9) and confirm the presence of the DNA construct.

Example 10

Development of Another Type of Transgenic Bacterium with a SsuD Knockout that Expresses CDOL without Transit Peptide Fused with a Linker to partCS/PLP-DC and a Taurine Binding Peptide Using Chemical Synthesis Step 1: Use chemical synthesis to make a DNA construct that contains a taurine binding protein (SEQ ID NO:16 or SEQ ID NO:18) without the transit peptide. Clone the taurine binding protein into a bacterial expression vector, such as pET11, pKK223-3, or pSF-Tac, so it is functional.

The taurine binding protein gene is as follows:
a. Derived from SEQ ID NO:16 by removing nucleotides 4 through 66 (corresponding to the periplasmic transit peptide) and encoding a truncated taurine-binding peptide from *C. glutamicum* (SEQ ID NO:17 minus amino acids 2 through 22); or
b. Derived from SEQ ID NO:18 by removing nucleotides 4 through 93, (corresponding to the periplasmic transit peptide), optimized for expression in *C. glutamicum* and encoding a truncated taurine-binding peptide from *Roseobacter denitrificans* (SEQ ID NO:19 minus amino acids 2 through 31);

Step 2: Transform the DNA vector with the taurine-binding protein (from Step 1, EXAMPLE 10) into the SsuD knockout *C. glutamicum* strain (from Step 1, EXAMPLE 9) and confirm the presence of the DNA construct.

Example 11

Development of Another Type of Transgenic Bacterium with a SsuE Knockout that Expresses CDOL without Transit Peptide Fused with a Linker to partCS/PLP-DC Using Chemical Synthesis Step 1: Use overlap PCR to amplify a knockout fragment for SsuE (SEQ ID NO:28) using genome DNA from

*Corynebacterium glutamicum* and the pK19mobsacB vector as described by Buchholz et al. (312) Generate independent DNA fragments using the primer pairs SEQ ID NO:56 and SEQ ID NO:57 and genome DNA from *C. glutamicum* and SEQ ID NO:58 and SEQ ID NO:59 and genome DNA from *C. glutamicum*. Purify each DNA fragment and mix in equal amounts in an overlap PCR using primers SEQ ID NO:56 and SEQ ID NO:59. Clone the resulting fusion product, containing the SsuE gene with an internal deletion of 735 bp (SsuE knockout fragment), into pK19mobsacB. Replace the SsuE gene with the SsuE knockout fragment by homologous recombination. (312)

Step 2: Transform the vector with the functional CDOL/linker/partCS/PLP-DC construct (from Step 2, EXAMPLE 9) into the SsuE knockout *C. glutamicum* strain (from Step 1, EXAMPLE 11) and confirm the presence of the DNA construct.

Example 12

Development of Another Transgenic Bacterium with a SsuE Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 10) into the SsuE knockout *C. glutamicum* strain (from Step 1, EXAMPLE 11) and confirm the presence of the DNA construct.

Example 13

Development of Another Transgenic Bacterium with a Cbl Knockout that Expresses CDOL without Transit Peptide Fused with a Linker to partCS/PLP-DC Using Chemical Synthesis Step 1: Use overlap PCR to amplify a knockout fragment for cbl (SEQ ID NO:38) using genome DNA from *Corynebacterium glutamicum*, and the pK19mobsacB vector as described by Buchholz et al. (312) Generate independent DNA fragments using the primer pairs SEQ ID NO:60 and SEQ ID NO:61 and genome DNA from *C. glutamicum* and SEQ ID NO:62 and SEQ ID NO:63 and genome DNA from *C. glutamicum*. Purify each DNA fragment and mix in equal amounts in an overlap PCR using primers SEQ ID NO:60 and SEQ ID NO:63. Clone the resulting fusion product, containing the cbl gene with an internal deletion of 563 bp (cbl knockout fragment) into pK19mobsacB. Replace the cbl gene with the cbl knockout fragment by homologous recombination. (312)

Step 2: Transform the vector with the functional CDOL/linker/partCS/PLP-DC construct (from Step 2, EXAMPLE 9) into the cbl knockout *C. glutamicum* strain (from Step 1, EXAMPLE 13) and confirm the presence of the DNA construct.

Example 14

Development of Another Transgenic Bacterium with a Cbl Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 10) into the cbl knockout *C. glutamicum* strain (from Step 1, EXAMPLE 13) and confirm the presence of the DNA construct.

Example 15

Development of a Transgenic Bacterium with a TauR Knockout that Expresses CDOL without Transit Peptide Fused with a Linker to partCS/PLP-DC Using Chemical Synthesis Step 1: Use overlap PCR to amplify a knockout fragment for TauR (SEQ ID NO:40) using genome DNA from *Corynebacterium glutamicum* and the pK19mobsacB vector as described by Buchholz et al. (312) Generate independent DNA fragments using the primer pairs SEQ ID NO:64 and SEQ ID NO:65 and genome DNA from *C. glutamicum* and SEQ ID NO:66 and SEQ ID NO:67 and genome DNA from *C. glutamicum*. Purify each DNA fragment and mix in equal amounts in an overlap PCR using primers SEQ ID NO:64 and SEQ ID NO:67. Clone the resulting fusion product, containing the TauR gene with an internal deletion of 1052 bp (TauR knockout fragment) into pK19mobsacB. Replace the TauR gene with the TauR knockout fragment by homologous recombination. (312)

Step 2: Transform the vector with the functional CDOL/linker/partCS/PLP-DC construct (from Step 2, EXAMPLE 9) into the TauR knockout *C. glutamicum* strain (from Step 1, EXAMPLE 15) and confirm the presence of the DNA construct.

Example 16

Development of a Transgenic Bacterium with a TauR Knockout that Expresses CDOL without Transit Peptide Fused with a Linker to partCS/PLP-DC and a Taurine Binding Peptide Using Chemical Synthesis Step 1: Transform the DNA vector with the taurine-binding protein (from Step 1, EXAMPLE 10) into the TauR knockout *C. glutamicum* strain (from Step 1, EXAMPLE 15) and confirm the presence of the DNA construct.

Example 17

Development of a Transgenic Alga with a Native Taurine Biosynthetic Pathway that Expresses a Taurine Binding Protein Using Chemical Synthesis Step 1: Use chemical synthesis to make a DNA construct that contains a taurine binding protein (SEQ ID NO:16 or SEQ ID NO:18) without the transit peptide. Clone the taurine binding protein into an algal expression vector, such as pCB740 or pD1-Kan, so it is functional.

The taurine binding protein gene is as follows:
 a. Derived from SEQ ID NO:16 by removing nucleotides 4 through 66 (corresponding to the periplasmic transit peptide), optimized for expression in *Chlamydomonas reinhardtii* or *Ostreococcus tauri* and encoding a truncated taurine-binding peptide from *E. coli* (SEQ ID NO:17 minus amino acids 2 through 22); or
 b. Derived from SEQ ID NO:18 by removing nucleotides 4 through 93, (corresponding to the periplasmic transit peptide), optimized for expression in *Chlamydomonas reinhardtii* or *Ostreococcus tauri* and encoding a truncated taurine-binding protein from *Roseobacter denitrificans* (SEQ ID NO:19 minus amino acids 2 through 31);

Step 2: Transform the DNA vector with the taurine-binding protein (from Step 1, EXAMPLE 17) into *Chlamydomonas reinhardtii* or *Ostreococcus tauri* and confirm the presence of the DNA constructs.

Example 18

Development of a Transgenic Alga with a Native Taurine Biosynthetic Pathway that Expresses a Taurine Binding Protein with a Chloroplast Transit Peptide Using Chemical Synthesis Step 1: Use chemical synthesis to make a DNA construct that contains a taurine binding protein (SEQ ID NO:16 or SEQ ID NO:18) with the plastid transit peptide (SEQ ID NO:13). Clone the taurine-binding protein into an algal expression vector, such as pCB740 or pD1-Kan, so it is functional.

The nucleotide sequence for the plastid transit peptide (SEQ ID NO:13) encodes the peptide SEQ ID NO:14.

The taurine binding protein gene is as follows:
a. Derived from SEQ ID NO:16 by removing nucleotides 1 through 66 (corresponding to the periplasmic transit peptide), optimized for expression in *Chlamydomonas reinhardtii* or *Ostreococcus tauri* and encoding a truncated taurine-binding peptide from *E. coli* (SEQ ID NO:17 minus amino acids 1 through 22); or
b. Derived from SEQ ID NO:18 by removing nucleotides 4 through 93, (corresponding to the periplasmic transit peptide), optimized for expression in *Chlamydomonas reinhardtii* or *Ostreococcus tauri* and encoding a truncated taurine-binding peptide from *Roseobacter denitrificans* (SEQ ID NO:19 minus amino acids 2 through 31);

Step 2: Transform the DNA vector with the taurine-binding protein (from Step 1, EXAMPLE 18) into *Chlamydomonas reinhardtii* or *Ostreococcus tauri* and confirm the presence of the DNA constructs.

Example 19

Development of a Transgenic Alga with a Native Taurine Biosynthetic Pathway that Expresses a Taurine Binding Protein in the Chloroplast Via Chloroplast Transformation Using Chemical Synthesis Step 1: Make the following construct: an atpA promoter-59UTR (untranslated region) operably linked to taurine binding protein and the atpA terminator (TatpA). Use the chloroplast destination expression for *Chlamydomonas reinhardtii* as described by Oey et al (115) Use chemical synthesis to make a DNA construct that contains a taurine binding protein (SEQ ID NO:16 or SEQ ID NO:18) without a transit peptide with XbaI at the 5' end and a NcoI site at the 3' end. Clone the taurine-binding protein into the XbaI/NcoI site (remove the GFP fragment) of the Entry vector. Recombine the atpA/taurine binding protein/atpA cassette from the Entry vector into the Destination vector, pC-Dest/psbA.

The taurine binding protein gene is as follows:
a. Derived from SEQ ID NO:16 by removing nucleotides 4 through 66 (corresponding to the periplasmic transit peptide), optimized for expression in *Chlamydomonas reinhardtii* and encoding a truncated taurine-binding peptide from *E. coli* (SEQ ID NO:17 minus amino acids 2 through 22) with an XbaI site 5' of the start codon and a NcoI site 3' of the stop codon; or
b. Derived from SEQ ID NO:18 by removing nucleotides 4 through 93, (corresponding to the periplasmic transit peptide), optimized for expression in *Chlamydomonas reinhardtii* and encoding a truncated taurine-binding peptide from *Roseobacter denitrificans* (SEQ ID NO:19 minus amino acids 2 through 31) with an XbaI site 5' of the start codon and a NcoI site 3' of the stop codon;

Step 2: Transform the DNA vector with the Destination vector containing the atpA promoter/taurine binding protein/TatpA (from Step 1, EXAMPLE 19) into *Chlamydomonas reinhardtii* and confirm the presence of the DNA construct.

Example 20

Development of a Transgenic Fungus that Expresses CDOL without the Transit Peptide Fused with a Linker to partCS/PLP-DC and a Taurine Binding Protein Using Chemical Synthesis Step 1: Use chemical synthesis to make a DNA construct that contains a CDOL gene (SEQ ID NO:3) without the transit peptide, linker (SEQ ID NO:15), partCS/PLP-DC gene (SEQ ID NO:11) all in frame. Clone the CDOL/linker/partCS/PLP-DC fragment into a fungal expression vector so it is functional.

The CDOL gene is as follows:
a. Derived from SEQ ID NO:3 by removing nucleotides 4 through 159 (corresponding to the native transit peptide) and without the stop codon, optimized for expression in yeast and encoding a CDOL peptide from *Chlamydomonas reinhardtii* (SEQ ID NO:4 minus amino acids 2 through 53); and The partCS/PLP-DC gene is as follows:
a. Derived from SEQ ID NO:11 by removing nucleotides 1 through 1413 (corresponding to the native transit and cysteine synthetase peptides), optimized for expression in yeast and encoding a partCS/PLP-DC peptide from *Micromonas pusilla* (SEQ ID NO:12 minus amino acids 1 through 471); and Step 3: Transform the vector with the functional CDOL/linker/partCS/PLP-DC construct (from Step 2, EXAMPLE 20) into yeast and confirm the presence of the DNA construct.

Step 4: Use chemical synthesis to make a DNA construct that contains a taurine-binding protein (SEQ ID NO:16 or SEQ ID NO:18) without the transit peptide. Clone the taurine-binding protein into a fungal expression vector, such as pESC-TRP, pYES2/NT, or pYSG-IBA, so it is functional.

The taurine-binding protein gene is as follows:
a. Derived from SEQ ID NO:16 by removing nucleotides 4 through 66 (corresponding to the periplasmic transit peptide), optimized for expression in yeast, and encoding a truncated taurine-binding protein (SEQ ID NO:17 minus amino acids 2 through 22); or
b. Derived from SEQ ID NO:18, by removing nucleotides 4 through 93, (corresponding to the periplasmic transit peptide), optimized for expression in yeast and encoding a truncated taurine-binding protein from *Roseobacter denitrificans* (SEQ ID NO:19 minus amino acids 2 through 31);

Step 4: Transform the DNA vector with the taurine-binding protein (from Step 3, EXAMPLE 20) into the yeast strain that contains the vector with the CDOL/linker/partCS/PLP-DC (from Step 3, EXAMPLE 20) and confirm the presence of the DNA constructs.

Example 21

Development of a Transgenic Fungus that Expresses CS/PLP-DC without the Transit Peptide and a Taurine Binding Protein Using Chemical Synthesis Step 1: Use chemical synthesis to make a DNA construct that contains a CS/PLP-DC gene (SEQ ID NO:11) without the transit peptide. Clone the CS/PLP-DC fragment into a fungal expression vector, such as pESC-TRP, pYES2/NT, or pYSG-IBA vector, so it is functional.

The CS/PLP-DC gene is as follows:

a. Derived from SEQ ID NO:11, by removing nucleotides 4 through 234, (corresponding to the native transit peptide) optimized for expression in yeast, and encoding a CS/PLP-DC peptide from *Micromonas pusilla* (SEQ ID NO:12 minus amino acids 2 through 78); and Step 2: Transform the vector with the functional CS/PLP-DC construct (from Step 1, EXAMPLE 21) into yeast and confirm the presence of the DNA construct.

Step 3: Use chemical synthesis to make a DNA construct that contains a taurine-binding protein (SEQ ID NO:16 or SEQ ID NO:18) without the transit peptide. Clone the taurine-binding protein into a fungal expression vector, such as pESC-TRP, pYES2/NT, or pYSG-IBA, so it is functional.

The taurine-binding protein gene is as follows:

a. Derived from SEQ ID NO:16 by removing nucleotides 4 through 66 (corresponding to the periplasmic transit peptide), optimized for expression in yeast, and encoding a truncated taurine-binding peptide (SEQ ID NO:17 minus amino acids 2 through 22); or b. Derived from SEQ ID NO:18, by removing nucleotides 4 through 93, (corresponding to the periplasmic transit peptide), optimized for expression in yeast, and encoding a truncated taurine-binding peptide from *Roseobacter denitrificans* (SEQ ID NO:19 minus amino acids 2 through 31);

Step 4: Transform the DNA vector with the taurine-binding protein (from Step 3, EXAMPLE 21) into the yeast strain that contains the vector with the CS/PLP-DC (from Step 2, EXAMPLE 21) and confirm the presence of the DNA constructs.

Example 22

Development of a Transgenic Fungus with that Expresses CDO without the Transit Peptide Fused with a Linker SAD and a Taurine Binding Protein Using Chemical Synthesis Step 1: Use chemical synthesis to make a DNA construct that contains a CDO gene (SEQ ID NO:1) without the transit peptide, linker (SEQ ID NO:15), SAD gene (SEQ ID NO:5) all in frame. Clone the CDO/linker/SAD fragment into a fungal expression vector so it is functional.

The CDO gene is as follows:

a. Derived from SEQ ID NO:1 without the stop codon, optimized for expression in yeast and encoding a CDO peptide from *Danio rerio* (SEQ ID NO:2); and The SAD gene is as follows:

a. Derived from SEQ ID NO:5 optimized for expression in yeast and encoding a SAD peptide from *Danio rerio* (SEQ ID NO:6); and Step 3: Transform the vector with the functional CDO/linker/SAD construct (from Step 1, EXAMPLE 22) into yeast and confirm the presence of the DNA construct.

Step 4: Use chemical synthesis to make a DNA construct that contains a taurine-binding protein (SEQ ID NO:16 or SEQ ID NO:18) without the transit peptide. Clone the taurine-binding protein into a fungal expression vector, such as pESC-TRP, pYES2/NT, or pYSG-IBA, so it is functional.

The taurine-binding protein gene is as follows:

a. Derived from SEQ ID NO:16 by removing nucleotides 4 through 66 (corresponding to the periplasmic transit peptide), optimized for expression in yeast, and encoding a truncated taurine-binding protein (SEQ ID NO:17 minus amino acids 2 through 22); or b. Derived from SEQ ID NO:18, by removing nucleotides 4 through 93, (corresponding to the periplasmic transit peptide), optimized for expression in yeast, and encoding a truncated taurine-binding protein from *Roseobacter denitrificans* (SEQ ID NO:19 minus amino acids 2 through 31);

Step 4: Transform the DNA vector with the taurine-binding protein (from Step 3, EXAMPLE 20) into the yeast strain that contains the vector with the CDO/linker/SAD (from Step 3, EXAMPLE 22) and confirm the presence of the DNA constructs.

Example 23

Development of a Transgenic Fungus that Expresses CDOL without the Transit Peptide Fused with a Linker GADL1 and a Taurine Binding Protein Using Chemical Synthesis Step 1: Use chemical synthesis to make a DNA construct that contains a CDOL gene (SEQ ID NO:3) without the transit peptide, linker (SEQ ID NO:15), GADL1 gene (SEQ ID NO:9) all in-frame. Clone the CDOL/linker/GADL1 fragment into a fungal expression vector so it is functional.

The CDOL gene is as follows:

a. Derived from SEQ ID NO:3 by removing nucleotides 4 through 159 (corresponding to the native transit peptide) and without the stop codon, optimized for expression in *E. coli* and encoding a CDOL peptide from *Chlamydomonas reinhardtii* (SEQ ID NO:4 minus amino acids 2 through 53); and The GADL1 gene is as follows:

a. Derived from SEQ ID NO:9 optimized for expression in yeast and encoding a GADL1 peptide from *Danio rerio* (SEQ ID NO:10); and Step 3: Transform the vector with the functional CDOL/linker/GADL1 construct (from Step 1, EXAMPLE 23) into yeast and confirm the presence of the DNA construct.

Step 4: Use chemical synthesis to make a DNA construct that contains a taurine-binding protein (SEQ ID NO:16 or SEQ ID NO:18) without the transit peptide. Clone the taurine-binding protein into a fungal expression vector, such as pESC-TRP, pYES2/NT, or pYSG-IBA, so it is functional.

The taurine-binding protein gene is as follows:

a. Derived from SEQ ID NO:16 by removing nucleotides 4 through 66 (corresponding to the periplasmic transit peptide), optimized for expression in yeast, and encoding a truncated taurine-binding protein (SEQ ID NO:17 minus amino acids 2 through 22); or b. Derived from SEQ ID NO:18, by removing nucleotides 4 through 93, (corresponding to the periplasmic transit peptide), optimized for expression in yeast, and encoding a truncated taurine-binding protein from *Roseobacter denitrificans* (SEQ ID NO:19 minus amino acids 2 through 31);

Step 4: Transform the DNA vector with the taurine-binding protein (from Step 3, EXAMPLE 23) into the yeast strain that contains the vector with the CDO/linker/GADL1 (from Step 3, EXAMPLE 22) and confirm the presence of the DNA constructs.

Example 24

Development of a Transgenic Bacterium with TauX Suppressed that Expresses CDOL without the Transit Peptide Fused with a Linker to partCS/PLP-DC Using Chemical Synthesis Step 1: Use chemical synthesis to make an antisense construct to silence or suppress TauX (SEQ ID NO: 30) and clone into the pBAD vector as described by Stefan et al. (313)

The TauX antisense is as follows:

a. Fuse the polynucleotides for SEQ ID NO:68 to polynucleotides 1 through 360 of SEQ ID NO:30. Clone the TauX antisense fragment into the bacterial expression vector, pBAD so TauX antisense fragment can be expressed.

Step 2: Transform the vector with the TauX antisense construct (from Step 1, EXAMPLE 24) into *Roseobacter denitrificans* and confirm the presence of the DNA construct.

Step 3: Use chemical synthesis to make a DNA construct that contains a CDOL gene (SEQ ID NO:3) without the transit peptide, linker (SEQ ID NO:15), partCS/PLP-DC gene (SEQ ID NO:11) all in frame. Clone the CDOL/linker/partCS/PLP-DC fragment into a bacterial expression vector, such as pET11, pKK223-3, or pSF-Tac, so it is functional.

The CDOL gene is as follows:

a. Derived from SEQ ID NO:3 by removing nucleotides 4 through 159 (corresponding to the native transit peptide) and without the stop codon, optimized for expression in *Roseobacter denitrificans* and encoding a CDOL peptide from *Chlamydomonas reinhardtii* (SEQ ID NO:4 minus amino acids 2 through 53); and The partCS/PLP-DC gene is as follows:

a. Derived from SEQ ID NO:11 by removing nucleotides 1 through 1413 (corresponding to the native transit and cysteine synthetase peptides), optimized for expression in *Roseobacter denitrificans* and encoding a partCS/PLP-DC peptide from *Micromonas pusilla* (SEQ ID NO:12 minus amino acids 1 through 471); and Step 4: Transform the vector with the functional CDOL/linker/partCS/PLP-DC construct (from Step 3, EXAMPLE 24) into the TauX knockdown *Roseobacter denitrificans* strain (from Step 1, EXAMPLE 24) and confirm the presence of the DNA construct.

Example 25

Development of a Transgenic Bacterium with a TauY Suppressed that Expresses CDOL without the Transit Peptide Fused with a Linker to partCS/PLP-DC Using Chemical Synthesis Step 1: Use chemical synthesis to make an antisense construct to silence or suppress TauY (SEQ ID NO: 32) and clone into the pBAD vector as described by Stefan et al. (313)

The TauY antisense is as follows:

a. Fuse the polynucleotides for SEQ ID NO:68 to polynucleotides 1 through 360 of SEQ ID NO:32. Clone the TauY antisense fragment into a bacterial expression vector, pBAD, so the TauY antisense fragment can be expressed.

Step 2: Transform the vector with the TauY antisense construct (from Step 1, EXAMPLE 25) into *Roseobacter denitrificans* and confirm the presence of the DNA construct Step 3: Transform the vector with the functional CDOL/linker/partCS/PLP-DC construct (from Step 3, EXAMPLE 24) into the TauY knockdown *Roseobacter denitrificans* strain (from Step 1, EXAMPLE 25) and confirm the presence of the DNA construct.

Example 26

Development of a Transgenic Bacterium with a Tpa Suppressed that Expresses CDOL without the Transit Peptide Fused with a Linker to partCS/PLP-DC Using Chemical Synthesis Step 1: Use chemical synthesis to make an antisense construct to silence or suppress Tpa (SEQ ID NO: 34) and clone into the pBAD vector as described by Stefan et al. (313)

The TauY antisense is as follows:

a. Fuse the polynucleotides for SEQ ID NO:68 to polynucleotides 1 through 360 of SEQ ID NO:34. Clone the Tpa antisense fragment into the bacterial expression vector, pBAD, so Tpa antisense fragment can be expressed.

Step 2: Transform the vector with the Tpa antisense construct (from Step 1, EXAMPLE 26) into *Roseobacter denitrificans* and confirm the presence of the DNA construct.

Step 3: Transform the vector with the functional CDOL/linker/partCS/PLP-DC construct (from Step 3, EXAMPLE 24) into the Tpa knockdown *Roseobacter denitrificans* strain (from Step 1, EXAMPLE 26) and confirm the presence of the DNA construct.

Example 27

Develop Bacteria with Taurine

Grow bacteria with CS/PLP-DC (such as from EXAMPLE 1) and induce gene expression with the appropriate inducer associated with the vector. Collect the cells and confirm that the cells express the CS/PLP-DC peptide (~96.6 kDa) using western blot analysis and that have increased taurine using HPLC analysis.

Example 28

Develop Aquafeed Using Bacterial Cells with Taurine

Grow bacteria with CS/PLP-DC (such as from EXAMPLE 1) and induce gene expression with the appropriate inducer associated with the vector. Collect the cells and process for use as an additive to feed.

Example 28

Develop an *E. coli* Strain that Produces Taurine

This example demonstrates the use of a TauD knockout that expresses a CDOL fused to SADL with a linker (CDOL-linker-partCS/PLP-DC) (such as from EXAMPLE 1) to produce taurine in an *E. coli*. Transformed *E. coli* were confirmed by selection and PCR analysis. *E. coli* were grown in ZYP media (314) and induced using autoinduction with an 8:1 lactose to glucose ratio. Free amino acids were extracted from 2 hr culture after the addition of cysteine (200 uM) to determine the level of taurine using high-performance liquid chromatography (HPLC). The bacteria were separated from the supernatant by centrifugation and the level of taurine was determined in the pellet and supernatant. The taurine levels were 0.26% and 1.0% of total extracted free amino acids for the pellet and supernatant, respectively.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cell comprising:
   (a) a genetic deletion or disruption of one or more of the genes selected from the group consisting of the TauD gene, the SsuD gene, SsuE gene and the Cbl gene and
   (b) an expression cassette that comprises a promoter operably linked to a polynucleotide which encodes a cysteine synthetase/PLP decarboxylase (CS/PLP-DC) protein having the amino acid sequence set forth in SEQ ID NO:12,
   wherein the cell is an *Escherichia coli* cell or a *Corynebacterium glutamicum* cell,
   wherein the TauD gene encodes a protein having the amino acid sequence set forth in SEQ ID NO:21, the SsuD gene encodes a protein having an amino acid sequence set forth in SEQ ID NO:23 or 27, the SsuE gene encodes a protein having an amino acid sequence set forth in SEQ ID NO:25 or 29 and the Cbl gene encodes a protein having an amino acid sequence set forth in SEQ ID NO:37 or 39, wherein the cell has no expression of the gene product of one or more of the TauD gene, the SsuD gene, the SsuE gene and the Cbl gene, wherein the expression cassette is expressed in the cell and wherein the cell produces taurine.

2. The cell of claim 1, wherein the CS/PLP-DC polynucleotide comprises the nucleotide sequence set forth in SEQ ID NO:11.

3. The cell of claim 1, wherein the bacterial cell is an *E. coli.* cell.

4. A method of producing taurine comprising growing the cell of claim 1 under conditions which permit expression of the expression cassette thereby producing taurine.

5. The method of claim 4, wherein a sulfur-containing compound or sulfate is added to the cell.

\* \* \* \* \*

```
                        SEQUENCE LISTING

<160> NUMBER OF SEQ ID NOS: 68

<210> SEQ ID NO 1
<211> LENGTH: 606
<212> TYPE: DNA
<213> ORGANISM: Danio rerio

<400> SEQUENCE: 1
atggagcaga ctgaagtcat gaagcccgag actctggagg atctgatcaa aactctgcat      60
cagatcttcc agagcgactc catcaatgtg gaggaggtgc agaacctgat ggagtcctac     120
cagagcaacc cgcaggactg gatgaagttc gccaagttcg accagtacag gtacaccagg     180
aacctcgtgg atgaaggaaa cggaaagttc aacctgatga tcctgtgctg gggtgaagga     240
cacggcagca gcatccatga ccacacagac tcgcactgct tcctgaagct gctgcagggt     300
cagctgaagg agacgctgtt cgactggccc gaccgcaagc tgcagagcgg catgaagccc     360
cgcggccaga gcgtgctgca ggagaaccag tgcgcgtaca tcaacgactc tctgggactc     420
caccgtgtgg agaatgtgag ccacacagag ccggccgtga gtctgcacct ttacagtcct     480
ccgttccaga gctgccgcac gtttgaccag cgcaccggac accacaacac cgtcaagatg     540
accttctgga gcaaatatgg cgagaggacg ccctatgagc tgagcgtctc gcaggagaat     600
aactga                                                                606

<210> SEQ ID NO 2
<211> LENGTH: 201
<212> TYPE: PRT
<213> ORGANISM: Danio rerio

<400> SEQUENCE: 2

Met Glu Gln Thr Glu Val Met Lys Pro Glu Thr Leu Glu Asp Leu Ile
1               5                   10                  15
```

```
Lys Thr Leu His Gln Ile Phe Gln Ser Asp Ser Ile Asn Val Glu Glu
             20                  25                  30

Val Gln Asn Leu Met Glu Ser Tyr Gln Ser Asn Pro Gln Asp Trp Met
         35                  40                  45

Lys Phe Ala Lys Phe Asp Gln Tyr Arg Tyr Thr Arg Asn Leu Val Asp
 50                  55                  60

Glu Gly Asn Gly Lys Phe Asn Leu Met Ile Leu Cys Trp Gly Glu Gly
 65                  70                  75                  80

His Gly Ser Ser Ile His Asp His Thr Asp Ser His Cys Phe Leu Lys
                 85                  90                  95

Leu Leu Gln Gly Gln Leu Lys Glu Thr Leu Phe Asp Trp Pro Asp Arg
             100                 105                 110

Lys Leu Gln Ser Gly Met Lys Pro Arg Gly Gln Ser Val Leu Gln Glu
         115                 120                 125

Asn Gln Cys Ala Tyr Ile Asn Asp Ser Leu Gly Leu His Arg Val Glu
130                 135                 140

Asn Val Ser His Thr Glu Pro Ala Val Ser Leu His Leu Tyr Ser Pro
145                 150                 155                 160

Pro Phe Gln Ser Cys Arg Thr Phe Asp Gln Arg Thr Gly His His Asn
                 165                 170                 175

Thr Val Lys Met Thr Phe Trp Ser Lys Tyr Gly Glu Arg Thr Pro Tyr
             180                 185                 190

Glu Leu Ser Val Ser Gln Glu Asn Asn
         195                 200

<210> SEQ ID NO 3
<211> LENGTH: 810
<212> TYPE: DNA
<213> ORGANISM: Chlamydomonas reinhardtii

<400> SEQUENCE: 3
atgtcttcta tcatcgctat gcctatcaac gaggacggtg tcgttgtggt cgaccgcaag      60
ctgctgggca acgaggtcga gagcaaggcc cgctgcgcgg acaccgcctg caccgcggct     120
gcgcccgccc cgcccgccac ggcggccgcg cccacctcca tgccggagct gttgcaggcg     180
ttgcagcgcg ccattgacga ggagaaggcc actggccagg tcgccatcaa cgctgtggac     240
cagacgcccg agtccgctgc gcggctgagc gcccgcgtgc aggctctact ctcggcctac     300
accagctcca actcgggcga ctggcgacgc tacgccatgt tcaacgacat ccactacgtg     360
cgcaacctgg tggatgccaa tgaggacttt gaactaattg ttctttgttg aagcgcggg      420
caagtcagcc gcgtgcacaa ccacgccaac gcgcactgct ggctggcggt gctggacggc     480
gagatgcgcg agacgcagtt ccagcgcgcg tccgcgccgc cggctgccc cgcgcccgcg      540
gcctcggagc acgatggcag cactgtgtac gtggagccca cacaggtgtc cgacatgcga     600
gtgggtgacg ccggctacat caacgactcc atggcgctgc acaacgtggg tgttgcatg      660
cccgccctgg ccgctggcga ggagggcccc gagggcgggg tgacgctgca ctgctacgcc     720
ccccgattc gccgcgtcaa gatctatgag gacagcaagg tcacggagcg cgtgcccggc      780
tactactcca agggcggagt gcgcgtttga                                       810

<210> SEQ ID NO 4
<211> LENGTH: 269
<212> TYPE: PRT
<213> ORGANISM: Chlamydomonas reinhardtii
```

<400> SEQUENCE: 4

```
Met Ser Ser Ile Ile Ala Met Pro Ile Asn Glu Asp Gly Val Val
1               5                   10                  15

Val Asp Arg Lys Leu Leu Gly Asn Glu Val Glu Ser Lys Ala Arg Cys
            20                  25                  30

Ala Asp Thr Ala Cys Thr Ala Ala Pro Ala Pro Ala Thr Ala
        35                  40                  45

Ala Ala Pro Thr Ser Met Pro Glu Leu Leu Gln Ala Leu Gln Arg Ala
    50                  55                  60

Ile Asp Glu Glu Lys Ala Thr Gly Gln Val Ala Ile Asn Ala Val Asp
65                  70                  75                  80

Gln Thr Pro Glu Ser Ala Ala Arg Leu Ser Ala Arg Val Gln Ala Leu
                85                  90                  95

Leu Ser Ala Tyr Thr Ser Ser Asn Ser Gly Asp Trp Arg Arg Tyr Ala
            100                 105                 110

Met Phe Asn Asp Ile His Tyr Val Arg Asn Leu Val Asp Ala Asn Glu
        115                 120                 125

Asp Phe Glu Leu Ile Val Leu Cys Trp Lys Arg Gly Gln Val Ser Arg
130                 135                 140

Val His Asn His Ala Asn Ala His Cys Trp Leu Ala Val Leu Asp Gly
145                 150                 155                 160

Glu Met Arg Glu Thr Gln Phe Gln Arg Ala Ser Ala Pro Pro Gly Cys
                165                 170                 175

Pro Ala Pro Ala Ala Ser Glu His Asp Gly Ser Thr Val Tyr Val Glu
            180                 185                 190

Pro Thr Gln Val Ser Asp Met Arg Val Gly Asp Ala Gly Tyr Ile Asn
        195                 200                 205

Asp Ser Met Ala Leu His Asn Val Gly Cys Cys Met Pro Ala Leu Ala
210                 215                 220

Ala Gly Glu Glu Gly Pro Glu Gly Gly Val Thr Leu His Cys Tyr Ala
225                 230                 235                 240

Pro Pro Ile Arg Arg Val Lys Ile Tyr Glu Asp Ser Lys Val Thr Glu
                245                 250                 255

Arg Val Pro Gly Tyr Tyr Ser Lys Gly Val Arg Val
            260                 265
```

<210> SEQ ID NO 5
<211> LENGTH: 1449
<212> TYPE: DNA
<213> ORGANISM: Danio rerio

<400> SEQUENCE: 5

```
atggacgagt ctgatgggaa gctgttcctt actgaggctt caacataat  catggaagaa      60
attcttaaca aggaaggga  cttgaaggag aaggtttgtg agtggaaaga tccagatcag     120
ctgagatctc tcctggacct cgaacttcgg atcatggag  aatgtcatga aagctgctg     180
cagagggttc gagatgtggc caaatacagc gtaaaaactt gtcatcctcg gttcttcaat     240
cagctgtttg ctggcgtgga ctatcatgca ctgacaggac ggctcatcac tgaaaccctc     300
aataccagcc aatacaccta tgaagtggct ccagtgtttg tcctgatgga ggaggaagtg     360
atcagtaagc ttcgctctct ggttggctgg tcagaaggag atgggatctt tgtcctgga     420
ggatccatgt ctaacatgta tgccattaac gtcgctcgt  actgggcttt tcctcaagtg     480
aagacaaaag gcttgtgggc cgcaccacgg atggctatat tcacatcaca acagagtcat     540
```

```
tactccgtga aaaaggagc tgcgtttctt ggtattggaa cagaaaatgt tttcattgtg    600
caagtggatg agagcggcag catgatacca aagacctgg aggcaaaaat tgtgcaggca    660
aaatcccaag acgctgttcc gttttcgta acgccacag ccggaaccac agtgcaggga    720 gccttttgacc ctctgaagcg catagctgac atatgtgaaa gaaacggcat gtggatgcat    780
gttgacgccg catggggagg aagcgtgctg ttttccaaaa agcacagaca tctggttgca    840
ggaatagaaa gagcaaactc ggtgacttgg aatcctcaca aaatgcttct gacgggactg    900
cagtgctctg tgattttgtt cagagatact acgaatttgc tcatgcactg tcacagtgcc    960
aaagccacat acttgttcca gcaagacaag ttctacgaca caagtctgga cacgggcgac   1020
aaatccatcc agtgtggccg gaaggtggat tgcctcaagc tctggctcat gtggaaggca   1080
atcggagcta gtggtctttc acagcgtgtc gataaggcct ttgccctcac taggtattta   1140
gttgaagaaa tggagaaacg ggagaatttc cagctggtct gtaaggggcc gtttgtgaac   1200
gtttgcttct ggtttattcc acccagtctg aaggaaagg agaacagccc agattaccag   1260
gaaagactat ccaaggtggc gccagtcatt aaagagagga tgatgaagcg aggaacgatg   1320
atggtgggat atcagccaat ggatgaacac gtcaacttct ccgcatggt ggttgtttct   1380 ccacagctca caaccaaaga catggatttc ttccttgatg agatggagaa actcgggaag   1440
gatctatga                                                           1449

<210> SEQ ID NO 6
<211> LENGTH: 482
<212> TYPE: PRT
<213> ORGANISM: Danio rerio

<400> SEQUENCE: 6

Met Asp Glu Ser Asp Gly Lys Leu Phe Leu Thr Glu Ala Phe Asn Ile
1               5                  10                  15

Ile Met Glu Glu Ile Leu Asn Lys Gly Arg Asp Leu Lys Glu Lys Val
            20                  25                  30

Cys Glu Trp Lys Asp Pro Asp Gln Leu Arg Ser Leu Leu Asp Leu Glu
        35                  40                  45

Leu Arg Asp His Gly Glu Cys His Glu Lys Leu Leu Gln Arg Val Arg
    50                  55                  60

Asp Val Ala Lys Tyr Ser Val Lys Thr Cys His Pro Arg Phe Phe Asn
65                  70                  75                  80

Gln Leu Phe Ala Gly Val Asp Tyr His Ala Leu Thr Gly Arg Leu Ile
                85                  90                  95

Thr Glu Thr Leu Asn Thr Ser Gln Tyr Thr Tyr Glu Val Ala Pro Val
            100                 105                 110

Phe Val Leu Met Glu Glu Val Ile Ser Lys Leu Arg Ser Leu Val
            115                 120                 125

Gly Trp Ser Glu Gly Asp Gly Ile Phe Cys Pro Gly Gly Ser Met Ser
        130                 135                 140

Asn Met Tyr Ala Ile Asn Val Ala Arg Tyr Trp Ala Phe Pro Gln Val
145                 150                 155                 160

Lys Thr Lys Gly Leu Trp Ala Ala Pro Arg Met Ala Ile Phe Thr Ser
                165                 170                 175

Gln Gln Ser His Tyr Ser Val Lys Lys Gly Ala Ala Phe Leu Gly Ile
            180                 185                 190

Gly Thr Glu Asn Val Phe Ile Val Gln Val Asp Glu Ser Gly Ser Met
            195                 200                 205
```

```
Ile Pro Glu Asp Leu Glu Ala Lys Ile Val Gln Ala Lys Ser Gln Asp
    210                 215                 220
Ala Val Pro Phe Phe Val Asn Ala Thr Ala Gly Thr Thr Val Gln Gly
225                 230                 235                 240
Ala Phe Asp Pro Leu Lys Arg Ile Ala Asp Ile Cys Glu Arg Asn Gly
                245                 250                 255
Met Trp Met His Val Asp Ala Ala Trp Gly Gly Ser Val Leu Phe Ser
                260                 265                 270
Lys Lys His Arg His Leu Val Ala Gly Ile Glu Arg Ala Asn Ser Val
            275                 280                 285
Thr Trp Asn Pro His Lys Met Leu Leu Thr Gly Leu Gln Cys Ser Val
290                 295                 300
Ile Leu Phe Arg Asp Thr Thr Asn Leu Leu Met His Cys His Ser Ala
305                 310                 315                 320
Lys Ala Thr Tyr Leu Phe Gln Gln Asp Lys Phe Tyr Asp Thr Ser Leu
                325                 330                 335
Asp Thr Gly Asp Lys Ser Ile Gln Cys Gly Arg Lys Val Asp Cys Leu
                340                 345                 350
Lys Leu Trp Leu Met Trp Lys Ala Ile Gly Ala Ser Gly Leu Ser Gln
            355                 360                 365
Arg Val Asp Lys Ala Phe Ala Leu Thr Arg Tyr Leu Val Glu Glu Met
370                 375                 380
Glu Lys Arg Glu Asn Phe Gln Leu Val Cys Lys Gly Pro Phe Val Asn
385                 390                 395                 400
Val Cys Phe Trp Phe Ile Pro Pro Ser Leu Lys Gly Lys Glu Asn Ser
                405                 410                 415
Pro Asp Tyr Gln Glu Arg Leu Ser Lys Val Ala Pro Val Ile Lys Glu
                420                 425                 430
Arg Met Met Lys Arg Gly Thr Met Met Val Gly Tyr Gln Pro Met Asp
            435                 440                 445
Glu His Val Asn Phe Phe Arg Met Val Val Val Ser Pro Gln Leu Thr
            450                 455                 460
Thr Lys Asp Met Asp Phe Phe Leu Asp Glu Met Glu Lys Leu Gly Lys
465                 470                 475                 480
Asp Leu

<210> SEQ ID NO 7
<211> LENGTH: 1629
<212> TYPE: DNA
<213> ORGANISM: Guillardia theta

<400> SEQUENCE: 7
atggtgcccc ccgccttgca tgaagggttc tgcagccctc gaggcaggac ttgttgctct      60
caggtgggac acgtggagtt gttggagagc tgggaaacgc aggggaacaa gctgagatgc    120
gagcaagacc tcctgctggc caaggttccc tctcgcttcc accacttga ggaagtggcc    180 gagctggatg atatcttcag ggaggtgtat cctctgatcc ggcagtacga gacggagaac    240
gcgctagcag acgagcacaa ggtgctggag ttcaggacgc cagcggagct gaaggaggag    300
gtggacgtgg ggctgcctga ggagggatct gtggagaaat tgtcgaggg atgcagaagc    360 tctatgaagt acagcgtccg aacgagtcac ccgcgcttca tgaaccagct ctatgctggc    420 agcgaccccgg cagggcaggt ggcagagctg ctcagtgctg tgctgaacac caccatccac    480
acgtacgggg cagctcccct cttctccgtg ctggagcggc aggtgatcga agctgggg    540
```

```
aggatgctgg ggtttcagga gcatgtcgac ggcgtctttg cccccggagg ctcgtacgcg    600
aacatggtgg cgctgatagt tgcgaggaac cagcacttcc ctcatgtgcg ggagcatggc    660
tggaggagcg acgacaaacc tgttatcttc acttcttccc atgctcacta ctctgtcgcc    720
aaggctgcca tgatcacggg gatggggtcg aatcaagtgg tcgctgtgcc tacggacgag    780
cagggaagaa tgcagcctgc agcgctggag gaggagatta tgcgagcaaa ggagagcgga    840
cggaagcctt tctacgtgag ctgcacggca gggacgacag tgactggggc gtttgacccg    900
attgacgaga tctgtcagat atgtagaagg catgagatgt ggctgcacac ggatggcgcg    960
tggggaggag ctgcaatatt ctcggaggag cacagaaatc ttctacgagg agttgagggc   1020
gtcgatagct tctgcttgaa tccgcacaag atgctggggg tcccgatgca gtgctccgtg   1080
ctcatcctca caaccacga ggggcgctcg agaggagcaa cagaggaaga gagcttggat    1140
ctcgggcaga agtcgctgca gtgcggaagg aaacctgatt gcctaaagct ctggctctgc   1200
tggaagcgac atggaacccg cgggtttgca aggagggtag atcgcgcgta taccttctcg   1260
cagaagttcg cagaaatggt cagaagggac cccaggttct acctgctgat ggacccgatc   1320
tcctgcaacg tctgcttctt ctacctccct ccctccctcc ggcagcagct ggtggacaga   1380
aacctcaacg acttggaaaa ggaggaggcg cagcggcagc tcaaggagtt ccatgctcga   1440
ctcggtcagg ttactcagat catctacagg aggatgcaga agacggcaa gatgctcatc    1500
aacttcagcc ctcttaaaga cagagatctg cctcacttct tccgagccgt catgatccag   1560
cagagagtaa cggaagacga tcttgttttc atcctcgatc attttgaaca tctgggaaag   1620
gacctctag                                                           1629
```

<210> SEQ ID NO 8
<211> LENGTH: 542
<212> TYPE: PRT
<213> ORGANISM: Guillardia theta

<400> SEQUENCE: 8

```
Met Val Pro Pro Ala Leu His Glu Gly Phe Cys Ser Pro Arg Gly Arg
1               5                   10                  15

Thr Cys Cys Ser Gln Val Gly His Val Glu Leu Leu Glu Ser Trp Glu
            20                  25                  30

Thr Gln Gly Asn Lys Leu Arg Cys Glu Gln Asp Leu Leu Leu Ala Lys
        35                  40                  45

Val Pro Ser Arg Phe His His Leu Glu Glu Val Ala Glu Leu Asp Asp
    50                  55                  60

Ile Phe Arg Glu Val Tyr Pro Leu Ile Arg Gln Tyr Glu Thr Glu Asn
65                  70                  75                  80

Ala Leu Ala Asp Glu His Lys Val Leu Glu Phe Arg Thr Pro Ala Glu
                85                  90                  95

Leu Lys Glu Glu Val Asp Val Gly Leu Pro Glu Glu Gly Ser Val Glu
            100                 105                 110

Lys Phe Val Glu Gly Cys Arg Ser Ser Met Lys Tyr Ser Val Arg Thr
        115                 120                 125

Ser His Pro Arg Phe Met Asn Gln Leu Tyr Ala Gly Ser Asp Pro Ala
    130                 135                 140

Gly Gln Val Ala Glu Leu Leu Ser Ala Val Leu Asn Thr Thr Ile His
145                 150                 155                 160

Thr Tyr Gly Ala Ala Pro Phe Phe Ser Val Leu Glu Arg Gln Val Ile
                165                 170                 175
```

```
Glu Lys Leu Gly Arg Met Leu Gly Phe Gln Glu His Val Asp Gly Val
                180                 185                 190

Phe Ala Pro Gly Gly Ser Tyr Ala Asn Met Val Ala Leu Ile Val Ala
            195                 200                 205

Arg Asn Gln His Phe Pro His Val Arg Glu His Gly Trp Arg Ser Asp
        210                 215                 220

Asp Lys Pro Val Ile Phe Thr Ser Ser His Ala His Tyr Ser Val Ala
225                 230                 235                 240

Lys Ala Ala Met Ile Thr Gly Met Gly Ser Asn Gln Val Val Ala Val
                245                 250                 255

Pro Thr Asp Glu Gln Gly Arg Met Gln Pro Ala Ala Leu Glu Glu Glu
            260                 265                 270

Ile Met Arg Ala Lys Glu Ser Gly Arg Lys Pro Phe Tyr Val Ser Cys
        275                 280                 285

Thr Ala Gly Thr Thr Val Thr Gly Ala Phe Asp Pro Ile Asp Glu Ile
        290                 295                 300

Cys Gln Ile Cys Arg Arg His Glu Met Trp Leu His Thr Asp Gly Ala
305                 310                 315                 320

Trp Gly Gly Ala Ala Ile Phe Ser Glu Glu His Arg Asn Leu Leu Arg
                325                 330                 335

Gly Val Glu Gly Val Asp Ser Phe Cys Leu Asn Pro His Lys Met Leu
            340                 345                 350

Gly Val Pro Met Gln Cys Ser Val Leu Ile Leu Asn Asn His Glu Gly
        355                 360                 365

Arg Ser Arg Gly Ala Thr Glu Glu Glu Ser Leu Asp Leu Gly Gln Lys
        370                 375                 380

Ser Leu Gln Cys Gly Arg Lys Pro Asp Cys Leu Lys Leu Trp Leu Cys
385                 390                 395                 400

Trp Lys Arg His Gly Thr Arg Gly Phe Ala Arg Arg Val Asp Arg Ala
                405                 410                 415

Tyr Thr Phe Ser Gln Lys Phe Ala Glu Met Val Arg Arg Asp Pro Arg
            420                 425                 430

Phe Tyr Leu Leu Met Asp Pro Ile Ser Cys Asn Val Cys Phe Phe Tyr
        435                 440                 445

Leu Pro Pro Ser Leu Arg Gln Gln Leu Val Asp Arg Asn Leu Asn Asp
    450                 455                 460

Leu Glu Lys Glu Glu Ala Gln Arg Gln Leu Lys Glu Phe His Ala Arg
465                 470                 475                 480

Leu Gly Gln Val Thr Gln Ile Ile Tyr Arg Arg Met Gln Lys Asp Gly
                485                 490                 495

Lys Met Leu Ile Asn Phe Ser Pro Leu Lys Asp Arg Asp Leu Pro His
            500                 505                 510

Phe Phe Arg Ala Val Met Ile Gln Gln Arg Val Thr Glu Asp Asp Leu
        515                 520                 525

Val Phe Ile Leu Asp His Phe Glu His Leu Gly Lys Asp Leu
    530                 535                 540

<210> SEQ ID NO 9
<211> LENGTH: 1776
<212> TYPE: DNA
<213> ORGANISM: Danio rerio

<400> SEQUENCE: 9
atggcggcgt ctgcaccctc ctcctcctct tctggcggcg ttccggatcc caactcgaca      60
```

```
aatttacagc caccttcctc aaactacgac tggagtggag tcgctcatgg atgtacaagg    120
aagcttggaa tgaagatatg tgggttcttg cagaagaaca ataatgttga cgacaagggt    180
cgaattgtcg ggttgtttaa cgaccagcag cccaggagta ttttaacccg ggacaacgag    240
cgagattccc gcttcagacg cacagagacg gacttctcca atctgtatgc aagagatctg    300
cttcctgcta aaaatggcga ggagtacacc atgcagttcc tgctggaggt ggtggagatc    360
ctcactaact acgtgcgcaa gaccttcgac agatccacca aagtgctgga cttccaccat    420
ccacaccagc tgctggaagg catggagggc ttcaacctgg agctgtgtga ccagcccgag    480
agtctggagc agatcctggt ggactgcagg gacactctca aatatggagt ccggacaggt    540
cacccaaggt tttttaacca gctgtcttca ggactagaca tcatcggttt agctggagaa    600
tggttgacct ccactgccaa caccaacatg ttcacgtatg agattgcgcc agtgtttgtc    660
ctgatggagc agctcacact gaagaagatg cgagagattg tcggctggcc gaacggagaa    720
ggagatggca ttttctcacc aggaggagcc atctccaaca tgtacagcgt gatggtggct    780
cgatataaac actatcctga gattaaaatc aaaggcatgg cggcggctcc cagactggtg    840
ctgttcacct cagaacacag tcactactct ataaagaagg ccagtgcagt gttgggtttc    900
ggcacagaga atctgatcct gctgagaacg gatgaaagag gtcgagttat tccagctgat    960
ttggaggcca agtcattga cgccaagcag aagggctttg tgccgatgtt tgtgaacgca   1020
acggctggat ctacagtgta cggagccttc gacccaatca atgagatcgc cgacatctgt   1080
gagaaataca acatgtggct tcacgtagat ggagcgtggg gtggaggttt gctgatgtct   1140
agaaaacaca acacaagct cagtggcatt gagagagcaa actccgtcac ctggaaccca   1200
cacaagatga tgggtgttcc tctacagtgc tccgccattc tggtccggga agggtctt   1260 ctacagggct gtaattccat gtgcgctgga tatctcttc agccggataa gcagtatgac   1320
gtcacctatg acacggggga caaggccata cagtgtggcc gtcatgtaga catcttcaaa   1380
ttctggctca tgtggaagtc aaagggcact actggttttg agaagcacat tgacaggtgt   1440
ctggagctgt cggagtatct ctaccacaag atcaagaaca gagaaggata tgagatggtg   1500
tttcaagggg agccacagca cacaaatgta tgtttctggt acattcctcc aagcctgcgg   1560
cttctgccag atggagagga gaacgacat cggcttcata aggtcgcccc aaagatcaag   1620
gcactgatga tggagtgcgg gacaacaatg gtgggctacc agcctcaggg tgagaaggtt   1680
aacttcttca ggatggtggt ctccaatccg gcggttacca ggtctgacat tgacttcctg   1740
atcgatgaga tagaaagact gggacaggat ttatag                             1776
```

<210> SEQ ID NO 10
<211> LENGTH: 591
<212> TYPE: PRT
<213> ORGANISM: Danio rerio

<400> SEQUENCE: 10

Met Ala Ala Ser Ala Pro Ser Ser Ser Ser Gly Gly Val Pro Asp
1               5                   10                  15

Pro Asn Ser Thr Asn Leu Gln Pro Pro Ser Ser Asn Tyr Asp Trp Ser
                20                  25                  30

Gly Val Ala His Gly Cys Thr Arg Lys Leu Gly Met Lys Ile Cys Gly
            35                  40                  45

Phe Leu Gln Lys Asn Asn Asn Val Asp Asp Lys Gly Arg Ile Val Gly
        50                  55                  60

Leu Phe Asn Asp Gln Gln Pro Arg Ser Ile Leu Thr Arg Asp Asn Glu

```
                65                  70                  75                  80
Arg Asp Ser Arg Phe Arg Thr Glu Thr Asp Phe Ser Asn Leu Tyr
                        85                  90                  95

Ala Arg Asp Leu Leu Pro Ala Lys Asn Gly Glu Glu Tyr Thr Met Gln
                       100                 105                 110

Phe Leu Leu Glu Val Val Glu Ile Leu Thr Asn Tyr Val Arg Lys Thr
                       115                 120                 125

Phe Asp Arg Ser Thr Lys Val Leu Asp Phe His His Pro His Gln Leu
                130                 135                 140

Leu Glu Gly Met Glu Gly Phe Asn Leu Glu Leu Cys Asp Gln Pro Glu
145                 150                 155                 160

Ser Leu Glu Gln Ile Leu Val Asp Cys Arg Asp Thr Leu Lys Tyr Gly
                            165                 170                 175

Val Arg Thr Gly His Pro Arg Phe Phe Asn Gln Leu Ser Ser Gly Leu
                180                 185                 190

Asp Ile Ile Gly Leu Ala Gly Glu Trp Leu Thr Ser Thr Ala Asn Thr
                    195                 200                 205

Asn Met Phe Thr Tyr Glu Ile Ala Pro Val Phe Val Leu Met Glu Gln
                210                 215                 220

Leu Thr Leu Lys Lys Met Arg Glu Ile Val Gly Trp Pro Asn Gly Glu
225                 230                 235                 240

Gly Asp Gly Ile Phe Ser Pro Gly Gly Ala Ile Ser Asn Met Tyr Ser
                        245                 250                 255

Val Met Val Ala Arg Tyr Lys His Tyr Pro Glu Ile Lys Ile Lys Gly
                260                 265                 270

Met Ala Ala Ala Pro Arg Leu Val Leu Phe Thr Ser Glu His Ser His
                    275                 280                 285

Tyr Ser Ile Lys Lys Ala Ser Ala Val Leu Gly Phe Gly Thr Glu Asn
                290                 295                 300

Leu Ile Leu Leu Arg Thr Asp Glu Arg Gly Arg Val Ile Pro Ala Asp
305                 310                 315                 320

Leu Glu Ala Lys Val Ile Asp Ala Lys Gln Lys Gly Phe Val Pro Met
                        325                 330                 335

Phe Val Asn Ala Thr Ala Gly Ser Thr Val Tyr Gly Ala Phe Asp Pro
                    340                 345                 350

Ile Asn Glu Ile Ala Asp Ile Cys Glu Lys Tyr Asn Met Trp Leu His
                355                 360                 365

Val Asp Gly Ala Trp Gly Gly Leu Leu Met Ser Arg Lys His Lys
                370                 375                 380

His Lys Leu Ser Gly Ile Glu Arg Ala Asn Ser Val Thr Trp Asn Pro
385                 390                 395                 400

His Lys Met Met Gly Val Pro Leu Gln Cys Ser Ala Ile Leu Val Arg
                        405                 410                 415

Glu Lys Gly Leu Leu Gln Gly Cys Asn Ser Met Cys Ala Gly Tyr Leu
                    420                 425                 430

Phe Gln Pro Asp Lys Gln Tyr Asp Val Thr Tyr Asp Thr Gly Asp Lys
                435                 440                 445

Ala Ile Gln Cys Gly Arg His Val Asp Ile Phe Lys Phe Trp Leu Met
                450                 455                 460

Trp Lys Ser Lys Gly Thr Thr Gly Phe Glu Lys His Ile Asp Arg Cys
465                 470                 475                 480

Leu Glu Leu Ser Glu Tyr Leu Tyr His Lys Ile Lys Asn Arg Glu Gly
                        485                 490                 495
```

-continued

```
        Tyr Glu Met Val Phe Gln Gly Glu Pro Gln His Thr Asn Val Cys Phe
                    500                 505                 510

Trp Tyr Ile Pro Pro Ser Leu Arg Leu Leu Pro Asp Gly Glu Glu Lys
                    515                 520                 525

Arg His Arg Leu His Lys Val Ala Pro Lys Ile Lys Ala Leu Met Met
                    530                 535                 540

Glu Cys Gly Thr Thr Met Val Gly Tyr Gln Pro Gln Gly Glu Lys Val
        545                 550                 555                 560

Asn Phe Phe Arg Met Val Val Ser Asn Pro Ala Val Thr Arg Ser Asp
                            565                 570                 575

Ile Asp Phe Leu Ile Asp Glu Ile Glu Arg Leu Gly Gln Asp Leu
                    580                 585                 590

<210> SEQ ID NO 11
<211> LENGTH: 2958
<212> TYPE: DNA
<213> ORGANISM: Micromonas pusilla

<400> SEQUENCE: 11
atgtccgcgg cgacgggatc attatcccta cccctactcg ggcatctcgc gacctcgcgt      60
aacgcacgcg cgcgtcggaa ccgcgccgcc gcggccatcc ccggcgtctc cctcgggaaa     120
tcgacctcgg ttttcactcc gcgaggtcct aagcgcatcg cgcgcgtcgt cacctcgaag     180
gcgggcccgc attcgaaccc tccgagggcg atatcgaccg tcgacgacgt cctcgcgttc     240
accgtgccca ccgacgagcc cgcggccgag accgcctccc ccgccgacag cgactgcgaa     300
ggcgagttct gcgacatgaa ggagagctcg tgcacgacga gggacctcat cggcagcacg     360
ccgctgctcg atctgagcgc gtactccctg aaccccaccg tgaagatcct cgcgaagtgc     420
gagtacctca acccgtccgg gtccatcaaa gaccgcatcg cgacgcacat cctggacaag     480
gcgatcaaga gcggcgatct caagcccggg atgaccgtcg tcgcggcgac gtccgggaac     540
accggcgccg cgatcgcgat ggcgtgcgcg ttgcgcgggt acgactacat cgtcatcacc     600
aacgagaaga cgtccaagga gaaggtggac gcgatgagag cgtacggcgg cgaggtgatc     660
gtctccccgt ccggggtgtc cccggacgac ccacagcact accagaacat cgagaacaag     720
ctgtgcgagg agaaccccgg gacgtactac ggcgtggatc agtataacaa cccgtacaac     780
gcggacgcgt acgaggcgac gctcgggccg gagatttggc gtcagagcgt gggcgcggtg     840
acgcacttca tcgtcggcgg cagcaccggc ggcacggtca gcggcacggg gaggtacttg     900
aagcaagaga cccggacgt gaggatcgtc ctcgcggacc cgagagggag cgtgttctgg     960
gaccacgtcg tcaacggcgt cgccgccgac gacgtcaagg tgtccaagtc gtgggagacg    1020
gagggcgtcg gcaaggattc catccccggg tgcctcgacg tctcgatcgt ggacgggatg    1080
gtgcgcgcga cggacgagca ggcgttcggc gtgtgccgcg agctcgcgag cagcgacggc    1140
ctcctcgtcg gcggcagcag cggtctgaac ctccacgcct cgcgcgtgtt atccggcgac    1200
gtcgcggacg acagcgtcat cgtcacggtg ttcccggaca acggcgtgaa gtacctgtcg    1260
aagatttaca cgacgactg gctcgactcg aagaagatgg cggcgcaaa gaactcggac    1320 gggaacgcgg agagagccgc ggagtgcgag gtgtactggc cccggacgc gctctcgttc    1380 gcggagcgaa aggcggcgg ggacgccgcc gccgccgccg ccgtcgaggg cgacaacctc    1440
tggcccgagg acgagaccga gcgcgagctc aagttcctgg aggaactcgc gccgaagctg    1500
acgcagtacc acagagactc catcaagggc gacgagcgcg tgcacagcaa gctccagtcc    1560
```

-continued

```
ccggaggagc tcgcggcgac gttcgccgcc gcggggcgc ccatcgacct cgcggagggc    1620
gacgccccg cgacggagga gcaactcgcg ctcgcggtgc aggcggtcat ggacaactcg    1680
gtccgctcct cgcacccgat gttcttgaac cagctgtacg ccggcgtcga cgtcgtcgcg    1740
ctcgcgggg agtggaccgc gagcgcgttg aacgccaacg tgcacacgtt tgaagtcgcg    1800
ccggtgctca cggagattga aaagccgtc ctcgcgaaaa ccgcgcggat gtggctgaac    1860
aagcccgggt ctaagacgac gccgccgcac gacggtctgc tcgtccccgg cgggtccctg    1920
gcgaacatgt actcgatgat cctcgcgcgc gatcgcgcgg agccggaggc gaagaccaag    1980
ggcgcgagcg caacctcgt cgcgttttgc tcggagcagt cgcactactc gtacaaaaag    2040
tccgcgatgg tcatgggcct cgggatggac aacatgatca aggtgaagtg cgaccagtcc    2100
ggcgcgatga tcccggcgga gctcgagaag gcggttcagg aggccaagtc ccggggcaag    2160
gtgccgttct acgtcggcac caccgcgggg tccaccgtgc tcggcgcctt tgacgactac    2220
gaaggctgcg cggacgtctg cgaaaagcac gacatgtgga tgcacgtcga cggcgcgtgg    2280
ggcggcgccg cggcgctgtc cccgacgaga aggcacaatc tccagggcgc gaacagagcg    2340
gactcgttct gctggaaccc gcacaagatg ctcgggttgc cgctccagtg ctccatcttc    2400
gtgacgaagc aacccggggc gctgtccaag gcgaacgccg cgcaggcgga ctacttgttc    2460
cagccggaca gaacaacgc cgccgcggac ctcggcgacc gcacgattca gtgcggacgc    2520
aaggcggacg ccctcaagat ctggctcgcg tggaaggcgc gcggagacga aggctgggcg    2580
aatctcgtgg accgctcctt tggcctcgcg gagtacgtcg aggcgtcggt gcgcgagcgg    2640
tgcgaaaaag acggctcgtt cgtcctcgcc gcgcccgcgc agtgcgcgaa catcgggttc    2700
tggtacgtgc ccccgcgcct gaggccgttc gatgtcgagt ccgcgaccgc ggaccagctc    2760
acggagattg ggttcgtcgc cccgaagctg aaggaccgga tgcaacggac cggggacgcg    2820
atgatcgggt ccagccgat cgactcgatg aaccttccaa actttttccg actcgtgctt    2880
ccaaactcga ggcacctgtc gaagaacgcg ctcgacgcta tgctcgatcg catggacgac    2940
atgggcaaag acctgtga                                                  2958
```

<210> SEQ ID NO 12
<211> LENGTH: 985
<212> TYPE: PRT
<213> ORGANISM: Micromonas pusilla

<400> SEQUENCE: 12

```
Met Ser Ala Ala Thr Gly Ser Leu Ser Leu Pro Leu Leu Gly His Leu
1               5                   10                  15

Ala Thr Ser Arg Asn Ala Arg Ala Arg Arg Asn Arg Ala Ala Ala
            20                  25                  30

Ile Pro Gly Val Ser Leu Gly Lys Ser Thr Ser Val Phe Thr Pro Arg
        35                  40                  45

Gly Pro Lys Arg Ile Ala Arg Val Val Thr Ser Lys Ala Gly Pro His
    50                  55                  60

Ser Asn Pro Pro Arg Ala Ile Ser Thr Val Asp Asp Val Leu Ala Phe
65                  70                  75                  80

Thr Val Pro Thr Asp Glu Pro Ala Ala Glu Thr Ala Ser Pro Ala Asp
                85                  90                  95

Ser Asp Cys Glu Gly Glu Phe Cys Asp Met Lys Glu Ser Ser Cys Thr
            100                 105                 110

Thr Arg Asp Leu Ile Gly Ser Thr Pro Leu Leu Asp Leu Ser Ala Tyr
        115                 120                 125
```

```
Ser Leu Asn Pro Thr Val Lys Ile Leu Ala Lys Cys Glu Tyr Leu Asn
        130                 135                 140
Pro Ser Gly Ser Ile Lys Asp Arg Ile Ala Thr His Ile Leu Asp Lys
145                 150                 155                 160
Ala Ile Lys Ser Gly Asp Leu Lys Pro Gly Met Thr Val Val Ala Ala
                165                 170                 175
Thr Ser Gly Asn Thr Gly Ala Ala Ile Ala Met Ala Cys Ala Leu Arg
                180                 185                 190
Gly Tyr Asp Tyr Ile Val Ile Thr Asn Glu Lys Thr Ser Lys Glu Lys
                195                 200                 205
Val Asp Ala Met Arg Ala Tyr Gly Gly Glu Val Ile Val Ser Pro Ser
210                 215                 220
Gly Val Ser Pro Asp Asp Pro Gln His Tyr Gln Asn Ile Glu Asn Lys
225                 230                 235                 240
Leu Cys Glu Glu Asn Pro Gly Thr Tyr Tyr Gly Val Asp Gln Tyr Asn
                245                 250                 255
Asn Pro Tyr Asn Ala Asp Ala Tyr Glu Ala Thr Leu Gly Pro Glu Ile
                260                 265                 270
Trp Arg Gln Ser Val Gly Ala Val Thr His Phe Ile Val Gly Gly Ser
        275                 280                 285
Thr Gly Gly Thr Val Ser Gly Thr Gly Arg Tyr Leu Lys Gln Glu Asn
        290                 295                 300
Pro Asp Val Arg Ile Val Leu Ala Asp Pro Arg Gly Ser Val Phe Trp
305                 310                 315                 320
Asp His Val Val Asn Gly Val Ala Asp Val Lys Val Ser Lys
                325                 330                 335
Ser Trp Glu Thr Glu Gly Val Gly Lys Asp Ser Ile Pro Gly Cys Leu
                340                 345                 350
Asp Val Ser Ile Val Asp Gly Met Val Arg Ala Thr Asp Glu Gln Ala
                355                 360                 365
Phe Gly Val Cys Arg Glu Leu Ala Ser Ser Asp Gly Leu Leu Val Gly
        370                 375                 380
Gly Ser Ser Gly Leu Asn Leu His Ala Ser Arg Val Leu Ser Gly Asp
385                 390                 395                 400
Val Ala Asp Asp Ser Val Ile Val Thr Val Phe Pro Asp Asn Gly Val
                405                 410                 415
Lys Tyr Leu Ser Lys Ile Tyr Asn Asp Asp Trp Leu Asp Ser Lys Lys
                420                 425                 430
Met Gly Gly Ala Lys Asn Ser Asp Gly Asn Ala Glu Arg Ala Ala Glu
        435                 440                 445
Cys Glu Val Tyr Trp Arg Pro Asp Ala Leu Ser Phe Ala Glu Arg Lys
450                 455                 460
Ala Ala Ala Asp Ala Ala Ala Ala Ala Val Glu Gly Asp Asn Leu
465                 470                 475                 480
Trp Pro Glu Asp Glu Thr Glu Arg Glu Leu Lys Phe Leu Glu Glu Leu
                485                 490                 495
Ala Pro Lys Leu Thr Gln Tyr His Arg Asp Ser Ile Lys Gly Asp Glu
                500                 505                 510
Arg Val His Ser Lys Leu Gln Ser Pro Glu Glu Leu Ala Ala Thr Phe
        515                 520                 525
Ala Ala Ala Gly Ala Pro Ile Asp Leu Ala Glu Gly Asp Ala Pro Ala
530                 535                 540
```

-continued

```
Thr Glu Glu Gln Leu Ala Leu Ala Val Gln Ala Val Met Asp Asn Ser
545                 550                 555                 560

Val Arg Ser Ser His Pro Met Phe Leu Asn Gln Leu Tyr Ala Gly Val
            565                 570                 575

Asp Val Val Ala Leu Ala Gly Glu Trp Thr Ala Ser Ala Leu Asn Ala
        580                 585                 590

Asn Val His Thr Phe Glu Val Ala Pro Val Leu Thr Glu Ile Glu Lys
    595                 600                 605

Ala Val Leu Ala Lys Thr Ala Arg Met Trp Leu Asn Lys Pro Gly Ser
610                 615                 620

Lys Thr Thr Pro Pro His Asp Gly Leu Leu Val Pro Gly Gly Ser Leu
625                 630                 635                 640

Ala Asn Met Tyr Ser Met Ile Leu Ala Arg Asp Arg Ala Glu Pro Glu
            645                 650                 655

Ala Lys Thr Lys Gly Ala Ser Gly Asn Leu Val Ala Phe Cys Ser Glu
        660                 665                 670

Gln Ser His Tyr Ser Tyr Lys Lys Ser Ala Met Val Met Gly Leu Gly
    675                 680                 685

Met Asp Asn Met Ile Lys Val Lys Cys Asp Gln Ser Gly Ala Met Ile
690                 695                 700

Pro Ala Glu Leu Glu Lys Ala Val Gln Glu Ala Lys Ser Arg Gly Lys
705                 710                 715                 720

Val Pro Phe Tyr Val Gly Thr Thr Ala Gly Ser Thr Val Leu Gly Ala
            725                 730                 735

Phe Asp Asp Tyr Glu Gly Cys Ala Asp Val Cys Glu Lys His Asp Met
        740                 745                 750

Trp Met His Val Asp Gly Ala Trp Gly Gly Ala Ala Leu Ser Pro
    755                 760                 765

Thr Arg Arg His Asn Leu Gln Gly Ala Asn Arg Ala Asp Ser Phe Cys
770                 775                 780

Trp Asn Pro His Lys Met Leu Gly Leu Pro Leu Gln Cys Ser Ile Phe
785                 790                 795                 800

Val Thr Lys Gln Pro Gly Ala Leu Ser Lys Ala Asn Ala Ala Gln Ala
            805                 810                 815

Asp Tyr Leu Phe Gln Pro Asp Lys Asn Asn Ala Ala Ala Asp Leu Gly
        820                 825                 830

Asp Arg Thr Ile Gln Cys Gly Arg Lys Ala Asp Ala Leu Lys Ile Trp
    835                 840                 845

Leu Ala Trp Lys Ala Arg Gly Asp Glu Gly Trp Ala Asn Leu Val Asp
850                 855                 860

Arg Ser Phe Gly Leu Ala Glu Tyr Val Glu Ala Ser Val Arg Glu Arg
865                 870                 875                 880

Cys Glu Lys Asp Gly Ser Phe Val Leu Ala Ala Pro Ala Gln Cys Ala
            885                 890                 895

Asn Ile Gly Phe Trp Tyr Val Pro Pro Arg Leu Arg Pro Phe Asp Val
        900                 905                 910

Glu Ser Ala Thr Ala Asp Gln Leu Thr Glu Ile Gly Phe Val Ala Pro
    915                 920                 925

Lys Leu Lys Asp Arg Met Gln Arg Thr Gly Asp Ala Met Ile Gly Phe
930                 935                 940

Gln Pro Ile Asp Ser Met Asn Leu Pro Asn Phe Phe Arg Leu Val Leu
945                 950                 955                 960

Pro Asn Ser Arg His Leu Ser Lys Asn Ala Leu Asp Ala Met Leu Asp
```

Arg Met Asp Asp Met Gly Lys Asp Leu
            980                 985

<210> SEQ ID NO 13
<211> LENGTH: 177
<212> TYPE: DNA
<213> ORGANISM: Arabidopsis thaliana

<400> SEQUENCE: 13
atggctgctt atggtcaaat ctcctcggga atgactgtag atcctcaggt tctctcttcc      60
tccagaaaca ttggagtttc cctatcacct ctccggagaa cactaatcgg cgccggagtt     120
aggtctacta gtatctctct ccgtcaatgt tctctctccg ttagatcgat taaaatc        177

<210> SEQ ID NO 14
<211> LENGTH: 59
<212> TYPE: PRT
<213> ORGANISM: Arabidopsis thaliana

<400> SEQUENCE: 14

Met Ala Ala Tyr Gly Gln Ile Ser Ser Gly Met Thr Val Asp Pro Gln
1               5                   10                  15

Val Leu Ser Ser Ser Arg Asn Ile Gly Val Ser Leu Ser Pro Leu Arg
            20                  25                  30

Arg Thr Leu Ile Gly Ala Gly Val Arg Ser Thr Ser Ile Ser Leu Arg
        35                  40                  45

Gln Cys Ser Leu Ser Val Arg Ser Ile Lys Ile
    50                  55

<210> SEQ ID NO 15
<211> LENGTH: 39
<212> TYPE: DNA
<213> ORGANISM: Artificial Sequence
<220> FEATURE:
<223> OTHER INFORMATION: Synthetic sequence

<400> SEQUENCE: 15
agtactgaag gcgaagttaa cgcggaagaa gaaggctttt                             39

<210> SEQ ID NO 16
<211> LENGTH: 1020
<212> TYPE: DNA
<213> ORGANISM: Escherichia coli

<400> SEQUENCE: 16
atgaatgttt ttattcctga atactgctcc cataacaaga caggggagca gacaatcatg      60
gcaatttcat cgcgtaacac acttcttgcc gcactggcat tcatcgcttt tcaggcacag     120
gcggtgaacg tcaccgtggc gtatcaaacc tcagccgaac cggcgaaagt ggctcaggcc     180
gacaacacct tgctaaaga aagcggagca accgtggact ggcgtaagtt tgacagcgga     240
gccagcatcg tgcgggcgct ggcttcaggc gacgtgcaaa tcggcaacct cggttccagc     300
ccgttagcgg ttgcagccag ccaacaggtg ccgattgaag tcttcttgct ggcgtcaaaa     360
ctgggtaact ccgaagcgct ggtggtaaag aaaactatca gcaaaccgga agatctgatt     420
ggcaaacgca tcgccgtacc gtttatctcc accacccact acagcctgct ggcggcactg     480
aaacactggg gcattaaacc cggcaagtg agagattgtga acctgcagcc gcccgcgatt     540
atcgctgcct ggcagcgggg agatattgat ggtgcttatg tctgggcacc ggcggttaac     600

```
gccctggaaa aagacggcaa ggtgttgacc gattctgaac aggtcgggca gtggggcgcg    660
ccaacgctgg acgtctgggt ggtgcgcaaa gattttgccg agaaacatcc tgaggtcgtg    720
aaagcgttcg ctaaaagcgc catcgatgct cagcaaccgt acattgctaa cccagacgtg    780
tggctgaaac agccggaaaa catcagcaaa ctggcgcgtt taagcggcgt gcctgaaggt    840
gacgttccgg ggctggtgaa ggggaatacc tatctgacgc cgcagcaaca aacggcagaa    900
ctgaccggac cggtgaacaa agcgatcatc gacaccgcgc agttttttgaa agagcagggc    960 aaggtcccgg ctgtagcgaa tgattacagc cagtacgtta cctcgcgctt cgtgcaataa   1020
```

<210> SEQ ID NO 17
<211> LENGTH: 320
<212> TYPE: PRT
<213> ORGANISM: Escherichia coli

<400> SEQUENCE: 17

```
Met Ala Ile Ser Ser Arg Asn Thr Leu Leu Ala Ala Leu Ala Phe Ile
1               5                   10                  15

Ala Phe Gln Ala Gln Ala Val Asn Val Thr Val Ala Tyr Gln Thr Ser
            20                  25                  30

Ala Glu Pro Ala Lys Val Ala Gln Ala Asp Asn Thr Phe Ala Lys Glu
        35                  40                  45

Ser Gly Ala Thr Val Asp Trp Arg Lys Phe Asp Ser Gly Ala Ser Ile
    50                  55                  60

Val Arg Ala Leu Ala Ser Gly Asp Val Gln Ile Gly Asn Leu Gly Ser
65                  70                  75                  80

Ser Pro Leu Ala Val Ala Ala Ser Gln Gln Val Pro Ile Glu Val Phe
                85                  90                  95

Leu Leu Ala Ser Lys Leu Gly Asn Ser Glu Ala Leu Val Val Lys Lys
            100                 105                 110

Thr Ile Ser Lys Pro Glu Asp Leu Ile Gly Lys Arg Ile Ala Val Pro
        115                 120                 125

Phe Ile Ser Thr Thr His Tyr Ser Leu Leu Ala Ala Leu Lys His Trp
    130                 135                 140

Gly Ile Lys Pro Gly Gln Val Glu Ile Val Asn Leu Gln Pro Pro Ala
145                 150                 155                 160

Ile Ile Ala Ala Trp Gln Arg Gly Asp Ile Asp Gly Ala Tyr Val Trp
                165                 170                 175

Ala Pro Ala Val Asn Ala Leu Glu Lys Asp Gly Lys Val Leu Thr Asp
            180                 185                 190

Ser Glu Gln Val Gly Gln Trp Gly Ala Pro Thr Leu Asp Val Trp Val
        195                 200                 205

Val Arg Lys Asp Phe Ala Glu Lys His Pro Glu Val Val Lys Ala Phe
    210                 215                 220

Ala Lys Ser Ala Ile Asp Ala Gln Gln Pro Tyr Ile Ala Asn Pro Asp
225                 230                 235                 240

Val Trp Leu Lys Gln Pro Glu Asn Ile Ser Lys Leu Ala Arg Leu Ser
                245                 250                 255

Gly Val Pro Glu Gly Asp Val Pro Gly Leu Val Lys Gly Asn Thr Tyr
            260                 265                 270

Leu Thr Pro Gln Gln Gln Thr Ala Glu Leu Thr Gly Pro Val Asn Lys
        275                 280                 285

Ala Ile Ile Asp Thr Ala Gln Phe Leu Lys Glu Gln Gly Lys Val Pro
    290                 295                 300
```

Ala Val Ala Asn Asp Tyr Ser Gln Tyr Val Thr Ser Arg Phe Val Gln
305                 310                 315                 320

<210> SEQ ID NO 18
<211> LENGTH: 1017
<212> TYPE: DNA
<213> ORGANISM: Roseobacter denitrificans

<400> SEQUENCE: 18

```
atgacatttc tttcacggat cacgtccggc acagcgattg ccctgacggc gaccatcatg     60
agcatcggcg cggctgatgc caaaaacttc aagatcgccg tgggcgacag cggcggcagc    120
agccaggaag ccaccggttt ggctttcatc gaagcccttg aggagctttc gggcggcgag    180
cacactgcaa cgctgtttct gaacggacag ttggggtccg agcaagacac agtcaacgac    240
gcggccatcg gctcgctcga catgtcgatc ctggcgatca acaacgtgac accgttctcg    300
ccaactgttg gcgtcttctc gcttccatac gtgatcctga gcctcgaaga tgctgaaaag    360
ctgacccagg gcccgatcgg tcaggaactg acagaaaaca caatcgaaga cgcaggcgtt    420
cgtatcgtgg cctggaccta cacgggtttc cgccgcctga ccaattccaa aaagccggtc    480
acatccgttg ccgatctgca aggtctcgtc attcgcgttc caagaacga atcatgatc     540
gacacctaca aggcctgggg catcagccca acgccgatgg catggtcgga accctttgcg    600
ggcctgcaaa ccggcgttgt cgacggtcag gacaacccct acaccaccat caacgcgatg    660
aagttctacg aagtacaaaa gtacgtcacg aacatccgct acatcttctc catcgaacct    720
ctgatcgtgt ccgagcaggt gtttcaggag ctttccgctg aagatcagga aatcattctg    780
gaagcaggca agcgcgcgac ggccgcgtct gcacagttcc tgcgcgacaa ggaagcagag    840
atcaaggaac tgctggtcga aaaaggcatg cagatcgacg acccggtcaa caatgagcag    900
gagttcattg atctggcgac agcagctgtc tggccgaagt tctacgacag catcggcggc    960
atcgaaaaga tgaacgctgt tctggctgaa atcggccgcg agccggtctc gaataa      1017
```

<210> SEQ ID NO 19
<211> LENGTH: 338
<212> TYPE: PRT
<213> ORGANISM: Roseobacter denitrificans

<400> SEQUENCE: 19

Met Thr Phe Leu Ser Arg Ile Thr Ser Gly Thr Ala Ile Ala Leu Thr
1               5                   10                  15

Ala Thr Ile Met Ser Ile Gly Ala Ala Asp Ala Lys Asn Phe Lys Ile
            20                  25                  30

Ala Val Gly Asp Ser Gly Gly Ser Gln Glu Ala Thr Gly Leu Ala
        35                  40                  45

Phe Ile Glu Ala Leu Glu Glu Leu Ser Gly Gly Glu His Thr Ala Thr
    50                  55                  60

Leu Phe Leu Asn Gly Gln Leu Gly Ser Glu Gln Asp Thr Val Asn Asp
65                  70                  75                  80

Ala Ala Ile Gly Ser Leu Asp Met Ser Ile Leu Ala Ile Asn Asn Val
                85                  90                  95

Thr Pro Phe Ser Pro Thr Val Gly Val Phe Ser Leu Pro Tyr Val Ile
            100                 105                 110

Leu Ser Leu Glu Asp Ala Glu Lys Leu Thr Gln Gly Pro Ile Gly Gln
        115                 120                 125

Glu Leu Thr Glu Asn Thr Ile Glu Asp Ala Gly Val Arg Ile Val Ala
    130                 135                 140

Trp Thr Tyr Thr Gly Phe Arg Arg Leu Thr Asn Ser Lys Lys Pro Val
145                 150                 155                 160

Thr Ser Val Ala Asp Leu Gln Gly Leu Val Ile Arg Val Pro Lys Asn
            165                 170                 175

Glu Ile Met Ile Asp Thr Tyr Lys Ala Trp Gly Ile Ser Pro Thr Pro
        180                 185                 190

Met Ala Trp Ser Glu Thr Phe Ala Gly Leu Gln Thr Gly Val Val Asp
        195                 200                 205

Gly Gln Asp Asn Pro Tyr Thr Thr Ile Asn Ala Met Lys Phe Tyr Glu
210                 215                 220

Val Gln Lys Tyr Val Thr Asn Ile Arg Tyr Ile Phe Ser Ile Glu Pro
225                 230                 235                 240

Leu Ile Val Ser Glu Gln Val Phe Gln Glu Leu Ser Ala Glu Asp Gln
            245                 250                 255

Glu Ile Ile Leu Glu Ala Gly Lys Arg Ala Thr Ala Ala Ser Ala Gln
        260                 265                 270

Phe Leu Arg Asp Lys Glu Ala Glu Ile Lys Glu Leu Leu Val Glu Lys
        275                 280                 285

Gly Met Gln Ile Asp Asp Pro Val Asn Asn Glu Gln Glu Phe Ile Asp
290                 295                 300

Leu Ala Thr Ala Ala Val Trp Pro Lys Phe Tyr Asp Ser Ile Gly Gly
305                 310                 315                 320

Ile Glu Lys Met Asn Ala Val Leu Ala Glu Ile Gly Arg Glu Pro Val
            325                 330                 335

Ser Glu

<210> SEQ ID NO 20
<211> LENGTH: 852
<212> TYPE: DNA
<213> ORGANISM: Escherichia coli

<400> SEQUENCE: 20
atgagtgaac gtctgagcat taccccgctg gggccgtata tcggcgcaca aatttcgggt      60
gccgacctga cgcgcccgtt aagcgataat cagtttgaac agctttacca tgcggtgctg     120
cgccatcagg tggtgtttct acgcgatcaa gctattacgc cgcagcagca acgcgcgctg     180
gcccagcgtt ttggcgaatt gcatattcac cctgtttacc gcatgccga aggggttgac      240 gagatcatcg tgctggatac ccataacgat aatccgccag ataacgacaa ctggcatacc     300 gatgtgcat ttattgaaac gccacccgca ggggcgattc tggcagctaa agagttacct      360
tcgaccggcg tgatacgct ctggaccagc ggtattgcgg cctatgaggc gctctctgtt      420
cccttccgcc agctgctgag tgggctgcgt gcggagcatg atttccgtaa atcgttcccg     480
gaatacaaat accgcaaaac cgaggaggaa catcaacgct ggcgcgaggc ggtcgcgaaa     540
aacccgccgt tgctacatcc ggtggtgcga acgcatccgg tgagcggtaa acaggcgctg     600
tttgtgaatg aaggctttac tacgcgaatt gttgatgtga gcgagaaaga gagcgaagcc     660
ttgttaagtt ttttgtttgc ccatatcacc aaaccggagt ttcaggtgcg ctggcgctgg     720
caaccaaatg atattgcgat ttgggataac cgcgtgaccc agcactatgc caatgccgat     780
tacctgccac agcgacggat aatgcatcgg gcgacgatcc ttggggataa accgttttat     840
cgggcggggt aa                                                         852

<210> SEQ ID NO 21

<211> LENGTH: 283
<212> TYPE: PRT
<213> ORGANISM: Escherichia coli

<400> SEQUENCE: 21

| | | | | | | | | | | | | | | |
|---|---|---|---|---|---|---|---|---|---|---|---|---|---|---|
| Met | Ser | Glu | Arg | Leu | Ser | Ile | Thr | Pro | Leu | Gly | Pro | Tyr | Ile | Gly | Ala |
| 1 | | | | 5 | | | | | 10 | | | | | 15 | |
| Gln | Ile | Ser | Gly | Ala | Asp | Leu | Thr | Arg | Pro | Leu | Ser | Asp | Asn | Gln | Phe |
| | | | 20 | | | | | 25 | | | | | 30 | | |
| Glu | Gln | Leu | Tyr | His | Ala | Val | Leu | Arg | His | Gln | Val | Phe | Leu | Arg | |
| | | 35 | | | | | 40 | | | | | 45 | | | |
| Asp | Gln | Ala | Ile | Thr | Pro | Gln | Gln | Arg | Ala | Leu | Ala | Gln | Arg | Phe | |
| | 50 | | | | | 55 | | | | | 60 | | | | |
| Gly | Glu | Leu | His | Ile | His | Pro | Val | Tyr | Pro | His | Ala | Glu | Gly | Val | Asp |
| 65 | | | | | 70 | | | | | 75 | | | | | 80 |
| Glu | Ile | Ile | Val | Leu | Asp | Thr | His | Asn | Asp | Asn | Pro | Pro | Asp | Asn | Asp |
| | | | | 85 | | | | | 90 | | | | | 95 | |
| Asn | Trp | His | Thr | Asp | Val | Thr | Phe | Ile | Glu | Thr | Pro | Ala | Gly | Ala | |
| | | | 100 | | | | | 105 | | | | | 110 | | |
| Ile | Leu | Ala | Ala | Lys | Glu | Leu | Pro | Ser | Thr | Gly | Gly | Asp | Thr | Leu | Trp |
| | | 115 | | | | | 120 | | | | | 125 | | | |
| Thr | Ser | Gly | Ile | Ala | Ala | Tyr | Glu | Ala | Leu | Ser | Val | Pro | Phe | Arg | Gln |
| | 130 | | | | | 135 | | | | | 140 | | | | |
| Leu | Leu | Ser | Gly | Leu | Arg | Ala | Glu | His | Asp | Phe | Arg | Lys | Ser | Phe | Pro |
| 145 | | | | | 150 | | | | | 155 | | | | | 160 |
| Glu | Tyr | Lys | Tyr | Arg | Lys | Thr | Glu | Glu | Glu | His | Gln | Arg | Trp | Arg | Glu |
| | | | | 165 | | | | | 170 | | | | | 175 | |
| Ala | Val | Ala | Lys | Asn | Pro | Pro | Leu | Leu | His | Pro | Val | Val | Arg | Thr | His |
| | | | 180 | | | | | 185 | | | | | 190 | | |
| Pro | Val | Ser | Gly | Lys | Gln | Ala | Leu | Phe | Val | Asn | Glu | Gly | Phe | Thr | Thr |
| | | 195 | | | | | 200 | | | | | 205 | | | |
| Arg | Ile | Val | Asp | Val | Ser | Glu | Lys | Glu | Ser | Glu | Ala | Leu | Leu | Ser | Phe |
| | 210 | | | | | 215 | | | | | 220 | | | | |
| Leu | Phe | Ala | His | Ile | Thr | Lys | Pro | Glu | Phe | Gln | Val | Arg | Trp | Arg | Trp |
| 225 | | | | | 230 | | | | | 235 | | | | | 240 |
| Gln | Pro | Asn | Asp | Ile | Ala | Ile | Trp | Asp | Asn | Arg | Val | Thr | Gln | His | Tyr |
| | | | | 245 | | | | | 250 | | | | | 255 | |
| Ala | Asn | Ala | Asp | Tyr | Leu | Pro | Gln | Arg | Arg | Ile | Met | His | Arg | Ala | Thr |
| | | | 260 | | | | | 265 | | | | | 270 | | |
| Ile | Leu | Gly | Asp | Lys | Pro | Phe | Tyr | Arg | Ala | Gly | | | | | |
| | | 275 | | | | | 280 | | | | | | | | |

<210> SEQ ID NO 22
<211> LENGTH: 1146
<212> TYPE: DNA
<213> ORGANISM: Escherichia coli

<400> SEQUENCE: 22

```
atgagtctga atatgttctg gttttttaccg acccacggtg acgggcatta tctgggaacg      60
gaagaaggtt cacgcccggt tgatcacggt tatctgcaac aaattgcgca agcggcggat     120
cgtcttggct ataccggtgt gctaattcca acggggcgct cctgcgaaga tgcgtggctg     180
gttgccgcat cgatgatccc ggtgacgcag cggctgaagt ttcttgtcgc cctgcgtccc     240
agcgtaacct cacctaccgt tgccgcccgc caggccgcca cgcttgaccg tctctcaaat     300
ggacgtgcgt tgtttaacct ggtcacaggc agcgatccac aagagctggc aggcgacgga     360
```

```
gtgttccttg atcatagcga gcgctacgaa gcctcggcgg aatttaccca ggtctggcgg    420
cgtttattgc agagagaaac cgtcgatttc aacggtaaac atattcatgt gcgcggagca    480
aaactgctct cccggcgat tcaacagccg tatccgccac tttactttgg cggatcgtca    540
gatgtcgccc aggagctggc ggcagaacag gttgatctct acctcacctg gggcgaaccg    600
ccggaactgg ttaaagagaa atcgaacaa gtgcgggcga agctgccgc gcatggacgc    660 aaaattcgtt tcggtattcg tctgcatgtg attgttcgtg aaactaacga cgaagcgtgg    720
caggccgccg agcggttaat ctcgcatctt gatgatgaaa ctatcgccaa agcacaggcc    780
gcattcgccc ggacggattc cgtagggcaa cagcgaatgg cggcgttaca taacggcaag    840
cgcgacaatc tggagatcag ccccaattta tgggcgggcg ttggcttagt gcgcggcggt    900
gccgggacgg cgctggtggg cgatggtcct acggtcgctg cgcgaatcaa cgaatatgcc    960
gcgcttggca tcgacagttt tgtgcttcg ggctatccgc atctggaaga agcgtatcgg   1020
gttggcgagt gctgttccc gcttctggat gtcgccatcc cggaaattcc ccagccgcag   1080
ccgctgaatc cgcaaggcga agcggtggcg aatgatttta tccccgtaa agtcgcgcaa   1140 agctaa                                                             1146
```

<210> SEQ ID NO 23
<211> LENGTH: 381
<212> TYPE: PRT
<213> ORGANISM: Escherichia coli

<400> SEQUENCE: 23

```
Met Ser Leu Asn Met Phe Trp Phe Leu Pro Thr His Gly Asp Gly His
1               5                   10                  15

Tyr Leu Gly Thr Glu Glu Gly Ser Arg Pro Val Asp His Gly Tyr Leu
            20                  25                  30

Gln Gln Ile Ala Gln Ala Ala Asp Arg Leu Gly Tyr Thr Gly Val Leu
        35                  40                  45

Ile Pro Thr Gly Arg Ser Cys Glu Asp Ala Trp Leu Val Ala Ala Ser
    50                  55                  60

Met Ile Pro Val Thr Gln Arg Leu Lys Phe Leu Val Ala Leu Arg Pro
65                  70                  75                  80

Ser Val Thr Ser Pro Thr Val Ala Ala Arg Gln Ala Ala Thr Leu Asp
                85                  90                  95

Arg Leu Ser Asn Gly Arg Ala Leu Phe Asn Leu Val Thr Gly Ser Asp
            100                 105                 110

Pro Gln Glu Leu Ala Gly Asp Gly Val Phe Leu Asp His Ser Glu Arg
        115                 120                 125

Tyr Glu Ala Ser Ala Glu Phe Thr Gln Val Trp Arg Arg Leu Leu Gln
    130                 135                 140

Arg Glu Thr Val Asp Phe Asn Gly Lys His Ile His Val Arg Gly Ala
145                 150                 155                 160

Lys Leu Leu Phe Pro Ala Ile Gln Gln Pro Tyr Pro Pro Leu Tyr Phe
                165                 170                 175

Gly Gly Ser Ser Asp Val Ala Gln Glu Leu Ala Ala Glu Gln Val Asp
            180                 185                 190

Leu Tyr Leu Thr Trp Gly Glu Pro Pro Glu Leu Val Lys Glu Lys Ile
        195                 200                 205

Glu Gln Val Arg Ala Lys Ala Ala His Gly Arg Lys Ile Arg Phe
    210                 215                 220
```

Gly Ile Arg Leu His Val Ile Val Arg Glu Thr Asn Asp Glu Ala Trp
225                 230                 235                 240

Gln Ala Ala Glu Arg Leu Ile Ser His Leu Asp Asp Glu Thr Ile Ala
            245                 250                 255

Lys Ala Gln Ala Ala Phe Ala Arg Thr Asp Ser Val Gly Gln Gln Arg
        260                 265                 270

Met Ala Ala Leu His Asn Gly Lys Arg Asp Asn Leu Glu Ile Ser Pro
    275                 280                 285

Asn Leu Trp Ala Gly Val Gly Leu Val Arg Gly Ala Gly Thr Ala
    290                 295                 300

Leu Val Gly Asp Gly Pro Thr Val Ala Ala Arg Ile Asn Glu Tyr Ala
305                 310                 315                 320

Ala Leu Gly Ile Asp Ser Phe Val Leu Ser Gly Tyr Pro His Leu Glu
                325                 330                 335

Glu Ala Tyr Arg Val Gly Glu Leu Leu Phe Pro Leu Leu Asp Val Ala
            340                 345                 350

Ile Pro Glu Ile Pro Gln Pro Gln Pro Leu Asn Pro Gln Gly Glu Ala
        355                 360                 365

Val Ala Asn Asp Phe Ile Pro Arg Lys Val Ala Gln Ser
370                 375                 380

<210> SEQ ID NO 24
<211> LENGTH: 576
<212> TYPE: DNA
<213> ORGANISM: Escherichia coli

<400> SEQUENCE: 24
atgcgtgtca tcaccctggc gggtagtcct cgctttcctt ctcgctccag ctccttgctg     60
gaatatgcgc gggaaaaact aaatggcctg gatgtagagg tttatcactg gaatctgcaa    120
aacttcgccc cggaagatct actttatgct cgtttcgata gtccggcact caagaccttc    180
accgaacagc tgcaacaggc cgatgggctg attgtcgcca cgcctgtgta taaagccgcc    240
tattccggtg cgttgaaaac cctgctcgac ctgctgccag aacgcgcttt gcaaggcaaa    300
gtggtgctac cgctggcgac gggcggtacc gtggcccatc tgctggcggt cgattatgcc    360
cttaaaccag tttaagcgc actgaaagct caggagatcc tgcacggcgt gtttgccgat    420
gactcacaag taattgatta ccatcacaga ccccagttca cgccaaatct gcaaccccgt    480
cttgataccg cgctagaaac tttctggcag gcattgcacc gccgcgatgt tcaggttcct    540
gaccttctgt ctctgcgagg taatgcccat gcgtaa                              576

<210> SEQ ID NO 25
<211> LENGTH: 191
<212> TYPE: PRT
<213> ORGANISM: Escherichia coli

<400> SEQUENCE: 25

Met Arg Val Ile Thr Leu Ala Gly Ser Pro Arg Phe Pro Ser Arg Ser
1               5                   10                  15

Ser Ser Leu Leu Glu Tyr Ala Arg Glu Lys Leu Asn Gly Leu Asp Val
            20                  25                  30

Glu Val Tyr His Trp Asn Leu Gln Asn Phe Ala Pro Glu Asp Leu Leu
        35                  40                  45

Tyr Ala Arg Phe Asp Ser Pro Ala Leu Lys Thr Phe Thr Glu Gln Leu
    50                  55                  60

Gln Gln Ala Asp Gly Leu Ile Val Ala Thr Pro Val Tyr Lys Ala Ala

```
              65                  70                  75                  80
Tyr Ser Gly Ala Leu Lys Thr Leu Leu Asp Leu Leu Pro Glu Arg Ala
                    85                  90                  95

Leu Gln Gly Lys Val Val Leu Pro Leu Ala Thr Gly Gly Thr Val Ala
               100                 105                 110

His Leu Leu Ala Val Asp Tyr Ala Leu Lys Pro Val Leu Ser Ala Leu
               115                 120                 125

Lys Ala Gln Glu Ile Leu His Gly Val Phe Ala Asp Asp Ser Gln Val
           130                 135                 140

Ile Asp Tyr His His Arg Pro Gln Phe Thr Pro Asn Leu Gln Thr Arg
145                 150                 155                 160

Leu Asp Thr Ala Leu Glu Thr Phe Trp Gln Ala Leu His Arg Arg Asp
                    165                 170                 175

Val Gln Val Pro Asp Leu Leu Ser Leu Arg Gly Asn Ala His Ala
                180                 185                 190

<210> SEQ ID NO 26
<211> LENGTH: 1146
<212> TYPE: DNA
<213> ORGANISM: Corynebacterium glutamicum

<400> SEQUENCE: 26
```

| | | | | |
|---|---|---|---|---|
| atgacattaa | ctttccattg | gttcctatcc | acttcaggcg | attcccgcgg | catcatcggc | 60 |
| ggcggtcacg | gtgcagaaaa | atccggcacc | tcccgcgaat | tgagccacag | ctacctcaag | 120 |
| cagttggcgc | tagctgccga | gaccaacggt | tttgaatctg | tcctgacacc | aacgggcacg | 180 |
| tggtgcgaag | atgcgtggat | tactgacgct | tctttgattg | aggcgacaaa | acgcttgaag | 240 |
| ttcctcgttg | cgcttcgccc | tgggcagatt | ggacctacgc | tgtctgctca | aatggcttct | 300 |
| actttccagc | gtctgtctgg | caaccgtttg | ctgatcaatg | tggtcaccgg | tggggaagat | 360 |
| gcggagcagc | gtgcgtttgg | tgatttcttg | aacaaggagg | agcgctacgc | ccgtaccgga | 420 |
| gaattcttgg | atatcgtgag | ccgcttgtgg | cgaggcgaaa | ccgtcacgca | ccacggtgaa | 480 |
| cacctgcagg | tggagcaagc | tagccttgcg | catccgccag | agattattcc | ggagattctt | 540 |
| tttggtggat | cgtcgccagc | tgcaggtgag | gtggctgcac | gttatgcgga | cacctatctc | 600 |
| acgtggggtg | aaactcccga | tcaggtggcg | cagaaaatca | actggatcaa | cgagctagca | 660 |
| gcacagcgcg | gccgggaact | gccgccatgga | atccgcttcc | atgtgatcac | ccgcgatacg | 720 |
| tctgaagaag | catgggtggt | ggcagagaag | ttgattagcg | gggtcactcc | agaacaggtc | 780 |
| gctaaggctc | aagccgggtt | tgcaacgtct | aagtcggagg | ggcagcgccg | gatggctgag | 840 |
| ctgcacagca | agggtcgtgc | ctttactagt | ggctcaactg | ctcgtgatct | ggaggtgtat | 900 |
| cccaatgtgt | gggcaggcgt | cggttttgctt | cgcggaggtg | caggaacagc | ccttgtgggc | 960 |
| tcgcatgaag | aggtcgccga | tcgcatcgaa | gaatacgcag | cactcggctt | ggatcagttt | 1020 |
| gtactgtcgg | gttatccaaa | cttggaggag | gccttccact | tcggtgaggg | tgtgattccg | 1080 |
| gagctgctgc | gccgcggtgt | ggatatcaaa | aatcaagaat | cacgagtttt | ggaacctgtt | 1140 |
| gggtaa | | | | | | 1146 |

```
<210> SEQ ID NO 27
<211> LENGTH: 381
<212> TYPE: PRT
<213> ORGANISM: Corynebacterium glutamicum

<400> SEQUENCE: 27
```

Met Thr Leu Thr Phe His Trp Phe Leu Ser Thr Ser Gly Asp Ser Arg
1               5                   10                  15

Gly Ile Ile Gly Gly Gly His Gly Ala Glu Lys Ser Gly Thr Ser Arg
            20                  25                  30

Glu Leu Ser His Ser Tyr Leu Lys Gln Leu Ala Leu Ala Ala Glu Thr
        35                  40                  45

Asn Gly Phe Glu Ser Val Leu Thr Pro Thr Gly Thr Trp Cys Glu Asp
50                  55                  60

Ala Trp Ile Thr Asp Ala Ser Leu Ile Glu Ala Thr Lys Arg Leu Lys
65                  70                  75                  80

Phe Leu Val Ala Leu Arg Pro Gly Gln Ile Gly Pro Thr Leu Ser Ala
                85                  90                  95

Gln Met Ala Ser Thr Phe Gln Arg Leu Ser Gly Asn Arg Leu Leu Ile
                100                 105                 110

Asn Val Val Thr Gly Gly Glu Asp Ala Glu Gln Arg Ala Phe Gly Asp
            115                 120                 125

Phe Leu Asn Lys Glu Glu Arg Tyr Ala Arg Thr Gly Glu Phe Leu Asp
            130                 135                 140

Ile Val Ser Arg Leu Trp Arg Gly Glu Thr Val Thr His His Gly Glu
145                 150                 155                 160

His Leu Gln Val Glu Gln Ala Ser Leu Ala His Pro Pro Glu Ile Ile
                165                 170                 175

Pro Glu Ile Leu Phe Gly Gly Ser Ser Pro Ala Ala Gly Glu Val Ala
                180                 185                 190

Ala Arg Tyr Ala Asp Thr Tyr Leu Thr Trp Gly Glu Thr Pro Asp Gln
                195                 200                 205

Val Ala Gln Lys Ile Asn Trp Ile Asn Glu Leu Ala Ala Gln Arg Gly
210                 215                 220

Arg Glu Leu Arg His Gly Ile Arg Phe His Val Ile Thr Arg Asp Thr
225                 230                 235                 240

Ser Glu Glu Ala Trp Val Val Ala Glu Lys Leu Ile Ser Gly Val Thr
                245                 250                 255

Pro Glu Gln Val Ala Lys Ala Gln Ala Gly Phe Ala Thr Ser Lys Ser
            260                 265                 270

Glu Gly Gln Arg Arg Met Ala Glu Leu His Ser Lys Gly Arg Ala Phe
        275                 280                 285

Thr Ser Gly Ser Thr Ala Arg Asp Leu Glu Val Tyr Pro Asn Val Trp
290                 295                 300

Ala Gly Val Gly Leu Leu Arg Gly Gly Ala Gly Thr Ala Leu Val Gly
305                 310                 315                 320

Ser His Glu Glu Val Ala Asp Arg Ile Glu Glu Tyr Ala Ala Leu Gly
                325                 330                 335

Leu Asp Gln Phe Val Leu Ser Gly Tyr Pro Asn Leu Glu Glu Ala Phe
            340                 345                 350

His Phe Gly Glu Gly Val Ile Pro Glu Leu Leu Arg Arg Gly Val Asp
        355                 360                 365

Ile Lys Asn Gln Glu Ser Arg Val Leu Glu Pro Val Gly
370                 375                 380

<210> SEQ ID NO 28
<211> LENGTH: 924
<212> TYPE: DNA
<213> ORGANISM: Corynebacterium glutamicum

<400> SEQUENCE: 28

-continued

```
atgacgtccc cgcataattt tgtcagtggt gctattgatc tgggtgaggt gaaagcgcgt      60
gcggatgcgc gccagaaggc ccatgagcag gggccggtaa ctcagggcat tgctagttcc     120
cttgatgtga ccatggagaa cctggagaat gaggtgctgc gtcgttccac gcaggttccg     180
gtgattgttc tcgtgggtac cccgcgcagc cctgattcgg agcagttgaa gtcggatctg     240
accacgcttg ctgctgaaag tggcaggaag ttcattttcg gttatgtcaa tgctgatacc     300
gatgctgatg tggcccaggt gtttggggtg cagggcttgc cgtcggtgat tgctgtggca     360
gcgggacgcc ctctggctga tttccagggc ggacagccag cggatgcact aaagcagtgg     420
actgatcagg tggttcaggc tgtgggtgga cagctggaag gactgccaga ggaggccaca     480
gacggcgaac aagaagacgc tcctgtggaa gaccccgct tcgatgctgc cactgatgct      540
ctaaaccgtg gcgctttcga tgaggcgatt gcggtttatg agtccatttt ggcgcaggag     600
ccaaacaacg ctgatgcgaa gcaggcacgc gataccgcaa agctgttggg ccggcttgcc     660
acggtggatc cttcggtgga tgttgtcgct gctgcagatg ctgatccaac aaacgttgat     720
ctggcctaca cagcagctga cgcggctgtt gttgcgggtg atcctgaggc tgcctttgat     780
cgtttaattg ctctgctgac catcagcgct ggcgatcaga agaatcaggt gaaggaacgt     840
ttgctggagc tgtttggcat gtttgagacc gccgatcccc gtgtgctgca ggcgcgagga     900
aagatggcca gcgcgctgtt ctaa                                            924
```

<210> SEQ ID NO 29
<211> LENGTH: 307
<212> TYPE: PRT
<213> ORGANISM: Corynebacterium glutamicum

<400> SEQUENCE: 29

```
Met Thr Ser Pro His Asn Phe Val Ser Gly Ala Ile Asp Leu Gly Glu
1               5                   10                  15

Val Lys Ala Arg Ala Asp Ala Arg Gln Lys Ala His Glu Gln Gly Pro
            20                  25                  30

Val Thr Gln Gly Ile Ala Ser Ser Leu Asp Val Thr Met Glu Asn Leu
        35                  40                  45

Glu Asn Glu Val Leu Arg Arg Ser Thr Gln Val Pro Val Ile Val Leu
    50                  55                  60

Val Gly Thr Pro Arg Ser Pro Asp Ser Glu Gln Leu Lys Ser Asp Leu
65                  70                  75                  80

Thr Thr Leu Ala Ala Glu Ser Gly Arg Lys Phe Ile Phe Gly Tyr Val
                85                  90                  95

Asn Ala Asp Thr Asp Ala Asp Val Ala Gln Val Phe Gly Val Gln Gly
            100                 105                 110

Leu Pro Ser Val Ile Ala Val Ala Gly Arg Pro Leu Ala Asp Phe
        115                 120                 125

Gln Gly Gly Gln Pro Ala Asp Ala Leu Lys Gln Trp Thr Asp Gln Val
    130                 135                 140

Val Gln Ala Val Gly Gly Gln Leu Glu Gly Leu Pro Glu Glu Ala Thr
145                 150                 155                 160

Asp Gly Glu Gln Glu Asp Ala Pro Val Glu Asp Pro Arg Phe Asp Ala
                165                 170                 175

Ala Thr Asp Ala Leu Asn Arg Gly Ala Phe Asp Glu Ala Ile Ala Val
            180                 185                 190

Tyr Glu Ser Ile Leu Ala Gln Glu Pro Asn Asn Ala Asp Ala Lys Gln
        195                 200                 205
```

```
Ala Arg Asp Thr Ala Lys Leu Leu Gly Arg Leu Ala Thr Val Asp Pro
    210                 215                 220

Ser Val Asp Val Val Ala Ala Asp Ala Asp Pro Thr Asn Val Asp
225                 230                 235                 240

Leu Ala Tyr Thr Ala Asp Ala Ala Val Val Ala Gly Asp Pro Glu
                245                 250                 255

Ala Ala Phe Asp Arg Leu Ile Ala Leu Leu Thr Ile Ser Ala Gly Asp
                260                 265                 270

Gln Lys Asn Gln Val Lys Glu Arg Leu Leu Glu Leu Phe Gly Met Phe
            275                 280                 285

Glu Thr Ala Asp Pro Arg Val Leu Gln Ala Arg Gly Lys Met Ala Ser
    290                 295                 300

Ala Leu Phe
305

<210> SEQ ID NO 30
<211> LENGTH: 387
<212> TYPE: DNA
<213> ORGANISM: Roseobacter denitrificans

<400> SEQUENCE: 30
atgaccaaaa cactgacagc tcaggacttg tccgacacct ttgacgcctt caatcgccat      60
gacgttgatg gcgtcatgac acatttcgcc gatgattgcg tgttctacac cgtgggcggg     120
gatgaagcct atggcgccaa agtcgaaggc gcagaagcga ttgccaaagc attctctgcc     180
gtctgggcgg gcatgaagga cgcccattgg gatcatcaca gccactttgt gcatggggat     240
cgcgccgtat ccgaatggac gttctccgga actggcgcgg acggcatgcg catcgaagca     300
cagggcgctg acctctttac cctgcgcgac ggcaagatca tcgtgaaaca ggccctgcgc     360
aaatcccgcc cgcccttcaa ggcttaa                                         387

<210> SEQ ID NO 31
<211> LENGTH: 128
<212> TYPE: PRT
<213> ORGANISM: Roseobacter denitrificans

<400> SEQUENCE: 31

Met Thr Lys Thr Leu Thr Ala Gln Asp Leu Ser Asp Thr Phe Asp Ala
1               5                   10                  15

Phe Asn Arg His Asp Val Asp Gly Val Met Thr His Phe Ala Asp Asp
            20                  25                  30

Cys Val Phe Tyr Thr Val Gly Gly Asp Glu Ala Tyr Gly Ala Lys Val
        35                  40                  45

Glu Gly Ala Glu Ala Ile Ala Lys Ala Phe Ser Ala Val Trp Ala Gly
    50                  55                  60

Met Lys Asp Ala His Trp Asp His His Ser His Phe Val His Gly Asp
65                  70                  75                  80

Arg Ala Val Ser Glu Trp Thr Phe Ser Gly Thr Gly Ala Asp Gly Met
                85                  90                  95

Arg Ile Glu Ala Gln Gly Ala Asp Leu Phe Thr Leu Arg Asp Gly Lys
            100                 105                 110

Ile Ile Val Lys Gln Ala Leu Arg Lys Ser Arg Pro Pro Phe Lys Ala
        115                 120                 125

<210> SEQ ID NO 32
<211> LENGTH: 1395
```

```
<212> TYPE: DNA
<213> ORGANISM: Roseobacter denitrificans

<400> SEQUENCE: 32
atgccacata gaccaaagca ctggcccaag gccagctacg atcccaaata cgatcctatc      60
gtcgacgcgg gtcccggtca caaccgggac cacgcaccga cctattggat tggtacggcg     120
gggacgccac ctgaagatga cgggccggtg tcgggtgaca tcgatgcgga tgtcgtcgtt     180
gtcggctctg gctatacagg tctgtctacc gcaatccacc tggcgaagga ccacggcatc     240
aaggcgcatg tccttgaagc aacacagtc gcctggggct gttccacccg caatggcggg      300
caggcacaga tttcttccgg tcgtctcaag cggtcggagt ggatcaagcg gtggggcgtg     360
gatgtcgcca aaggcatgca cgccgaggtc tgtgaagcct tcgaactgtt caatgatctg     420
atcgggtcag atgacattga ttgcgacccg caaaccgggg gccatttcta tattgcccac     480
cgcgaaaagg tcatggcgaa gctggaaaag gaatgtgccg tcctgaacga cacgtttggc     540
tatggctctc gcattctgtc gcgcgacgaa ctacacgaaa aatacgtgcg ggatcaggaa     600
gcacacggtg cccttggga accggacggg acctcgatcc acgcggcaaa actggccttc      660
agctacgtgc gtcttgcgcg caaactcggc gccaagatcc acacggccag cccggtcatg     720
gggtggaaga ccgtgaacgg tgtgcatcac ctcaccacgc ccggtggcac ggtgcgcgca     780
cgtgccgtgg ccttggcgac agcgggctac acaccgccgg ggctgaacga aaagaccaag     840
caccggctca tgccgatcct gtcaaactcc atcgtgacgc gtccgctgag cgatgaggaa     900
aaggcgggat gcggttttca ggtgaaatct ccgctgactg acacgcgcac cttgcggcac     960
tactaccgct atctgcccga cggacgggtc cagatcggca gccgcagtgc gattacaggt    1020
cgagacgcag agaaccccag acatctggag cttctgcaga aaggtctcta tcgcaagttc    1080
cccgtgctcg aaggcattga actggattac tcctggtggg gatgggtgga tgtcagccat    1140
gacatgatgc cacgcatttt ccagccaaac ccgaagcaaa caatctttta tgcgatgggc    1200
tacggcggca acggggtgat gtattccgca caggccggca gcgcatggc gcaaatggtt     1260
gcgggcgaag gcaaggacct caaacttccg atcttcacct cgcaactgcc aagccacggt    1320
gttctgacac ccttccgcag gttgggccag cgcatggcct acccctacta ctaccttcgc    1380
gatgaaattc tctga                                                     1395

<210> SEQ ID NO 33
<211> LENGTH: 464
<212> TYPE: PRT
<213> ORGANISM: Roseobacter denitrificans

<400> SEQUENCE: 33

Met Pro His Arg Pro Lys His Trp Pro Lys Ala Ser Tyr Asp Pro Lys
1               5                   10                  15

Tyr Asp Pro Ile Val Asp Ala Gly Pro Gly His Asn Arg Asp His Ala
            20                  25                  30

Pro Thr Tyr Trp Ile Gly Thr Ala Gly Thr Pro Pro Glu Asp Asp Gly
        35                  40                  45

Pro Val Ser Gly Asp Ile Asp Ala Asp Val Val Val Gly Ser Gly
    50                  55                  60

Tyr Thr Gly Leu Ser Thr Ala Ile His Leu Ala Lys Asp His Gly Ile
65                  70                  75                  80

Lys Ala His Val Leu Glu Ala Asn Thr Val Ala Trp Gly Cys Ser Thr
                85                  90                  95
```

Arg Asn Gly Gly Gln Ala Gln Ile Ser Ser Gly Arg Leu Lys Arg Ser
            100                 105                 110

Glu Trp Ile Lys Arg Trp Gly Val Asp Val Ala Lys Gly Met His Ala
        115                 120                 125

Glu Val Cys Glu Ala Phe Glu Leu Phe Asn Asp Leu Ile Gly Ser Asp
    130                 135                 140

Asp Ile Asp Cys Asp Pro Gln Thr Gly Gly His Phe Tyr Ile Ala His
145                 150                 155                 160

Arg Glu Lys Val Met Ala Lys Leu Glu Lys Glu Cys Ala Val Leu Asn
                165                 170                 175

Asp Thr Phe Gly Tyr Gly Ser Arg Ile Leu Ser Arg Asp Glu Leu His
            180                 185                 190

Glu Lys Tyr Val Arg Asp Gln Glu Ala His Gly Ala Leu Trp Glu Pro
        195                 200                 205

Asp Gly Thr Ser Ile His Ala Ala Lys Leu Ala Phe Ser Tyr Val Arg
    210                 215                 220

Leu Ala Arg Lys Leu Gly Ala Lys Ile His Thr Ala Ser Pro Val Met
225                 230                 235                 240

Gly Trp Lys Thr Val Asn Gly Val His His Leu Thr Thr Pro Gly Gly
                245                 250                 255

Thr Val Arg Ala Arg Ala Val Ala Leu Ala Thr Ala Gly Tyr Thr Pro
            260                 265                 270

Pro Gly Leu Asn Glu Lys Thr Lys His Arg Leu Met Pro Ile Leu Ser
        275                 280                 285

Asn Ser Ile Val Thr Arg Pro Leu Ser Asp Glu Lys Ala Gly Cys
    290                 295                 300

Gly Phe Gln Val Lys Ser Pro Leu Thr Asp Thr Arg Thr Leu Arg His
305                 310                 315                 320

Tyr Tyr Arg Tyr Leu Pro Asp Gly Arg Val Gln Ile Gly Ser Arg Ser
                325                 330                 335

Ala Ile Thr Gly Arg Asp Ala Glu Asn Pro Arg His Leu Glu Leu Leu
            340                 345                 350

Gln Lys Gly Leu Tyr Arg Lys Phe Pro Val Leu Glu Gly Ile Glu Leu
        355                 360                 365

Asp Tyr Ser Trp Trp Gly Trp Val Asp Val Ser His Asp Met Met Pro
    370                 375                 380

Arg Ile Phe Gln Pro Asn Pro Lys Gln Thr Ile Phe Tyr Ala Met Gly
385                 390                 395                 400

Tyr Gly Gly Asn Gly Val Met Tyr Ser Ala Gln Ala Gly Lys Arg Met
                405                 410                 415

Ala Gln Met Val Ala Gly Glu Gly Lys Asp Leu Lys Leu Pro Ile Phe
            420                 425                 430

Thr Ser Gln Leu Pro Ser His Gly Val Leu Thr Pro Phe Arg Arg Leu
        435                 440                 445

Gly Gln Arg Met Ala Tyr Pro Tyr Tyr Tyr Leu Arg Asp Glu Ile Leu
    450                 455                 460

<210> SEQ ID NO 34
<211> LENGTH: 1392
<212> TYPE: DNA
<213> ORGANISM: Roseobacter denitrificans

<400> SEQUENCE: 34
atggacggca atttcaatga aaatgatatc tcccgcgtcg tcgaagcaga ccgcgcgcat    60

```
atctggcacc atctgagcca gcacaaacct tacgagacaa cagacccgcg catcattgtc    120
gaaggcaagg gcatgaaggt ttgggaccag aagggcaaag agcatcttga tgccgtctcc    180
ggtggggtct ggaccgtcaa tgtcggctat ggccgcgaac gcatcgccaa cgccgtgcgg    240
gaccagttgg tcaagttgaa ctatttcgcc ggctccgcag gctccatccc cggtgccatg    300
ttcgccgagc gtctgatcga aaagatgccg gggctgagcc gcgtttatta ctgcaattcc    360
ggctccgagg cgaatgaaaa agccttcaag atggtccgcc agatcgcgca caaacgctat    420
ggcggcaaaa agcacaaggt gctttatcgc gagcgtgact atcacggcac caccatttcc    480
gccctttccg caggcgggca ggacgaacgg aacgcacaat atggcccctt cacgcccggt    540
ttcgtgcgcg tgccccattg ccttgaatac cgcgcctttg aacaggaagg ggcgccacag    600
gaaaactacg gtgtctgggc ggcggatcag atcgaaaagg taatcctcgc cgaagggccc    660
gataccgtgg gcggcctgtg ccttgaaccg gtcactgcag gtggcggggt gatcacgccc    720
cccgatggct actgggagcg tgtgcaggaa atctgccaca atacgacat cctgctgcat    780 atcgacgagg tcgtatgcgg cgtcggtcgg accggacat ggttcggcta tcagcactac    840
ggcatccagc cggatatggt cacgatggcc aagggtgtcg cgtccggtta cgcggcgatc    900
gcctgccttg tgaccaatga aaaagtcttc gacatgttca aggatgacgc ctcggatccg    960
ctgaactact ccgcgacat ctcgaccttt ggggctgca cggcgggtcc ggcagctgcg    1020
ctggaaaacc tgtcgatcat cgaagaagaa ggcctgctgg acaacaccac ggaacagggg    1080
gcctatatgc tcgactgtct gggcggcttg atggacaagc acaagatcat cggccaggtg    1140
cgcggcaagg ggctgttcct cggtgccgaa ctggtcgagg atcgcgacac gcgcaaaccg    1200
gttgacgaaa ggctcgcgca agcggtggtc gcggactgca tgcaacaggg tgtgatcatc    1260
ggcgtgacca accgctctct gccgggcaag aacaacacgc tgtgtttctc gcccgccctg    1320
atcgccagca aggatgacat tgaccacatc tgcgacgcgg tggacggtgc gctgtcgcgc    1380
gttttcggct aa                                                        1392
```

<210> SEQ ID NO 35
<211> LENGTH: 463
<212> TYPE: PRT
<213> ORGANISM: Roseobacter denitrificans

<400> SEQUENCE: 35

```
Met Asp Gly Asn Phe Asn Glu Asn Asp Ile Ser Arg Val Val Glu Ala
1               5                   10                  15

Asp Arg Ala His Ile Trp His His Leu Ser Gln His Lys Pro Tyr Glu
            20                  25                  30

Thr Thr Asp Pro Arg Ile Ile Val Glu Gly Lys Gly Met Lys Val Trp
        35                  40                  45

Asp Gln Lys Gly Lys Glu His Leu Asp Ala Val Ser Gly Gly Val Trp
    50                  55                  60

Thr Val Asn Val Gly Tyr Gly Arg Glu Arg Ile Ala Asn Ala Val Arg
65                  70                  75                  80

Asp Gln Leu Val Lys Leu Asn Tyr Phe Ala Gly Ser Ala Gly Ser Ile
                85                  90                  95

Pro Gly Ala Met Phe Ala Glu Arg Leu Ile Glu Lys Met Pro Gly Leu
            100                 105                 110

Ser Arg Val Tyr Tyr Cys Asn Ser Gly Ser Glu Ala Asn Glu Lys Ala
        115                 120                 125

Phe Lys Met Val Arg Gln Ile Ala His Lys Arg Tyr Gly Gly Lys Lys
```

130                 135                 140
His Lys Val Leu Tyr Arg Glu Arg Asp Tyr His Gly Thr Thr Ile Ser
145                 150                 155                 160

Ala Leu Ser Ala Gly Gly Gln Asp Glu Arg Asn Ala Gln Tyr Gly Pro
                165                 170                 175

Phe Thr Pro Gly Phe Val Arg Val Pro His Cys Leu Glu Tyr Arg Ala
            180                 185                 190

Phe Glu Gln Glu Gly Ala Pro Gln Glu Asn Tyr Gly Val Trp Ala Ala
        195                 200                 205

Asp Gln Ile Glu Lys Val Ile Leu Ala Glu Gly Pro Asp Thr Val Gly
    210                 215                 220

Gly Leu Cys Leu Glu Pro Val Thr Ala Gly Gly Val Ile Thr Pro
225                 230                 235                 240

Pro Asp Gly Tyr Trp Glu Arg Val Gln Glu Ile Cys His Lys Tyr Asp
                245                 250                 255

Ile Leu Leu His Ile Asp Glu Val Val Cys Gly Val Gly Arg Thr Gly
            260                 265                 270

Thr Trp Phe Gly Tyr Gln His Tyr Gly Ile Gln Pro Asp Met Val Thr
        275                 280                 285

Met Ala Lys Gly Val Ala Ser Gly Tyr Ala Ala Ile Ala Cys Leu Val
    290                 295                 300

Thr Asn Glu Lys Val Phe Asp Met Phe Lys Asp Asp Ala Ser Asp Pro
305                 310                 315                 320

Leu Asn Tyr Phe Arg Asp Ile Ser Thr Phe Gly Gly Cys Thr Ala Gly
                325                 330                 335

Pro Ala Ala Ala Leu Glu Asn Leu Ser Ile Ile Glu Glu Glu Gly Leu
            340                 345                 350

Leu Asp Asn Thr Thr Glu Gln Gly Ala Tyr Met Leu Asp Cys Leu Gly
        355                 360                 365

Gly Leu Met Asp Lys His Lys Ile Ile Gly Gln Val Arg Gly Lys Gly
    370                 375                 380

Leu Phe Leu Gly Ala Glu Leu Val Glu Asp Arg Asp Thr Arg Lys Pro
385                 390                 395                 400

Val Asp Glu Arg Leu Ala Gln Ala Val Val Ala Asp Cys Met Gln Gln
                405                 410                 415

Gly Val Ile Ile Gly Val Thr Asn Arg Ser Leu Pro Gly Lys Asn Asn
            420                 425                 430

Thr Leu Cys Phe Ser Pro Ala Leu Ile Ala Ser Lys Asp Asp Ile Asp
        435                 440                 445

His Ile Cys Asp Ala Val Asp Gly Ala Leu Ser Arg Val Phe Gly
    450                 455                 460

<210> SEQ ID NO 36
<211> LENGTH: 951
<212> TYPE: DNA
<213> ORGANISM: Escherichia coli

<400> SEQUENCE: 36
atgaatttcc aacaactaaa gataatccgc gaggctgcac gtcaggatta caacctgaca     60
gaggttgcga atatgctttt tacctcacag tcaggcgtca gccgtcatat tcgggaactg    120
gaggatgaac ttggcatcga aatatttgtt cgacgaggta agcgactgct gggcatgact    180
gaaccgggca agcattact ggtcattgca gaacgtattc tgaatgaagc cagtaatgtt    240
cgtcggcttg cagacctgtt taccaacgat acgtctggcg ttctcactat tgcaacgacg    300

```
catactcagg cacgttatag cttgccagag gtcattaaag cttttcgcga acttttcccg      360
gaggttcggc tcgagctaat ccaggggacg ccacaggaaa ttgcgacatt gttgcaaaat      420
ggcgaagctg atattggtat cgccagcgag cgtttgagta atgacccgca gctcgtcgcc      480
ttcccgtggt ttcgttggca ccatagtttg cttgttccac acgatcatcc cttgacgcaa      540
atttcaccat tgacgctgga atcaatagcg aagtggccgt taatcactta ccgacagggg      600
attacggggc gctcacgtat tgatgacgca tttgcccgca aaggtttgct ggcagatatt      660
gtattaagtg cgcaggattc tgatgtcatt aaaacctatg ttgctcttgg cttgggatc       720
ggattagttg ccgagcaatc cagtggcgaa caagaggaag agaatttaat ccgcctggat      780
acgcggcatc tttttgatgc taatactgtc tggttgggac tgaagcgagg acaacttcag      840
cgtaactatg tctggcgctt tctggaactt tgtaatgcag gactgtcagt tgaggatatc      900
aagcggcagg tgatggaaag cagtgaagag gaaattgatt atcagatata g              951
```

<210> SEQ ID NO 37
<211> LENGTH: 316
<212> TYPE: PRT
<213> ORGANISM: Escherichia coli

<400> SEQUENCE: 37

```
Met Asn Phe Gln Gln Leu Lys Ile Ile Arg Glu Ala Ala Arg Gln Asp
1               5                   10                  15

Tyr Asn Leu Thr Glu Val Ala Asn Met Leu Phe Thr Ser Gln Ser Gly
            20                  25                  30

Val Ser Arg His Ile Arg Glu Leu Glu Asp Glu Leu Gly Ile Glu Ile
        35                  40                  45

Phe Val Arg Arg Gly Lys Arg Leu Leu Gly Met Thr Glu Pro Gly Lys
    50                  55                  60

Ala Leu Leu Val Ile Ala Glu Arg Ile Leu Asn Glu Ala Ser Asn Val
65                  70                  75                  80

Arg Arg Leu Ala Asp Leu Phe Thr Asn Asp Thr Ser Gly Val Leu Thr
                85                  90                  95

Ile Ala Thr Thr His Thr Gln Ala Arg Tyr Ser Leu Pro Glu Val Ile
            100                 105                 110

Lys Ala Phe Arg Glu Leu Phe Pro Glu Val Arg Leu Glu Leu Ile Gln
        115                 120                 125

Gly Thr Pro Gln Glu Ile Ala Thr Leu Leu Gln Asn Gly Glu Ala Asp
    130                 135                 140

Ile Gly Ile Ala Ser Glu Arg Leu Ser Asn Asp Pro Gln Leu Val Ala
145                 150                 155                 160

Phe Pro Trp Phe Arg Trp His His Ser Leu Leu Val Pro His Asp His
                165                 170                 175

Pro Leu Thr Gln Ile Ser Pro Leu Thr Leu Glu Ser Ile Ala Lys Trp
            180                 185                 190

Pro Leu Ile Thr Tyr Arg Gln Gly Ile Thr Gly Arg Ser Arg Ile Asp
        195                 200                 205

Asp Ala Phe Ala Arg Lys Gly Leu Leu Ala Asp Ile Val Leu Ser Ala
    210                 215                 220

Gln Asp Ser Asp Val Ile Lys Thr Tyr Val Ala Leu Gly Leu Gly Ile
225                 230                 235                 240

Gly Leu Val Ala Glu Gln Ser Ser Gly Glu Gln Glu Glu Glu Asn Leu
                245                 250                 255
```

Ile Arg Leu Asp Thr Arg His Leu Phe Asp Ala Asn Thr Val Trp Leu
    260                 265                 270

Gly Leu Lys Arg Gly Gln Leu Gln Arg Asn Tyr Val Trp Arg Phe Leu
        275                 280                 285

Glu Leu Cys Asn Ala Gly Leu Ser Val Glu Asp Ile Lys Arg Gln Val
    290                 295                 300

Met Glu Ser Ser Glu Glu Ile Asp Tyr Gln Ile
305                 310                 315

<210> SEQ ID NO 38
<211> LENGTH: 927
<212> TYPE: DNA
<213> ORGANISM: Corynebacterium glutamicum

<400> SEQUENCE: 38
atggacaacg acggcggaga catgcgaatc gacgacctac gcagcttcat ttcagtcgcc    60
caatcaggcc acctcaccga aaccgccgaa agattaggca tcccgcagcc cacactttcc   120
agacgaatca gccgagtgga aaaacacgca ggcaccccac ttttcgaccg cgccggccgc   180
aaactcgtcc tcaaccaacg aggccacgcc ttcctcaacc acgccagcgc catcgtcgca   240
gaattcaact ccgccgcaac tgaaatcaaa cgcctcatgg acccagaaaa aggcacaatc   300
cgactggact tcatgcattc cttgggcact tggatggtcc ccgaacttat ccgaacattc   360
cgcgccgaac accccaatgt agaattccaa ctccaccaag cggcagcaat gctcctggta   420
gatcgtgttt ggctgatga aactgacctc gcattagttg ccccaaaacc tgccgaggtt   480
ggtacctctt tagggtgggc gccactgctt cgtcaacgac ttgccctagc tgttcccgca   540
gatcaccggc ttgcctcttt ttctggccaa ggagaattgc cgttgattag tgcgacggaa   600
gaaccttttcg tggcgatgcg agcaggtttc ggcacccgac tcctcatgga tgcattagcc   660
gaagaagccg gttttgttcc caatgtggtt ttcgaatcca tggagctcac caccgtcgca   720
gggcttgtca gcgcaggtct cggcgttggt gtggttccga tggatgatcc gtaccttccc   780
acagtgggaa tcgtgcaacg cccacttagt ccacccgcat atagggaact cggtctggta   840
tggaggctta acgcgggacc tgcaccggcc gtggataact tccggaagtt cgtggcggga   900
tcgagatatg cattagaaga gggctga                                        927

<210> SEQ ID NO 39
<211> LENGTH: 308
<212> TYPE: PRT
<213> ORGANISM: Corynebacterium glutamicum

<400> SEQUENCE: 39

Met Asp Asn Asp Gly Gly Asp Met Arg Ile Asp Asp Leu Arg Ser Phe
1               5                   10                  15

Ile Ser Val Ala Gln Ser Gly His Leu Thr Glu Thr Ala Glu Arg Leu
            20                  25                  30

Gly Ile Pro Gln Pro Thr Leu Ser Arg Arg Ile Ser Arg Val Glu Lys
        35                  40                  45

His Ala Gly Thr Pro Leu Phe Asp Arg Ala Gly Arg Lys Leu Val Leu
    50                  55                  60

Asn Gln Arg Gly His Ala Phe Leu Asn His Ala Ser Ala Ile Val Ala
65                  70                  75                  80

Glu Phe Asn Ser Ala Ala Thr Glu Ile Lys Arg Leu Met Asp Pro Glu
                85                  90                  95

Lys Gly Thr Ile Arg Leu Asp Phe Met His Ser Leu Gly Thr Trp Met

```
            100                 105                 110
Val Pro Glu Leu Ile Arg Thr Phe Arg Ala Glu His Pro Asn Val Glu
            115                 120                 125

Phe Gln Leu His Gln Ala Ala Ala Met Leu Leu Val Asp Arg Val Leu
            130                 135                 140

Ala Asp Glu Thr Asp Leu Ala Leu Val Gly Pro Lys Pro Ala Glu Val
145                 150                 155                 160

Gly Thr Ser Leu Gly Trp Ala Pro Leu Leu Arg Gln Arg Leu Ala Leu
                    165                 170                 175

Ala Val Pro Ala Asp His Arg Leu Ala Ser Phe Ser Gly Gln Gly Glu
                180                 185                 190

Leu Pro Leu Ile Ser Ala Thr Glu Glu Pro Phe Val Ala Met Arg Ala
            195                 200                 205

Gly Phe Gly Thr Arg Leu Leu Met Asp Ala Leu Ala Glu Glu Ala Gly
        210                 215                 220

Phe Val Pro Asn Val Val Phe Glu Ser Met Glu Leu Thr Thr Val Ala
225                 230                 235                 240

Gly Leu Val Ser Ala Gly Leu Gly Val Gly Val Pro Met Asp Asp
                    245                 250                 255

Pro Tyr Leu Pro Thr Val Gly Ile Val Gln Arg Pro Leu Ser Pro Pro
                260                 265                 270

Ala Tyr Arg Glu Leu Gly Leu Val Trp Arg Leu Asn Ala Gly Pro Ala
            275                 280                 285

Pro Ala Val Asp Asn Phe Arg Lys Phe Val Ala Gly Ser Arg Tyr Ala
            290                 295                 300

Leu Glu Glu Gly
305

<210> SEQ ID NO 40
<211> LENGTH: 1362
<212> TYPE: DNA
<213> ORGANISM: Corynebacterium glutamicum

<400> SEQUENCE: 40
atgcttgccg accttcccat cgccttaaac ccacacgaac caacatccat ccccacgcag    60
ctcacagaac agatccgtcg tctcgtggcg aggggaattc tcaccccagg agacccgctt   120
cccagcagtc gctcactatc cacccaattg ggggtatccc gcggcagtgt ggtgaccgct   180
tatgaccaat tggccggtga aggctacctc agcaccgccc gcggttccgg tacaacgatc   240
aacccagatc tgcatttgtt gaagcctgtg gaaattgaga agaaggagac gtcgagaagc   300
gtcccgcccc gctgctcaa cctgagcccc ggcgtgcccg ataccgcgac gctcgccgat   360
tccgcatggc gcgctgcgtg gcgcgaagcc tgcgccaagc cacccacgca ctccctgag   420 cagggacttt tgaggctgcg gatcgagatc gccgaccacc tgcgccagat gcgtggcctc   480
atggtcgagc cggagcagat catcgtcacc gccggcgcgc gcgaggggct gagtctgctg   540
ctgcgcacca tggatgcgcc tgcccgcatc ggcgtcgaat cgcccggcta ccccagcctg   600
cgccgcatcc gcaggtgct tggccatgag acgatcgatg tgccgaccga cgaatccggc   660
ctcgtacccc gcgcgctgcc ccacgacctc aacgcgctac tggtaacccc tagccatcaa   720
tatccctacg gcggctcgct gcccgccgat cgccgcaccg gctagtcgc gtgggctgag   780 gcaaacgatg cgttgcttat tgaagacgac ttcgattctg agctgcgcta cgtcggtatg   840
ccgcttccgc cgctgcgtgc gctggcgccc gatcgcacga ttctgctcgg cacgttttcc   900
```

```
tccgtgatca caccacaagt cgcctgcgga tacctcatcg cgccgacgcc ccaggcgcgc    960
gtgctcgcca cgcttcgcgg gattctcggc cagccagtcg gcgccatcac ccaacacgcg   1020
ctcgcgtcct acctcgcctc aggcgcttta cgacgccgca cccaacgttt gcggcgcctt   1080
taccgacacc gccgctccat cgtccaagac ccctcggtg acctcccgaa tacgcagctt    1140
cgccccatca acggtggcct ccacgcagtt ctcctttgcg acaaacccca agacctcgtc   1200
gtcaccacac tcgcctcccg aggccttaac gtcaccgcgc tttcccacta ctggggcggc   1260
accggcgcag acaacggcat cgtcttcggc ttcggctccc acgacgaaga caccctcaga   1320
tgggtgcttg ctgagatcag cgatgcggtg tctctaggct aa                       1362
```

<210> SEQ ID NO 41
<211> LENGTH: 453
<212> TYPE: PRT
<213> ORGANISM: Corynebacterium glutamicum

<400> SEQUENCE: 41

```
Met Leu Ala Asp Leu Pro Ile Ala Leu Asn Pro His Glu Pro Thr Ser
1               5                   10                  15

Ile Pro Thr Gln Leu Thr Glu Gln Ile Arg Arg Leu Val Ala Arg Gly
                20                  25                  30

Ile Leu Thr Pro Gly Asp Pro Leu Pro Ser Ser Arg Ser Leu Ser Thr
            35                  40                  45

Gln Leu Gly Val Ser Arg Gly Ser Val Val Thr Ala Tyr Asp Gln Leu
        50                  55                  60

Ala Gly Glu Gly Tyr Leu Ser Thr Ala Arg Gly Ser Gly Thr Thr Ile
65                  70                  75                  80

Asn Pro Asp Leu His Leu Leu Lys Pro Val Glu Ile Glu Lys Lys Glu
                85                  90                  95

Thr Ser Arg Ser Val Pro Pro Leu Leu Asn Leu Ser Pro Gly Val
                100                 105                 110

Pro Asp Thr Ala Thr Leu Ala Asp Ser Ala Trp Arg Ala Ala Trp Arg
            115                 120                 125

Glu Ala Cys Ala Lys Pro Pro Thr His Ser Pro Glu Gln Gly Leu Leu
        130                 135                 140

Arg Leu Arg Ile Glu Ile Ala Asp His Leu Arg Gln Met Arg Gly Leu
145                 150                 155                 160

Met Val Glu Pro Glu Gln Ile Ile Val Thr Ala Gly Ala Arg Glu Gly
                165                 170                 175

Leu Ser Leu Leu Leu Arg Thr Met Asp Ala Pro Ala Arg Ile Gly Val
            180                 185                 190

Glu Ser Pro Gly Tyr Pro Ser Leu Arg Arg Ile Pro Gln Val Leu Gly
        195                 200                 205

His Glu Thr Ile Asp Val Pro Thr Asp Glu Ser Gly Leu Val Pro Arg
    210                 215                 220

Ala Leu Pro His Asp Leu Asn Ala Leu Leu Val Thr Pro Ser His Gln
225                 230                 235                 240

Tyr Pro Tyr Gly Gly Ser Leu Pro Ala Asp Arg Arg Thr Ala Leu Val
                245                 250                 255

Ala Trp Ala Glu Ala Asn Asp Ala Leu Ile Glu Asp Asp Phe Asp
            260                 265                 270

Ser Glu Leu Arg Tyr Val Gly Met Pro Leu Pro Pro Leu Arg Ala Leu
        275                 280                 285

Ala Pro Asp Arg Thr Ile Leu Leu Gly Thr Phe Ser Ser Val Ile Thr
```

```
                290             295             300
Pro Gln Val Ala Cys Gly Tyr Leu Ile Ala Pro Thr Pro Gln Ala Arg
305             310             315             320

Val Leu Ala Thr Leu Arg Gly Ile Leu Gly Gln Pro Val Gly Ala Ile
            325             330             335

Thr Gln His Ala Leu Ala Ser Tyr Leu Ala Ser Gly Ala Leu Arg Arg
            340             345             350

Arg Thr Gln Arg Leu Arg Arg Leu Tyr Arg His Arg Arg Ser Ile Val
            355             360             365

Gln Asp Thr Leu Gly Asp Leu Pro Asn Thr Gln Leu Arg Pro Ile Asn
        370             375             380

Gly Gly Leu His Ala Val Leu Leu Cys Asp Lys Pro Gln Asp Leu Val
385             390             395             400

Val Thr Thr Leu Ala Ser Arg Gly Leu Asn Val Thr Ala Leu Ser His
            405             410             415

Tyr Trp Gly Gly Thr Gly Ala Asp Asn Gly Ile Val Phe Gly Phe Gly
            420             425             430

Ser His Asp Glu Asp Thr Leu Arg Trp Val Leu Ala Glu Ile Ser Asp
            435             440             445

Ala Val Ser Leu Gly
    450

<210> SEQ ID NO 42
<211> LENGTH: 1464
<212> TYPE: DNA
<213> ORGANISM: Artificial Sequence
<220> FEATURE:
<223> OTHER INFORMATION: Synthetic construct

<400> SEQUENCE: 42
atggcgattt ccccgaaac cttctttctc gcctccgaag ccgagggcac gctccagacc      60
cggatccgcc agatggtggc cgaggggatc ctgaccggcc gcttccgccc gggcgagaaa     120
ctgccctcct cgcgcaagct cgccgcgcat ctgggcgtca gccggatcac cgtgacactc     180
gcctataccg aacttcaggc cgacgattac atcacctcgc gcggccggtc gggctattac     240
gtgtccgaca acgcgcccga accgccgtcc tttcccgcgc gcgcacccgg gcagtcgtcg     300
gtcgactggt cgcgcgccat cggccagcgg tttcgcggca ccgaaccgca ttcgaaaccc     360
ggcaactggg ccgatttccg ctatccgttc atctatggcc aggccgatcc gaccctgttc     420
gacgcggcca attggcggct ctgtgccctc caggccctgg ggcgcaagga tttcgccgcg     480
ctgaccaccg attacaacga cagcgacgat cccgaattgc tggatttcat cgcccgccag     540
atcctgcccc gccgcggcat cctggccggg ccggacgaaa tcctgctgac gctgggcgcc     600
cagaacgcgc tgtggctgac cgcccaggtg ctgctgaccc agcgccggac cgcggcgatc     660
gaggatccct gctaccccggc cctgcgcggc atcctgaccc aggcgcgctg ccacctgcac     720
gcggtcccgg tggatcgcga cgggttgccg cccgaggcga tccccgacgg caccaacgtg     780
gtgttctgca ccccagcca ccaatgcccg accaccgcga ccatgccgat gtcgcgccgc     840
catgccctgc tggaacgcgc cgaggccgag gatttcctga tcgtcgagga tgattacgaa     900
ttcgagatgt cgttcctcaa atcccccctcg ccggcgctga atcgctcga ccggcacggg     960
cgggtgatct acgtcggctc tttctccaaa tcgctgtttc cgggcctgcg cctgggctat    1020
ctggtcggcc ccgagccgtt catccgggag gcccgcgccc tgcgtgccag cgtgctgcgc    1080
cacccgccgg gccatatcca gcgcaccgtc acctatttcc tgtctcttgg ccattacgac    1140
```

-continued

```
gccctgatcc gccgcatggg ccgggcctat cacgaccggc gccggatcat ggaccgcgcc    1200
ctgcacgatc acgggctgac cgtcgccgga tcgggctcct tcggcggctc gtccttctgg    1260
atgcgcgcgc ccgcgggcgt cgatacggcc gagctggccc gccgcctgtc cgccgacagc    1320
gtgctgatcg aaccgggcca gccgttcttt gccggcaccg cgccgcccgg cggttctac     1380 cgcctggcct atagttcgat ctctggcccg cgcatccccg acgggatcgc gcggatcgcc    1440
gccgcgctgg agaactggtc ctag                                           1464
```

<210> SEQ ID NO 43
<211> LENGTH: 487
<212> TYPE: PRT
<213> ORGANISM: Artificial Sequence
<220> FEATURE:
<223> OTHER INFORMATION: Synthetic construct

<400> SEQUENCE: 43

```
Met Ala Ile Ser Pro Glu Thr Phe Phe Leu Ala Ser Glu Ala Glu Gly
1               5                   10                  15

Thr Leu Gln Thr Arg Ile Arg Gln Met Val Ala Glu Gly Ile Leu Thr
            20                  25                  30

Gly Arg Phe Arg Pro Gly Glu Lys Leu Pro Ser Ser Arg Lys Leu Ala
        35                  40                  45

Ala His Leu Gly Val Ser Arg Ile Thr Val Thr Leu Ala Tyr Thr Glu
    50                  55                  60

Leu Gln Ala Asp Asp Tyr Ile Thr Ser Arg Gly Arg Ser Gly Tyr Tyr
65                  70                  75                  80

Val Ser Asp Asn Ala Pro Glu Pro Ser Phe Pro Ala Arg Ala Pro
                85                  90                  95

Gly Gln Ser Ser Val Asp Trp Ser Arg Ala Ile Gly Arg Phe Arg
            100                 105                 110

Gly Thr Glu Pro His Ser Lys Pro Gly Asn Trp Ala Asp Phe Arg Tyr
        115                 120                 125

Pro Phe Ile Tyr Gly Gln Ala Asp Pro Thr Leu Phe Asp Ala Ala Asn
    130                 135                 140

Trp Arg Leu Cys Ala Leu Gln Ala Leu Gly Arg Lys Asp Phe Ala Ala
145                 150                 155                 160

Leu Thr Thr Asp Tyr Asn Asp Ser Asp Pro Glu Leu Leu Asp Phe
                165                 170                 175

Ile Ala Arg Gln Ile Leu Pro Arg Arg Gly Ile Leu Ala Gly Pro Asp
            180                 185                 190

Glu Ile Leu Leu Thr Leu Gly Ala Gln Asn Ala Leu Trp Leu Thr Ala
        195                 200                 205

Gln Val Leu Leu Thr Gln Arg Arg Thr Ala Ala Ile Glu Asp Pro Cys
    210                 215                 220

Tyr Pro Ala Leu Arg Gly Ile Leu Thr Gln Ala Arg Cys His Leu His
225                 230                 235                 240

Ala Val Pro Val Asp Arg Asp Gly Leu Pro Pro Glu Ala Ile Pro Asp
                245                 250                 255

Gly Thr Asn Val Val Phe Cys Thr Pro Ser His Gln Cys Pro Thr Thr
            260                 265                 270

Ala Thr Met Pro Met Ser Arg Arg His Ala Leu Leu Glu Arg Ala Glu
        275                 280                 285

Ala Glu Asp Phe Leu Ile Val Glu Asp Asp Tyr Glu Phe Glu Met Ser
    290                 295                 300
```

```
Phe Leu Lys Ser Pro Ser Pro Ala Leu Lys Ser Leu Asp Arg His Gly
305                 310                 315                 320

Arg Val Ile Tyr Val Gly Ser Phe Ser Lys Ser Leu Phe Pro Gly Leu
            325                 330                 335

Arg Leu Gly Tyr Leu Val Gly Pro Glu Pro Phe Ile Arg Glu Ala Arg
        340                 345                 350

Ala Leu Arg Ala Ser Val Leu Arg His Pro Pro Gly His Ile Gln Arg
    355                 360                 365

Thr Val Thr Tyr Phe Leu Ser Leu Gly His Tyr Asp Ala Leu Ile Arg
370                 375                 380

Arg Met Gly Arg Ala Tyr His Asp Arg Arg Ile Met Asp Arg Ala
385                 390                 395                 400

Leu His Asp His Gly Leu Thr Val Ala Gly Ser Gly Ser Phe Gly Gly
            405                 410                 415

Ser Ser Phe Trp Met Arg Ala Pro Ala Gly Val Asp Thr Ala Glu Leu
        420                 425                 430

Ala Arg Arg Leu Ser Ala Asp Ser Val Leu Ile Glu Pro Gly Gln Pro
    435                 440                 445

Phe Phe Ala Gly Thr Ala Pro Pro Gly Arg Phe Tyr Arg Leu Ala Tyr
450                 455                 460

Ser Ser Ile Ser Gly Pro Arg Ile Pro Asp Gly Ile Ala Arg Ile Ala
465                 470                 475                 480

Ala Ala Leu Glu Asn Trp Ser
                485

<210> SEQ ID NO 44
<211> LENGTH: 70
<212> TYPE: DNA
<213> ORGANISM: Escherichia coli

<400> SEQUENCE: 44
ctgcgcgcgt tacagcgccg cctgacgccc tggcatggag aagtacaatg attccgggga    60
tccgtcgacc                                                          70

<210> SEQ ID NO 45
<211> LENGTH: 70
<212> TYPE: DNA
<213> ORGANISM: Escherichia coli

<400> SEQUENCE: 45 aggggcgag gggaccgtcc actctcgtat taccccgccc gataaaacgg tgtaggctgg    60
agctgcttcg                                                          70

<210> SEQ ID NO 46
<211> LENGTH: 70
<212> TYPE: DNA
<213> ORGANISM: Escherichia coli

<400> SEQUENCE: 46
attagacttt aacaataacg ggaaatctga actgcccgga gtttaccgtg attccgggga    60
tccgtcgacc                                                          70

<210> SEQ ID NO 47
<211> LENGTH: 70
<212> TYPE: DNA
<213> ORGANISM: Escherichia coli
```

<400> SEQUENCE: 47
aaaagcccgc ttttatagcg ggattttttgc tatatctgat aatcaatttc tgtaggctgg    60
agctgcttcg                                                            70

<210> SEQ ID NO 48
<211> LENGTH: 70
<212> TYPE: DNA
<213> ORGANISM: Escherichia coli

<400> SEQUENCE: 48
attcgccagc gcatctggca gcccactcaa ctggaaggaa acaattatg attccgggga      60 tccgtcgacc                                                            70

<210> SEQ ID NO 49
<211> LENGTH: 70
<212> TYPE: DNA
<213> ORGANISM: Escherichia coli

<400> SEQUENCE: 49
tcttcactgg cgttgccatt atttcttcct tagctttgcg cgactttacg tgtaggctgg    60
agctgcttcg                                                            70

<210> SEQ ID NO 50
<211> LENGTH: 70
<212> TYPE: DNA
<213> ORGANISM: Escherichia coli

<400> SEQUENCE: 50
gttatcaatg ttaacaaaaa aagaacaatt ggttataagg agagagtatg attccgggga    60
tccgtcgacc                                                            70

<210> SEQ ID NO 51
<211> LENGTH: 70
<212> TYPE: DNA
<213> ORGANISM: Escherichia coli

<400> SEQUENCE: 51
gcaatcccgc cagcgccagt ttaatgatgt tacgcatggg cattacctcg tgtaggctgg    60
agctgcttcg                                                            70

<210> SEQ ID NO 52
<211> LENGTH: 29
<212> TYPE: DNA
<213> ORGANISM: Corynebacterium glutamicum

<400> SEQUENCE: 52
cgcggatccc tttccattgg ttcctatcc                                       29

<210> SEQ ID NO 53
<211> LENGTH: 41
<212> TYPE: DNA
<213> ORGANISM: Corynebacterium glutamicum

<400> SEQUENCE: 53
cttcgatgcg atcggcgacc tcgggaggtg ccggattttt c                         41

<210> SEQ ID NO 54
<211> LENGTH: 41
<212> TYPE: DNA
<213> ORGANISM: Corynebacterium glutamicum

<400> SEQUENCE: 54
gaaaaatccg gcacctcccg aggtcgccga tcgcatcgaa g                41

<210> SEQ ID NO 55
<211> LENGTH: 29
<212> TYPE: DNA
<213> ORGANISM: Corynebacterium glutamicum

<400> SEQUENCE: 55
cccaagcttc ccaacaggtt ccaaaactc                              29

<210> SEQ ID NO 56
<211> LENGTH: 29
<212> TYPE: DNA
<213> ORGANISM: Corynebacterium glutamicum

<400> SEQUENCE: 56
cgcggatccg cataattttg tcagtggtg                              29

<210> SEQ ID NO 57
<211> LENGTH: 40
<212> TYPE: DNA
<213> ORGANISM: Corynebacterium glutamicum

<400> SEQUENCE: 57
acctgattct tctgatcgcc ctggcgcgca tccgcacgcg                  40

<210> SEQ ID NO 58
<211> LENGTH: 41
<212> TYPE: DNA
<213> ORGANISM: Corynebacterium glutamicum

<400> SEQUENCE: 58
cgcgtgcgga tgcgcgccag ggcgatcaga agaatcaggt g                41

<210> SEQ ID NO 59
<211> LENGTH: 30
<212> TYPE: DNA
<213> ORGANISM: Corynebacterium glutamicum

<400> SEQUENCE: 59
cccaagcttt agaacagcgc gctggccatc                             30

<210> SEQ ID NO 60
<211> LENGTH: 29
<212> TYPE: DNA
<213> ORGANISM: Corynebacterium glutamicum

<400> SEQUENCE: 60
cgcggatccc aacgacggcg gagacatgc                              29

<210> SEQ ID NO 61
<211> LENGTH: 43
<212> TYPE: DNA
<213> ORGANISM: Corynebacterium glutamicum

<400> SEQUENCE: 61
ccatcggaac cacaccaacg ccggccggcg cggtcgaaaa gtg              43

<210> SEQ ID NO 62
<211> LENGTH: 43
<212> TYPE: DNA

```
<213> ORGANISM: Corynebacterium glutamicum

<400> SEQUENCE: 62 cactttcga ccgcgccggc cggcgttggt gtggttccga tgg          43

<210> SEQ ID NO 63
<211> LENGTH: 30
<212> TYPE: DNA
<213> ORGANISM: Corynebacterium glutamicum

<400> SEQUENCE: 63
cccaagcttg gccggcgcgg tcgaaaagtg                         30

<210> SEQ ID NO 64
<211> LENGTH: 30
<212> TYPE: DNA
<213> ORGANISM: Corynebacterium glutamicum

<400> SEQUENCE: 64
cgcggatccc cttcccatcg ccttaaaccc                         30

<210> SEQ ID NO 65
<211> LENGTH: 41
<212> TYPE: DNA
<213> ORGANISM: Corynebacterium glutamicum

<400> SEQUENCE: 65
cgaggtcttg gggtttgtcg cctgggaagc gggtctcctg g            41

<210> SEQ ID NO 66
<211> LENGTH: 41
<212> TYPE: DNA
<213> ORGANISM: Corynebacterium glutamicum

<400> SEQUENCE: 66
ccaggagacc cgcttcccag gcgacaaacc ccaagacctc g            41

<210> SEQ ID NO 67
<211> LENGTH: 31
<212> TYPE: DNA
<213> ORGANISM: Corynebacterium glutamicum

<400> SEQUENCE: 67
cccaagcttg cctagagaca ccgcatcgct g                       31

<210> SEQ ID NO 68
<211> LENGTH: 102
<212> TYPE: DNA
<213> ORGANISM: Artificial Sequence
<220> FEATURE:
<223> OTHER INFORMATION: Synthetic construct

<400> SEQUENCE: 68
acccgttttt tgggctaacg ggaggaatta accatggtgt agatgggcgc atcgtaaccg   60
tgcatctgcc agtttgaggg gacgacgaca gtatcggcct ca                    102
```